US012790304B2

(12) United States Patent
Stock et al.

(10) Patent No.: US 12,790,304 B2
(45) Date of Patent: Nov. 10, 2026

(54) COMPOSITIONS FOR TRANSFECTING mRNA INTO A CELL AND THEIR APPLICATIONS

(71) Applicant: POLYPLUS TRANSFECTION, Illkirch Graffenstaden (FR)

(72) Inventors: Fabrice Stock, Benfeld (FR); Valérie Toussaint Moreau, Illkirch (FR); Patrick Erbacher, Benfeld (FR)

(73) Assignee: SARTORIUS POLYPLUS, Illkirch-Graffenstaden (FR)

(*) Notice: Subject to any disclaimer, the term of this patent is extended or adjusted under 35 U.S.C. 154(b) by 1454 days.

(21) Appl. No.: 17/289,443

(22) PCT Filed: Oct. 30, 2019

(86) PCT No.: PCT/EP2019/079742

§ 371 (c)(1),
(2) Date: Apr. 28, 2021

(87) PCT Pub. No.: WO2020/089342

PCT Pub. Date: May 7, 2020

(65) Prior Publication Data

US 2021/0386841 A1 Dec. 16, 2021

(30) Foreign Application Priority Data

Oct. 30, 2018 (EP) .................................... 18306417

(51) Int. Cl.

*C07D 233/58* (2006.01)
*A61K 31/7105* (2006.01)
(Continued)

(52) U.S. Cl.

CPC ........ *C07D 233/58* (2013.01); *A61K 31/7105* (2013.01); *A61K 39/0011* (2013.01);
(Continued)

(58) Field of Classification Search

None
See application file for complete search history.

(56) References Cited

U.S. PATENT DOCUMENTS

| | | | |
|---|---|---|---|
| 5,627,159 | A | 5/1997 | Shih et al. |
| 7,479,573 | B2 | 1/2009 | Chu et al. |

(Continued)

FOREIGN PATENT DOCUMENTS

| | | | |
|---|---|---|---|
| EP | 2 860 255 | | 4/2015 |
| WO | WO 2017218891 | * | 12/2017 |
| WO | WO 2018112470 | * | 6/2018 |

OTHER PUBLICATIONS

Cai et al. (RNA, 2004, 10:1957-1966). (Year: 2004).*

(Continued)

*Primary Examiner* — Renee Claytor
*Assistant Examiner* — Jennifer C Sawyer
(74) *Attorney, Agent, or Firm* — NIXON & VANDERHYE

(57) ABSTRACT

Disclosed are compositions for transfecting a messenger RNA (mRNA) into a cell and their applications. The present invention is directed to a composition for transfecting a mRNA into a cell including a mRNA, at least one neutral lipid and a cationic lipid of formula (I), wherein $R_1$ $R_2$, $R_3$, $R_4$ and $R_5$, $(CH_2)_n$ and $A^-$ are as defined in the description. Also disclosed are uses of the composition and to a method for in vitro transfection of live cells.

15 Claims, 2 Drawing Sheets

(I)

(51) Int. Cl.
*A61K 39/00* (2006.01)
*A61K 47/60* (2017.01)
*C12N 15/88* (2006.01)

(52) U.S. Cl.
CPC .............. *A61K 47/60* (2017.08); *C12N 15/88* (2013.01); *A61K 2039/53* (2013.01)

(56) References Cited

U.S. PATENT DOCUMENTS

| | | | | |
|---|---|---|---|---|
| 8,399,422 | B2 | 3/2013 | Neuberg | |
| 2004/0072769 | A1 * | 4/2004 | Yin | G16B 30/10<br>435/6.12 |
| 2010/0048672 | A1 | 2/2010 | Neuberg et al. | |
| 2020/0085758 | A1 * | 3/2020 | Farokhzad | C12N 15/111 |

OTHER PUBLICATIONS

Rejman et al., “mRNA transfection of cervical carcinoma and mesenchymal stem cells mediated by cationic carriers”, Journal of Controlled Release, vol. 147, No. 3, Nov. 2010, pp. 385-391.
Tavernier et al., “mRNA as gene therapeutic: How to control protein expression”, Journal of Controlled Release, vol. 150, No. 3, Mar. 2011, pp. 238-247.
International Search Report and Written Opinion of the ISA for PCT/EP2019/079742 mailed Jan. 15, 2020, 14 pages.
Tavernier et al., “mRNA as gene therapeutic: How to control protein expression”, Journal of Controlled Release, vol. 150, No. 3, Mar. 2011, pp. 238-247—Submission Pending.
Rejman et al., “mRNA transfection of cervical carcinoma and mesenchymal stem cells mediated by cationic carriers”, Journal of Controlled Release, vol. 147, No. 3, Nov. 2010, pp. 385-391—Submission Pending.

* cited by examiner (I)

Uncleaved HPRT-1 band: 1083 bp

Cleaved HPRT-1 bands: 827 and 256 bp

COMPOSITIONS FOR TRANSFECTING mRNA INTO A CELL AND THEIR APPLICATIONS

This application is the U.S. national phase of International Application No. PCT/EP2019/079742 filed Oct. 30, 2019 which designated the U.S. and claims priority to EP patent application Ser. No. 18306417.9 filed Oct. 30, 2018, the entire contents of each of which are hereby incorporated by reference.

BACKGROUND OF THE INVENTION

Field of the Invention

The present invention relates to compositions for transfecting a messenger RNA (mRNA) into a cell and their applications. The present invention is directed to a composition for transfecting a mRNA into a cell comprising a mRNA, at least one neutral lipid and a cationic lipid of formula (I), wherein $R_1$ $R_2$, $R_3$, $R_4$ and $R_5$, $(CH_2)_n$ and $A^-$ are as defined in the description. The present invention also relates to uses of said composition and to a method for in vitro transfection of live cells.

Description of the Related Art

The introduction of genetic material into cells is of fundamental importance to developments in modern biology and medicine, and has provided much of our knowledge of gene function and regulation. In nearly all cases DNA has been used for transfection purposes because of its inherent stability and its ability to integrate into the host genome to produce stable transfectants. A wide variety of methods are available to introduce genetic material into cells. These include simple manipulations such as mixing DNA with calcium phosphate, DEAE-dextran, polylysine, or carrier proteins. Other methods involve microinjection, electroporation, protoplast fusion, liposomes, gene-gun delivery, cationic polymers and viral vectors, to mention some.

Transfection of plasmid DNA is the easiest and the most common method to overexpress proteins in cells grown in culture. When it fails, the transfection reagent is generally recognized as the culprit, or the cells are simply considered as "hard-to-transfect."

However, not DNA uptake/delivery, but rather its processing once inside the cell might be the major limitation of the technique. Reaching and penetrating the nucleus, transcription and release of mRNA to the cytosol before final translation into protein are all critical steps.

A major problem involving cell transfection using current cationic polymer gene carriers is the relative high cytotoxicity encountered while approaching the desired transfection efficiency.

Transfecting cells with mRNA sequences rather than plasmid DNA constructs gives then a great chance to significantly increase transient protein expression levels in a majority of cell types, and offers a unique alternative for challenging cells.

Transfected mRNA does not need to reach the nucleus for cellular action. Translation occurs through a promoter-independent process and the desired protein is detectable as early as 6 h post-transfection.

The introduction of mRNA into mammalian cells using a transfection step was previously described in 1989 (Malone et al., 1989) but the use of mRNA was very limited for a long time because of its lack of stability. Another problem is that exogenous mRNA is immunogenic and induces strong immune responses (Heil et al., 2004; Kariko et al., 2004) through recognition by Toll-like receptors (TLRs). However, appropriate chemical modifications of nucleosides can reduce the immune activation as well as the mRNA degradation. It was shown that RNA containing 5-methylcytidine, $N^6$-methyladenosine, 5-methyluridine, pseudo-uridine or 2-thiouridine can reduce very efficiently the TLR activation (Kariko et al., 2005). It was also reported that the purification of in vitro transcribed mRNA containing modified nucleosides by HPLC is a powerful method to remove RNA-based contaminants which can be immunogenic. Consequently, the improved quality of mRNA inhibits the immune activation and enhances significantly the translation efficiency (Kariko et al., 2011).

In recent years, the use of transfected mRNA to produce a desired protein has become more popular. The transient character of expression is attractive and well suitable for many applications where the production of an intracellular protein or peptide as well as the expression of membrane or secreted protein is necessary. As example, the reprogramming of somatic cells into induced pluripotent stem cells (iPSCs) after delivery of mRNAs encoding transcription and reprogramming factors was shown to be very effective. This process is safer compared to a viral approach as this is a non-integrative approach in the genome (Yoshioka et al., 2013; Warren et al., 2010). The differentiation of stem cells into somatic cells can be also achieved after mRNA delivery where the transient and fast expression of differentiation factors is required for this application. The introduction of mRNA or long RNA, such as genomic viral RNA, into producer cells is also of interest to produce recombinant proteins, antibodies or recombinant viruses.

The genome editing technology is widely used to introduce site-specific modifications (genome engineering) into the genome of cells, including corrections or introductions of mutations, deletions, or gene replacement. The genome modification can be achieved through the use of endonucleases such as zinc-finger nucleases (ZFN), transcription activator-like effector nucleases (TALEN), and clustered regularly interspaced short palindromic repeat-associated system (CRISPR/Cas). The RNA-guided DNA endonucleases such as the Cas9 proteins are very effective to modify the genome (Doudna and Charpentier, 2014). The CRISPR-Cas 9 system combines a specific DNA target sequence recognition into the genome through a Watson-Crick base pairing with a single guide RNA (sgRNA) followed by a distinct protospacer-adjacent motif (PAM), the Cas9 binding and cleavage of the target sequence resulting in a double-stranded break in the DNA target (Ran et al., 2013). The double-stranded DNA break is detected by the repair system and is repaired through a non-homologous end joining (NHEJ) or a homology-directed repair (HDR) event. NHEJ results in a permanent insertion or deletion into the genome whereas the HDR requires the presence of a DNA template leading to the incorporation through homologous recombination of the template into the genome. All the components of CRISPR-Cas9 have to be introduced in the cells, including sgRNA, the Cas9 protein and a donor DNA template, in case of HDR. The Cas9 protein is directly introduced in the cells or encoded by DNA plasmid or mRNA (Ran et al., 2013). The approach using mRNA is very attractive as the expression of Cas9 is very transient with no risk of genomic integration avoiding a stable long-term expression and the risk of off-target events of genome modification.

The mRNA-based gene transfer is becoming a promising therapeutic approach (Yamamoto et al., 2008, Tavernier et al., 2011). One of the most developed approaches using mRNA is the vaccination against viral infections and cancers through direct administration. The efficient delivery of mRNAs encoding antigens into immune cells in vivo, particularly in antigen presenting cells such as dendritic cells, was reported and was shown to induce the expression of the encoded antigen, the antigen presentation, and a humoral or cellular immune response. The expression of antigen on tumoral cells after mRNA delivery is also a novel immunotherapy approach. The mRNA transfer into muscles can lead to the production of secreted antigens inducing a specific immune response. For vaccination purposes, the immune activation by the IVT (in vitro transcription technology) of mRNA itself can be beneficial and can be modulated by the nucleoside modifications. Many mRNA-based vaccines are now under evaluation in clinical trials (Kaczmarek et al., 2017). Many approaches tested in clinic are based on an adoptive transfer of dendritic cells ex vivo transfected with mRNAs coding for specific antigens or immunomodulators. Intramuscular of naked mRNA is currently used to trigger a RNA-based vaccination. Recently, systemic applications of therapeutic mRNAs are developed to target lungs, liver or tumors with a delivery mediated by viral or non-viral vectors, such as lipid nanoparticles.

For non-immunotherapy-related applications such as protein replacement for genetic disorders, the IVT mRNA-mediated immune activation has to be reduced as much as possible to avoid the cell death through the activation of interferon pathway. Kormann et al. have investigated the therapeutic potential of modified mRNA in the lung, using a mouse model of a hereditary disease, congenital surfactant protein B (SP-B) deficiency. Local repeated intranasal administration of an aerosol with SP-B mRNA resulted in high-level of SP-B expression and survival of treated animals with a low level of immune activation (Kormann et al., 2011). These results were obtained by 25% replacements of uridine and cytidine contained in the mRNA sequence by s2U and m5C, respectively. Systemic expression of erythropoietin protein (EPO) in mice was achieved by injection of EPO mRNA through intramuscular (Kormann et al., 2011) and intraperitoneal administration (Kariko et al., 2012) using 25% or 100% replacement of uridine and cytidine nucleobases, respectively.

The efficient introduction of mRNA into cells require a reagent, composition or formulation of transfection. These products are generally cationic systems which are able to interact or complex the mRNA via electrostatic binding. Then they are able to interact with plasma membranes and induce the mRNA transport through the cell membrane or through an endocytosis process. Cationic lipid or polymer systems are mainly used. Most of them contain protonable amines in acidic conditions or fusogenic lipid promoting an endosomal release of mRNA in the cytoplasm through endosomolysis or endosomal membrane destabilization. Suitable cationic polymers (review in Kaczmarek et al., 2017) are polyethyleneimine (PEI), polylysine, polyornithine, polyamidoamine, poly(beta-amino esters) or oligoalkylamines (Jarzebinska et al., 2016). Many derivatives of cationic polymers such as cyclodextrin-PEI (Li et al., 2017), stearic acid-PEI (Zhao et al., 2016), aromatic-PEI (Chiper et al., 2017) or histidinyl-PEI (Goncalves et al., 2016) were reported for mRNA transfection. Many commercially cationic lipid formulations having a net positive charge at physiological pH to electrostatically bind mRNA are available and were reported to efficiently carry mRNA in cells such as Lipofectamine Messenger Max, Lipofectamine RNAiMax or Lipofectamine 2000 from Thermo Fisher Scientific, TransIT-mRNA from Mirus Bio or StemFect from Stemgent. Cationic lipids seem to be more efficient than cationic polymers such as PEI to deliver mRNA into cells as reported by Rejman et al., 2010, De Haes et al., 2013. However, toxicity and immune response may be associated with cationic lipid transfection as described by Drews et al., 2012, when they have used Lipofectamine RNAiMax to transfect mRNAs encoding reprogramming factors for the generation of iPS cells. Such side effects may limit the use of many cationic lipids for in vivo applications.

U.S. Pat. No. 7,479,573 describes a cationic compound having the formula:

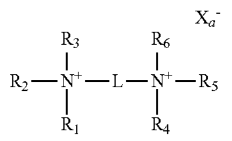

wherein

L is $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group, and wherein a carbon of $(CH_2)_i$ or a carbon of $(CH_2)_j$ is optionally substituted with —OH;

$R_1$ and $R_4$ are, independently, a straight-chain, branched or cyclic alkyl or alkenyl groups having from 8 to 40 carbon atoms;

$R_3$ and $R_6$ are, independently, H an alkyl or an alkenyl group;

$R_2$ is an aminoalcohol group;

$R_5$ is H or an aminoalcohol group;

X is a physiologically acceptable anion; and a is the number of positive charges divided by the valence of the anion;

i and j are independently an integer from 0 to 100;

k is an integer from 1 to 25, and wherein at least one of $R_1$ or $R_4$ is a straight-chain, branched or cyclic alkyl or alkenyl group having from 8 to 40 carbon atoms.

The above cationic compound is known by its tradename of Lipofectamine®. It is a cationic liposome formulation, which is formulated with a neutral co-lipid (helper lipid) (Dalby B, et al. *Methods.* 33 (2): 95-103).

The DNA-containing liposomes (with positive charge on their surfaces) can fuse with the negatively charged plasma membrane of living cells, due to the neutral co-lipid mediating fusion of the liposome with the cell membrane, allowing nucleic acid to cross into the cytoplasm and contents to be available to the cell for replication or expression.

U.S. Pat. No. 5,627,159 describes a method of transfecting an animal cell in the presence of serum, comprising contacting said cell with a lipid aggregate comprising nucleic acid and a cationic lipid, wherein the improvement comprises: contacting said cell with said lipid aggregate in the presence of a polycationic compound, thereby transfecting said animal cell with said nucleic acid, or contacting said lipid aggregate with said polycation compound to form a mixture followed by contacting said cell with said mixture, thereby transfecting said animal cell with said nucleic acid.

In U.S. Pat. No. 8,399,422, compositions are described for transfection of siRNA comprising an oligonucleotide and a cationic amphiphilic molecule having the formula I

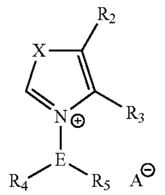

wherein X is N—$R_1$, S or O, $R_1$ being a $C_1$-$C_4$ alkyl radical or an hydroxylated $C_3$-$C_6$ alkyl radical; $R_2$ and $R_3$, identical or different, represent H or a $C_1$-$C_4$ alkyl radical, or $R_2$ and $R_3$ are linked together to form a saturated or unsaturated cyclic or an heterocycle having 5 or 6 elements; E is a $C_1$-$C_5$ alkyl spacer; $R_4$ and $R_5$, identical or different, represent a saturated or unsaturated linear or branched $C_{10}$-$C_{36}$ hydrocarbon or fluorocarbon chains, said chains optionally comprising $C_3$-$C_6$ cycloalkyl; $A^-$ is a biocompatible anion. The heterocycles formed when $R_2$ and $R_3$ are linked together are saturated or unsaturated and have 5 or 6 elements and comprise C, S or O.

This U.S. Pat. No. 8,399,422 requires that the composition contains an oligonucleotide and are used for siRNA interference.

Small interfering RNAs (siRNAs) have a well-defined structure consisting of a short double-stranded RNA (usually from 20 to 25 base pairs in length).

Unlike siRNAs, mRNAs are single-stranded, may have locally a variable or complex structure (including secondary structures such as paired regions, unpaired regions, end- or centered-loops) and have a high molecular weight corresponding to long molecules when compared to siRNA. Mature eukaryotic mRNA furthermore consists of the 5'-cap structure (m7GpppN or m7Gp3N), the 5' untranslated region (5'UTR), the open reading frame (ORF) encoding a protein or a peptide, the 3' untranslated region (3'UTR) and the polyadenosine tail (100 to 250 adenosine residues).

SUMMARY OF THE INVENTION

Thus, it is an object of the present invention to provide a more efficient transfection formulation for transfecting mRNA.

It is another object of the present invention to provide a method for transfecting mRNA using said formulation.

The present invention relates to a composition suitable for transfecting a messenger RNA (mRNA) into a cell, in particular a mammalian cell, preferably a human cell, comprising a mRNA, at least one neutral lipid and a cationic lipid of formula (I):

(I)

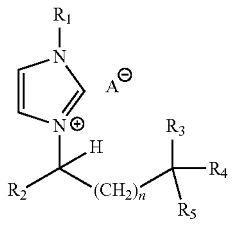

wherein $R_1$ represents a $C_1$-$C_4$ hydrocarbon chain or a $C_1$-$C_4$ hydroxylated chain;

$R_2$, $R_3$, $R_4$ and $R_5$, which may be identical or different, represent H; a $C_6$-$C_{33}$ saturated or unsaturated, linear or branched hydrocarbon chain; or a saturated or unsaturated $C_6$ cycle;

$(CH_2)_n$ represents a hydrocarbon chain linker with n representing an integer between 0 and 4 inclusive;

$A^-$ represents a biocompatible anion.

The composition of the invention is a cationic composition, in particular a cationic liposomal composition, which is able to interact with negatively charged DNA and cell membranes. The cationic lipids are stably formulated as small sized liposomes with the neutral lipids. The ratio of cationic lipids and neutral lipids in the cationic composition, in particular the cationic liposomes, modulates the surface charge density of the composition, in particular of the cationic liposomes. When liposomes are formed, the structure of neutral lipids modulates the lamellar structure, the lipid bilayer rigidity of cationic liposomes as well as the fusogenic activity with cell membranes which is involved in endosomal escape after the endocytosis of lipoplexes (nucleic acid/cationic liposome complexes). The formed liposomes may have an average size ranging from 50 nm to 200 nm, preferably have an average size of 100 nm.

In a particular embodiment of the invention, the at least one neutral lipid includes any triglycerides which consist of three fatty acids attached to a glycerol molecule. Preferably the at least one neutral lipid is selected from the group consisting of phosphatidylserine (PS), phosphatidylcholine (PC), phosphatidylinositol (PI) derivatives, lipid-PolyEthyleneGlycol (PEG) conjugates, cholesterol derivatives and phosphatidylethanolamine derivatives such as 1,2-Dioleoyl-sn-glycero-3-phosphoethanolamine (DOPE), 1,2-diphenytanoyl-sn-glycero-3-phosphoethanolamine (DPyPE), palmitoyl linoleoyl phosphatidylethanolamine (PaLiPE), dilinoleoyl phosphatidylethanolamine (DiLiPE), phosphatidylethanolamine (PE). The composition of the invention may comprise at least two, at least three or at least four neutral lipids, preferably at least two or three neutral lipids selected from the group consisting of DPyPE, DOPE, cholesterol and lipid-PEG conjugates. Preferably the at least one neutral lipid is DOPE or DPyPE, more preferably is DPyPE. The at least one neutral lipid can thus be a single neutral lipid.

In a particular embodiment of the invention in formula (I), $(CH_2)_n$ represents a hydrocarbon chain linker with n representing an integer between 2 and 4 inclusive, preferably n=4, and $R_2$ represents a $C_6$-$C_{33}$ saturated or unsaturated, linear or branched hydrocarbon chain; or a saturated or unsaturated $C_6$ cycle.

In another particular embodiment of the invention, $(CH_2)_n$ represents a hydrocarbon chain linker with n representing an integer between 2 and 4 inclusive, and $R_1$ represents a $C_1$, $C_2$ or $C_4$ hydrocarbon chain or a $C_2$ hydroxylated chain, preferably n=4 and $R_1$ represents a $C_1$ or a $C_4$ hydrocarbon chain.

In a particular embodiment of the invention, $R_1$, $R_2$, $R_3$, $R_4$ and $R_5$ are different. In a particular embodiment, at least 4, at least 3 or at least 2 compounds selected from the group consisting of $R_1$, $R_2$, $R_3$, $R_4$ and $R_5$ are different. Preferably, $R_1$ and $R_3$ are different, $R_1$ and $R_5$ are different, $R_2$ and $R_3$ are different, $R_2$ and $R_4$ are different, $R_3$ and $R_4$ are different, $R_4$ and $R_5$ are different.

In another particular embodiment of the invention, $R_2$, $R_3$, $R_4$ and $R_5$ are identical. In another particular embodiment, at least 4, at least 3 or at least 2 compounds selected from the group consisting of $R_1$, $R_2$, $R_3$, $R_4$ and $R_5$ are identical. Preferably, $R_2$, $R_3$ and $R_4$ are identical, $R_2$ and $R_4$ are identical, $R_3$ and $R_5$ are identical, or $R_3$ and $R_4$ are identical.

In a preferred embodiment of the invention, $(CH_2)_n$ represents a hydrocarbon chain linker with n representing an integer between 2 and 4 inclusive, preferably n=4, and $R_1$ represents $CH_3$ or $C_4H_9$.

In another preferred embodiment of the invention, $(CH_2)_n$ represents a hydrocarbon chain linker with n representing an integer between 2 and 4 inclusive, preferably n=4, and $R_2$, $R_3$ or $R_4$ represents a $C_{10}$-$C_{18}$ saturated or unsaturated, linear or branched hydrocarbon chain, preferably a $C_{10}$, $C_{14}$ or $C_{18}$ saturated or unsaturated, linear or branched hydrocarbon chain.

In another preferred embodiment of the invention, $(CH_2)_n$ represents a hydrocarbon chain linker with n representing an integer between 2 and 4 inclusive, preferably n=4, and $R_5$ represents H.

In another preferred embodiment of the invention, $(CH_2)_n$ represents a hydrocarbon chain linker with n representing an integer between 2 and 4 inclusive, preferably n=4, $R_1$ represents $CH_3$ or $C_4H_9$, $R_2$, $R_3$ or $R_4$ represents a $C_{10}$-$C_{18}$ saturated or unsaturated, linear or branched hydrocarbon chain, preferably a $C_{10}$, $C_{14}$ or $C_{18}$ saturated or unsaturated, linear or branched hydrocarbon chain and $R_5$ represents H.

In a particular embodiment of the invention, $(CH_2)_n$ represents a hydrocarbon chain linker with n=0; $R_1$ represents $CH_3$; $R_2$ represents H or a $C_{14}$-$C_{18}$ saturated or unsaturated alkyl chain; $R_3$ represents H or a $C_{17}H_{35}$ saturated alkyl chain; $R_4$ represents a $C_9$-$C_{17}$ saturated or unsaturated alkyl chain and $R_5$ represents H. Said cationic lipid contains two lipophilic chains. Said cationic lipid is formulated in a composition with at least one neutral lipid as defined herein, in particular with DOPE or DPyPE, preferably with DPyPE. Said composition may also comprise a mRNA as defined herein, in particular a capped mRNA, preferably a mRNA capped with a cap 0 or a cap 1 structure or a mRNA which is further 3'-end polyadenylated and/or contains modified nucleotides such as 5-methylcytidine and pseudo-uridine.

In a preferred embodiment of the invention, $(CH_2)_n$ represents a hydrocarbon chain linker with n=4, $R_1$ represents $CH_3$, $R_2$ represents a $C_6$-$C_{33}$ saturated or unsaturated, linear or branched hydrocarbon chain; or a saturated or unsaturated $C_6$ cycle, preferably $R_2$ represents a $C_{10}H_{21}$ branched alkyl chain; $R_3$ and $R_4$ represent a $C_{14}$-$C_{18}$ saturated or unsaturated alkyl chain and $R_5$ represents H. Said cationic lipid contains a ramified structure having three lipophilic chains. Said cationic lipid is formulated in a composition with at least one neutral lipid as defined herein, in particular with DOPE or DPyPE, preferably with DPyPE. Said composition may also comprise a mRNA as defined herein, in particular a capped mRNA, preferably a mRNA capped with a cap 0 or a cap 1 structure or a mRNA which is further 3'-end polyadenylated and/or contains modified nucleotides such as 5-methylcytidine and pseudo-uridine.

In another preferred embodiment of the invention, $(CH_2)_n$ represents a hydrocarbon chain linker with n=4, $R_1$ represents $CH_2$—$CH_2$—$CH_2$—$CH_3$, $R_2$, $R_3$ and $R_4$ represent a $C_{10}$-$C_{18}$ saturated or unsaturated alkyl chain, and $R_5$ represents H. Said cationic lipid contains a ramified structure having three lipophilic chains. Said cationic lipid is formulated in a composition with at least one neutral lipid as defined herein, in particular with DOPE or DPyPE, preferably with DPyPE. Said composition may also comprise a mRNA as defined herein, in particular a capped mRNA, preferably a mRNA capped with a cap 0 or a cap 1 structure or a mRNA which is further 3'-end polyadenylated and/or contains modified nucleotides such as 5-methylcytidine and pseudo-uridine.

In another preferred embodiment of the invention, $(CH_2)_n$ represents a hydrocarbon chain linker with n=4, $R_1$ represents hydroxyethyl or ethyl, $R_2$, $R_3$ and $R_4$ represent a $C_{14}$-$C_{18}$ saturated or unsaturated alkyl chain, and $R_5$ represents H. Said cationic lipid contains a ramified structure having three lipophilic chains. Said cationic lipid is formulated in a composition with at least one neutral lipid as defined herein, in particular with DOPE or DPyPE, preferably with DPyPE. Said composition may also comprise a mRNA as defined herein, in particular a capped mRNA, preferably a mRNA capped with a cap 0 or a cap 1 structure or a mRNA which is further 3'-end polyadenylated and/or contains modified nucleotides such as 5-methylcytidine and pseudo-uridine.

In another preferred embodiment of the invention, $(CH_2)_n$ represents a hydrocarbon chain linker with n=2 or 3, $R_1$ represents $CH_3$, $R_2$ represents H or a $C_{18}$ saturated alkyl chain, $R_3$ and $R_4$ represent a $C_{14}$-$C_{16}$ saturated alkyl chain, and $R_5$ represents H. Said cationic lipid contains two lipophilic chains or a ramified structure having three lipophilic chains. Said cationic lipid is formulated in a composition with at least one neutral lipid as defined herein, in particular with DOPE or DPyPE, preferably with DPyPE. Said composition may also comprise a mRNA as defined herein, in particular a capped mRNA, preferably a mRNA capped with a cap 0 or a cap 1 structure or a mRNA which is further 3'-end polyadenylated and/or contains modified nucleotides such as 5-methylcytidine and pseudo-uridine.

The cationic lipid of formula (I), which is an imidazolium-based cationic lipid (FIG. 1), has been identified by the inventors following a structure activity screening.

As defined herein, the term "imidazolium" refers to an organic compound containing the cationic form by protonation of imidazole in which two of the five atoms that make up the ring are nitrogen atoms.

In a particular embodiment of the invention, the cationic lipid of formula (I) is selected from the group consisting of the following compounds:

W1.4

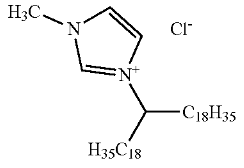

W2.5

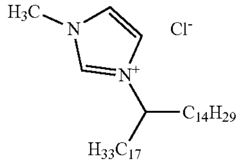

W3.5

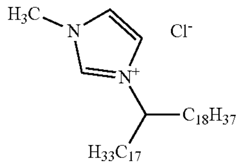

-continued
W4.3
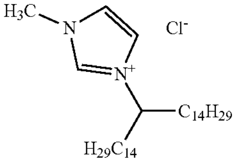
W5.3
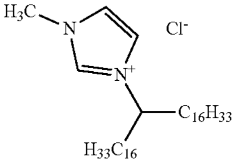
W6.3
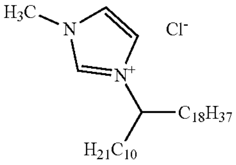
W7.4
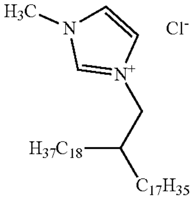
W8.7
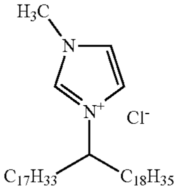
W9.7
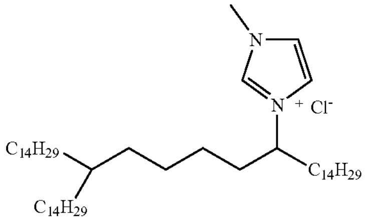
W10.7
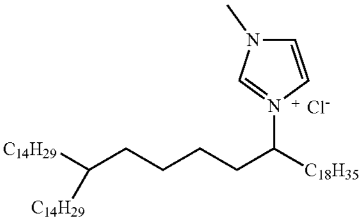
W11.7
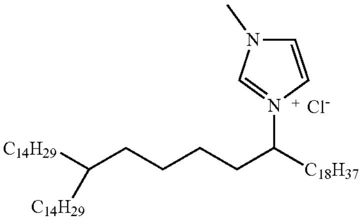
-continued
W12.7
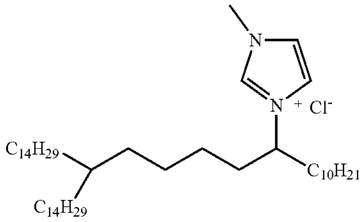
W13.7
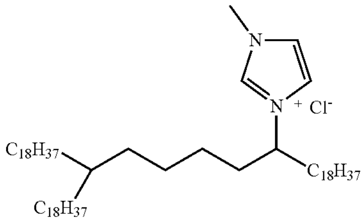
W14.7
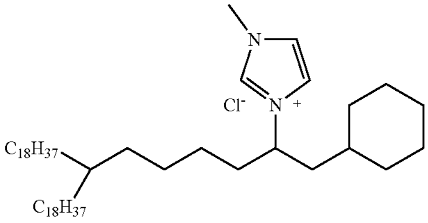
W15.7
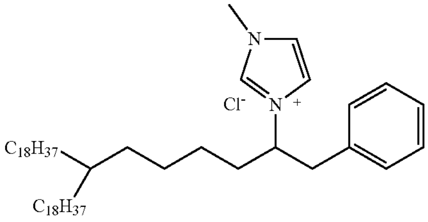
W16.7
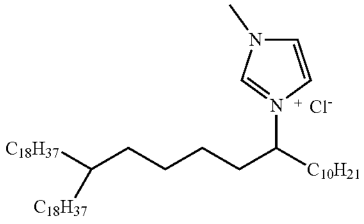
W17.7
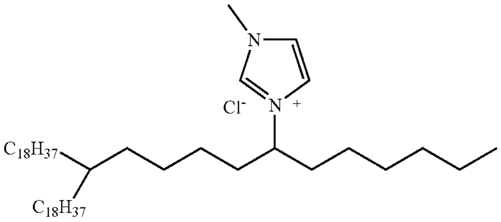

-continued
W18.9
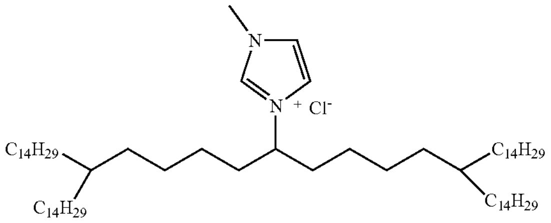
W19.7
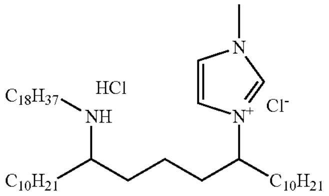
W20.7
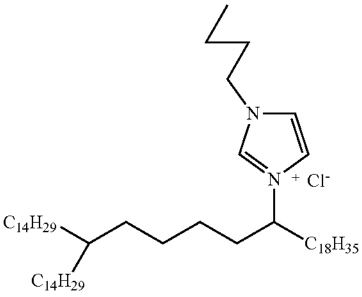
W21.7
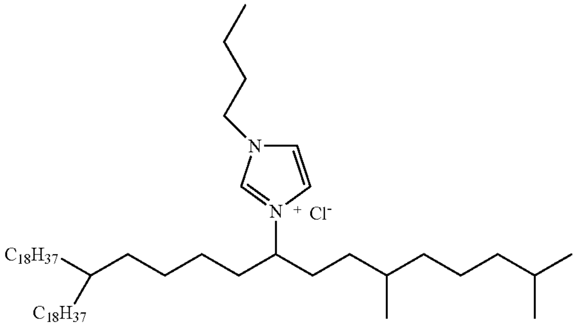
W22.7
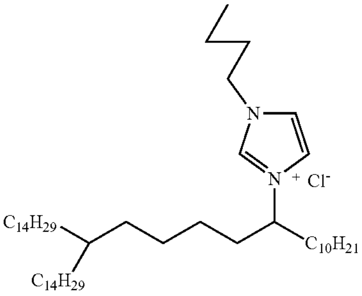
-continued
W23.7
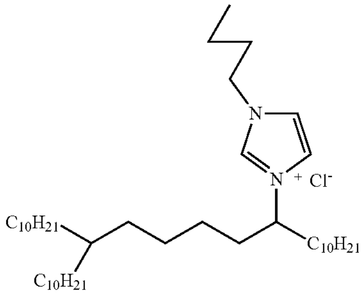
W25.7
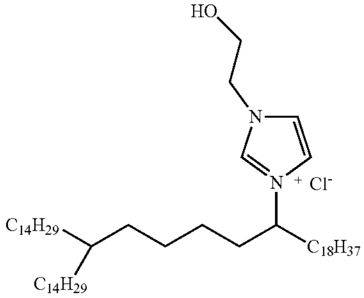
W26.7
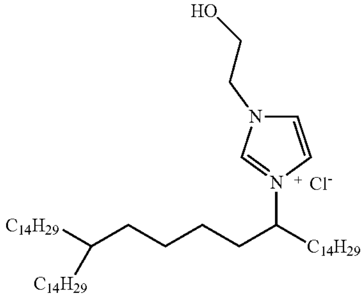
W27.7
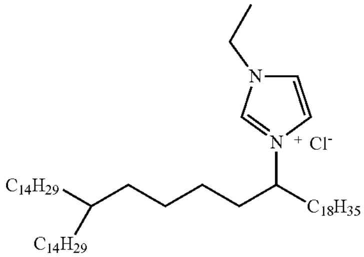
W28.7
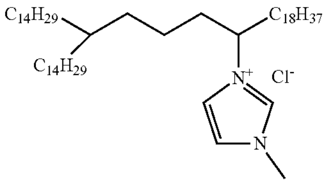
W29.5
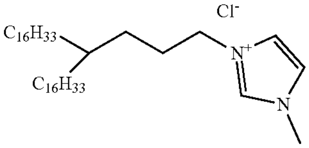
In a preferred embodiment of the invention, the cationic lipid of formula (I) is selected from the group consisting of the following compounds:

-continued
W9.7
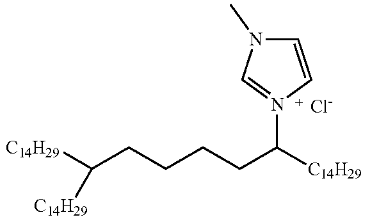
W10.7
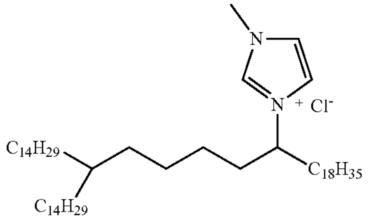
W11.7
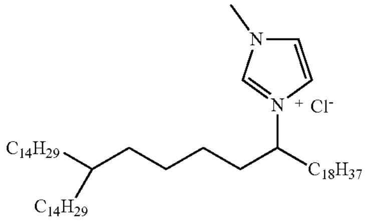
W12.7
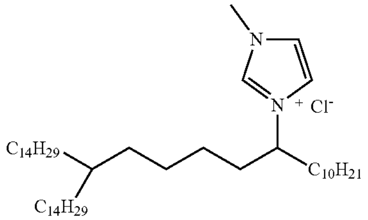
W13.7
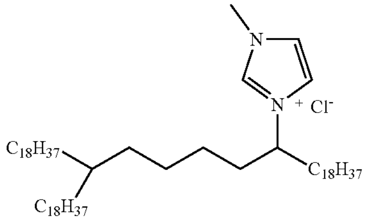
W14.7
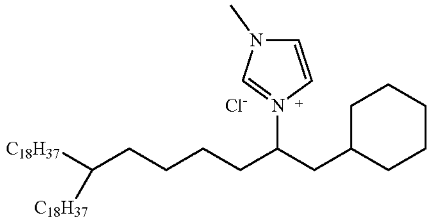
W15.7
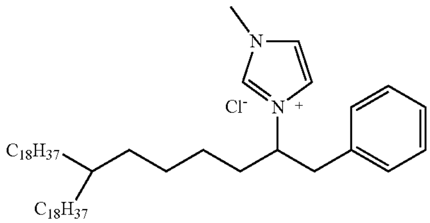
W16.7
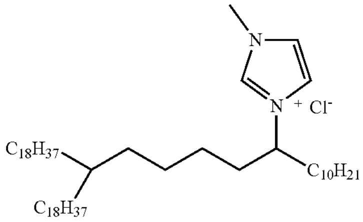
W17.7
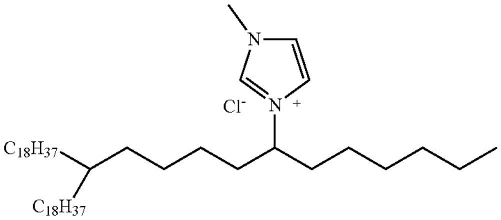
W18.9
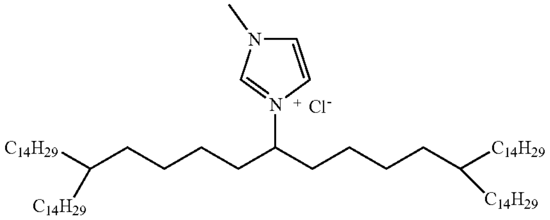
W19.7
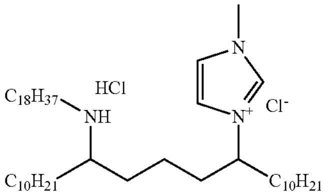
W20.7
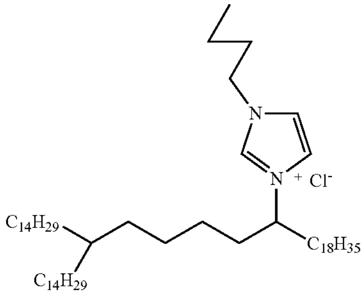
W21.7
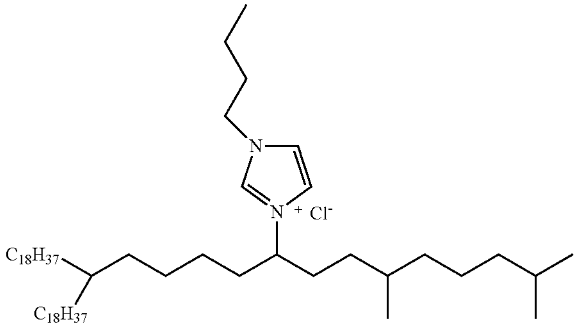

-continued
W22.7
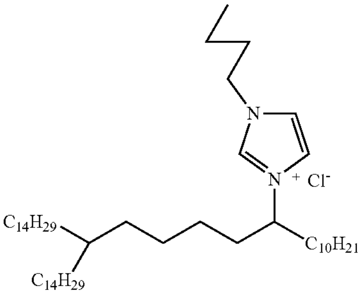
W23.7
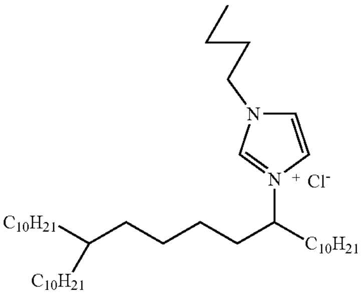
W25.7
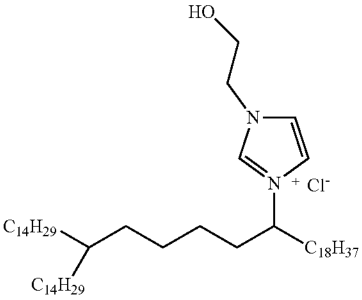
W26.7
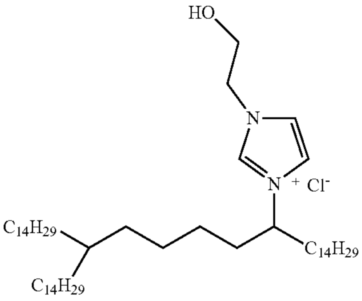
W27.7
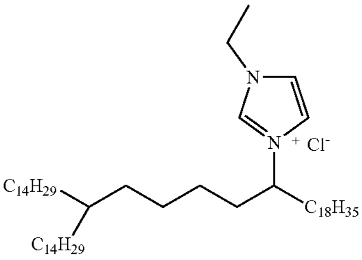
-continued
W28.7
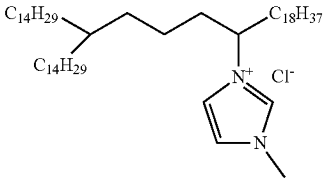
W29.5
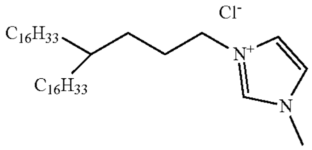
In a preferred embodiment of the invention, the cationic lipid of formula (I) is selected from the group consisting of the following compounds:
W12.7
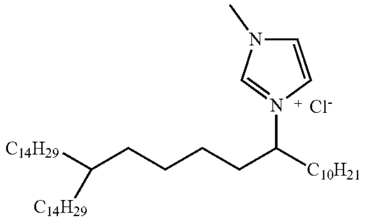
W20.7
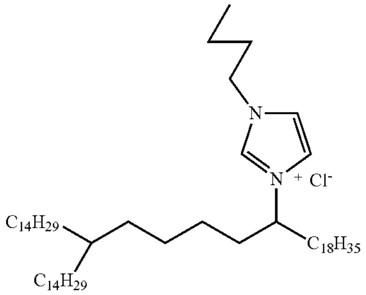
W21.7
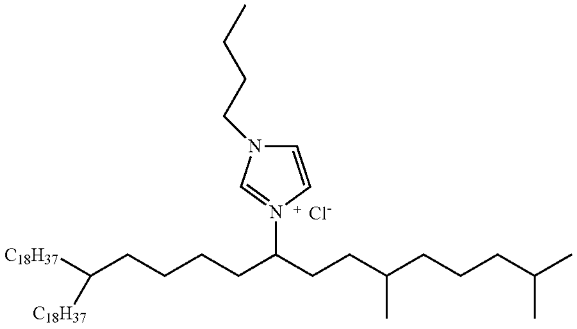

-continued

W22.7

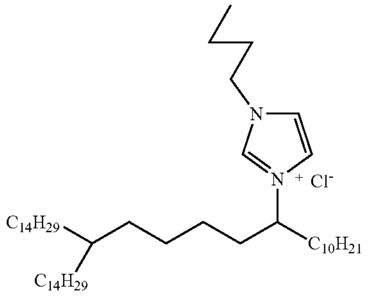

In a particular embodiment of the invention, the above selected particular cationic lipids are selected in the group of W9.7, W10.7, W11.7, W12.7, W13.7, W14.7, W15.7, W16.7, W17.7, W18.9, W19.7, W20.7, W21.7, W22.7, W23.7, W25.7, W26.7, W27.7, W28.7 and W29.5, or in the group of W12.7, W20.7, W21.7 and W22.7, and are associated in the composition with the neutral lipid DOPE or DPyPE, preferably with DPyPE.

In a particular embodiment of the invention, $A^-$ represents $Cl^-$ or $OH^-$. $A^-$ is a biocompatible anion naturally present in biological systems and is thus compatible with transfection.

In a particular embodiment of the invention, the molar ratio of the cationic lipid of formula (I) to the at least one neutral lipid ranges from 1:1 to 1:2, preferably is 1:1.5.

In a particular embodiment of the invention, the molar ratio of the mRNA to the cationic lipid and the at least one neutral lipid ranges from 1:2 to 1:20, preferably is 1:5, 1:10 or 1:15.

In a particular embodiment of the invention, the mRNA is a eukaryotic mRNA, in particular a mRNA encoding a protein of a mammal, especially a human protein.

In a particular embodiment of the invention, the 5'-end of the eukaryotic mRNA is capped. This allows the creation of stable and mature messenger RNA able to undergo translation during protein synthesis. Preferably the 5'-end of the mRNA is capped with a 7-methyl guanosine structure, a cap structure analogs such as Anti-Reverse Cap Analog (ARCA), a cap 0 structure including a 7-methylguanylate cap, a cap 1 structure including a 7-methylguanylate cap and a methylated 2'-hydroxy group on the first ribose sugar, or a cap 2 structure including a 7-methylguanylate cap ($m^7G$) and methylated 2'-hydroxy groups on the first two ribose sugars.

The sourcing of mRNA suitable for effective transfection has been a concern until improvement of the in vitro transcription technology (IVT) that is now an effective method to provide mRNA of good quality and fidelity from DNA templates. Sufficient amount of mRNA can be produced by many cost-effective commercially available kits. In addition, post-transcriptional modifications can be achieved by enzymatic reaction to incorporate 5'-end capping and 3'-end polyadenylation. For the purpose of the invention such in vitro synthesis technology may thus be used to reproduce mature eukaryotic mRNA such as mRNA consisting of optionally the cap structure (with the cap as defined herein, in particular m7GpppN or m7Gp3N), the 5' untranslated region (5'UTR), the open reading frame (ORF) encoding a protein or a peptide, the 3' untranslated region (3'UTR) and optionally the polyadenosine tail (100 to 250 adenosine residues).

As defined herein, the term "the mRNA is capped" refers to a 5' capping of eukaryotic mRNA with a Guanyl modification cap, which drastically increases the stability of RNA, and the loading into the ribosomes for the translation. In naturally produced mRNA providing a cap also improves the nuclear export after transcription of the mRNA in the cell nucleus. In the context of the invention, transfection of mRNA does not involve the export from the nucleus since transfected mRNA is provided directly to the cell cytoplasm. Capping may however be necessary or useful to ensure that mRNA reaches ribosome for translation. Accordingly capping is provided to the mRNA prior to its transfection in the cell where it is translated.

"0 capped or 1 capped or 2 capped" refers to the modification of the 5' end guanine in the nucleobases. Cap 0 refers to a 7-methylguanylate cap ($m^7G$ also designated as $m^7GpppN$), Cap 1 refers to a 7-methylguanylate cap ($m^7G$) and a methylated 2'-hydroxy group on the first ribose sugar giving rise to $m^7GpppNm$ modification, and Cap 2 refers to a 7-methylguanylate cap ($m^7G$) and methylated 2'-hydroxy groups on the first two ribose sugars giving rise to $m^7GpppNmpNm$ modification according to the known cap nomenclature.

In a particular embodiment of the invention, the mRNA, in particular the capped mRNA is further 3'-end polyadenylated and/or contains modified nucleosides. Modified nucleosides are in particular selected in order to improve the stability of the mRNA and/or prevent detrimental immune activation reaction against the mRNA when transfected into a host cell. Modified nucleosides can be included during the mRNA synthesis, and include for example 5-methoxyuridine, 2-thiouridine, 5-iodouridine, 5-bromouridine, 5-methylcytidine, 5-iodocytidine, 5-bromocytidine, 2-thiocytidine, pseudo-uridine, $N^6$-methyladenosine or $N^1$-methylguanosine to minimize immune response.

In a particular embodiment of the invention, the mRNA encodes (i) a peptide (having a length in amino acid resides of about 6 to 50 amino acid residues), in particular a peptide for use in vaccination such as tumor-associated antigens or viral antigens, (ii) an enzyme, in particular a nuclease such as an endonuclease (such as zinc-finger nucleases (ZFN) or transcription activator-like effector nucleases (TALEN) and clustered regularly interspaced short palindromic repeat-associated system (CRISPR/CAS)) or an exonuclease (illustration of nucleases is provided in the Examples with CAS9 protein), or (iii) defined through its purpose and function, a protein, in particular a therapeutic protein, more preferably a therapeutic protein to correct genetic disorders such as dystrophin, CFTR, human factor IX, a therapeutic protein against cancer such as a cytokine, an anti-oncogene, an antibody, in particular a blocking antibody, an anti-tumor suppressor or a toxin, a therapeutic protein with antiviral activity, in particular a therapeutic growth factor such as VEGF, FGF or HGF, or a therapeutic protein for immunotherapy, wherein the protein as thus defined encompasses a peptide or a polypeptide of especially more than 50 amino acid residues, and wherein the protein may be a human protein, in particular when it is a therapeutic protein, more preferably a therapeutic protein to correct genetic disorders, a therapeutic protein against cancer such as a cytokine, an anti-oncogene, an antibody, in particular a blocking antibody, an anti-tumor suppressor or a toxin, a therapeutic protein with antiviral activity or a therapeutic protein for immunotherapy; or a reporter protein such as fluorescent proteins (e.g. GFP), luminescent proteins (e.g. luciferase) or β-galactosidase, or (iv) reprogramming factors such as Oct4, SOX2, KLF4 or c-MYC, or the combination thereof.

In a particular embodiment of the invention, the cell for transfection is selected from the group consisting of a mammalian cell, an insect cell, a cell line, a primary cell, an adherent cell and a suspension cell.

As defined herein, the term “adherent cells” refers to cells that need solid support for growth, and thus are anchorage-dependent. Examples of adherent cells include MRC-5 cells, HeLa cells, Vero cells, NIH-3T3 cells, L293 cells, CHO cells, BHK-21 cells, MCF-7 cells, A549 cells, COS cells, HEK 293 cells, Hep G2 cells, SNN-BE(2) cells, BAE-1 cells and SH-SY5Y cells.

As defined herein, the term “suspension cells” refers to cells that do not need solid support for growth, and thus is anchorage-independent. Examples of suspension cells include NSO cells, U937 cells, Namalawa cells, HL60 cells, WEHI231 cells, Yac 1 cells, Jurkat cells, THP-1 cells, K562 cells and U266B1 cells.

In a particular embodiment of the invention, the composition further comprises a compound selected from the group consisting of (i) a distinct mRNA for co-transfection, (ii) a short non-coding RNA such as guide RNA, in particular a CRISPR guide RNA, a microRNA, a shRNA or a siRNA, and (iii) a long non-coding RNA allowing genetic and biological regulations.

In a particular embodiment of the invention, the first mRNA defined herein is encoding an enzyme such as a nuclease and is co-transfected with a guide RNA.

The present invention also relates to a mixture of compounds wherein the compounds comprise at least one neutral lipid and a cationic lipid selected from the group consisting of the following compounds, wherein the at least one neutral lipid and the cationic lipid are suitable for use in transfecting a messenger RNA (mRNA) into a cell:

W9.7

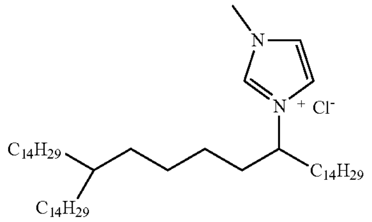

W10.7

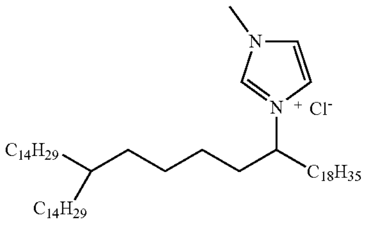

W11.7

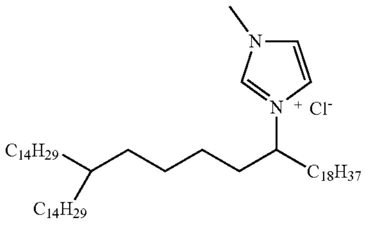

-continued

W12.7

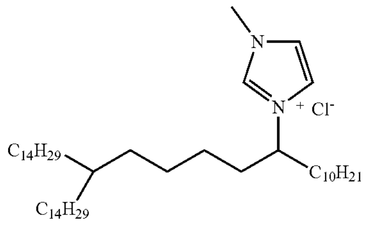

W13.7

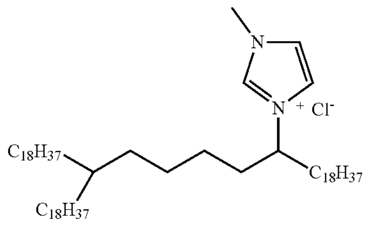

W14.7

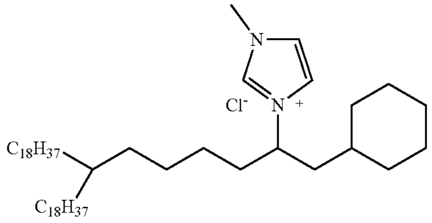

W15.7

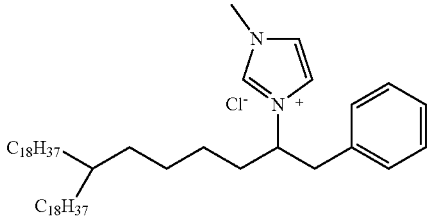

W16.7

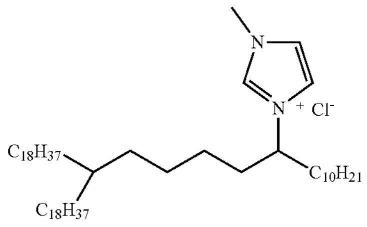

W17.7

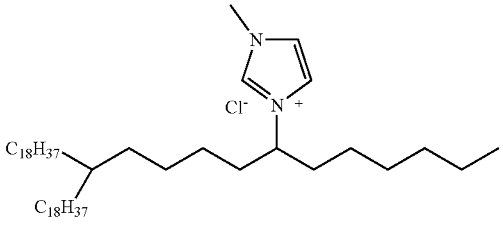

-continued
W18.9
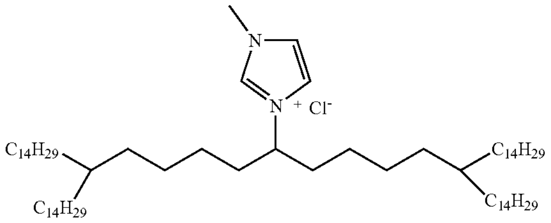
W19.7
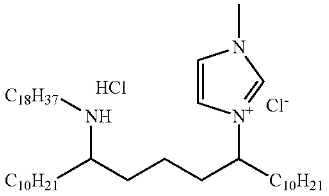
W20.7
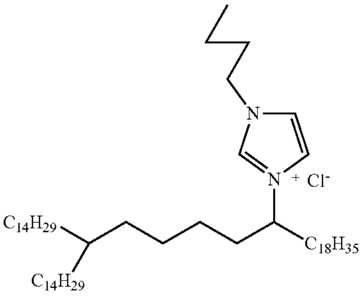
W21.7
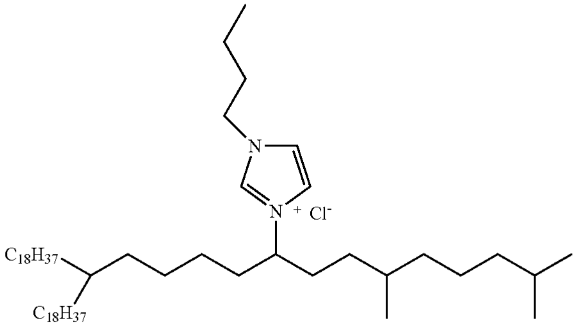
W22.7
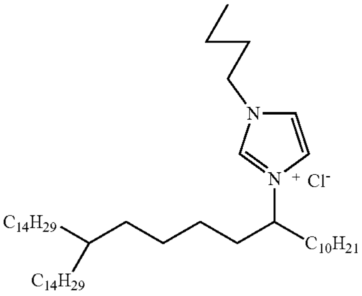
-continued
W23.7
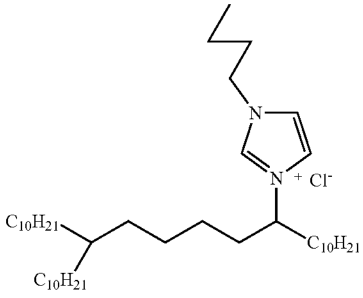
W25.7
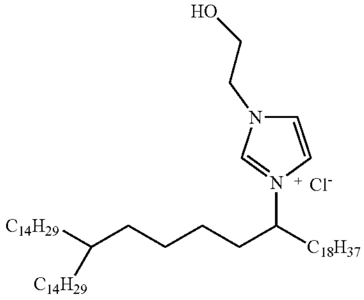
W26.7
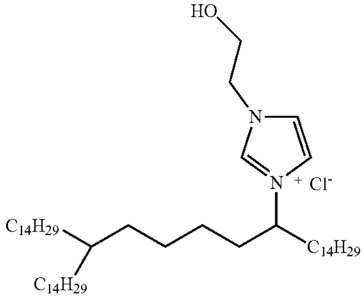
W27.7
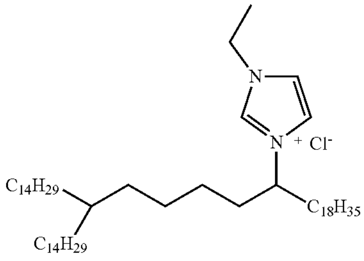
W28.7
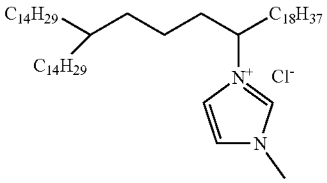
W29.5
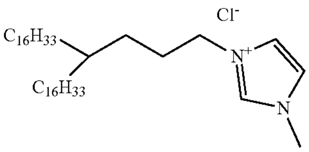
In a particular embodiment of the invention, said mixture of compounds suitable for transfecting a messenger RNA (mRNA) into a cell comprise at least one neutral lipid and a cationic lipid selected from the group consisting of the following compounds:

W12.7

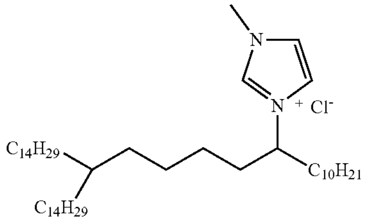

W20.7

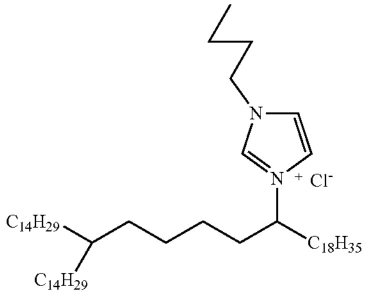

W21.7

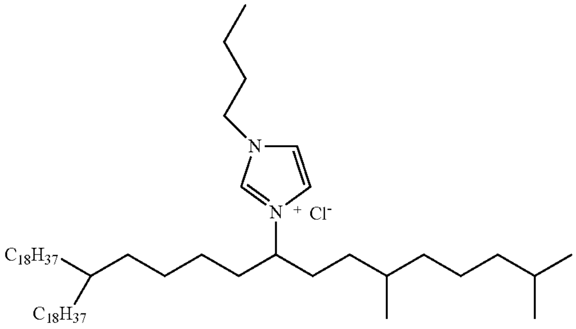

W22.7

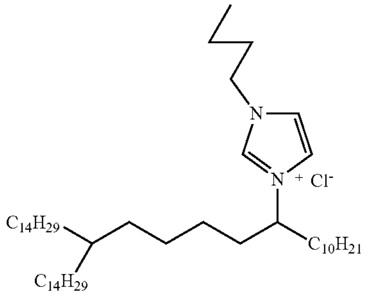

In a particular embodiment of the invention, the at least one neutral lipid used in said mixture of compounds is as defined herein and/or the molar ratio of the cationic lipid to the at least one neutral lipid ranges from 1:1 to 1:2, preferably is 1:1.5.

In a particular embodiment of the mixture of compounds comprising one of the above cationic lipid, the at least one neutral lipid is DOPE or DPyPE, preferably is DPyPE.

The present invention is also directed to the composition as defined herein for use as a therapeutic or prophylactic vaccine against viral infections, or a therapeutic vaccine against cancers. Generally, in this aspect, the vaccine is delivered through direct administration such as systemic, intramuscular, intradermal, intraperitoneal, intratumoral, oral, topical, or sub-cutaneous administration, and, in said vaccine, the composition is in association with a pharmaceutically acceptable vehicle. In other words, the vaccine can be injected directly into the body, in particular in a human individual, for inducing a cellular and/or a humoral response.

According to a particular embodiment of the invention, the composition hence comprises a pharmaceutically acceptable vehicle.

As defined herein, "a pharmaceutically acceptable vehicle" refers to any substance or combination of substances physiologically acceptable i.e., appropriate for its use in a composition in contact with a host, especially a human, and thus non-toxic. It can refer to a solid, semi-solid or liquid filler, diluent, encapsulating material or formulation auxiliary of any conventional type.

The present invention is also directed to the composition according to the invention for use in in vivo applications for mRNA-based therapy.

The present invention also concerns a method for in vitro transfection of live cells comprising introducing in the cells the composition according to the invention.

The present invention also relates to the use of the composition according to the invention to transfect a mRNA of said composition into a cell, preferably a mammalian cell, in particular a human cell, an insect cell. The target cell for transfection may be a cell line, a primary cell, an adherent cell or a suspension cell.

The present invention also relates to the use of the composition according to the invention for cell reprogramming, in particular for the reprogramming of differentiated cells into induced pluripotent stem cells (iPCs), for differentiating cells, for gene-editing or genome engineering. Such use may be carried out in a culture of cells in vitro or ex vivo for the production of biologics, for the preparation of cells for therapy purpose, or for the study of cell functions or behaviour in particular with a step of expansion of cells after their transfection or may be carried out in vivo for a therapeutic purpose in a host in need thereof.

The present invention also relates to the use of the composition according to the invention in the production of biologics encoding a protein, in particular a recombinant protein or an antibody, or in the production of recombinant virus, said composition further comprising a distinct mRNA or long RNA.

The composition according to the invention may be used as a formulation of the mRNA with the cationic lipids and the neutral lipids in accordance with the disclosure provided herein, in particular as a liposome formulation. It may alternatively be used as a cell culture or as expanded cells, wherein prior to being provided as a culture and/or as expanded cells, isolated cells have been treated with the formulation of the mRNA with the cationic lipids and the neutral lipids in accordance with the disclosure provided herein, in particular as a liposome formulation, for transfection. Otherwise stated, the composition of the invention encompasses, as an embodiment, a cell or a cell culture or expanded cells wherein the formulation of mRNA, cationic lipids and neutral lipids has been introduced by transfection according to the invention. The cells are in particular mammalian cells, preferably human cells.

Other features and advantages of the invention will be apparent from the examples which follow and will also be illustrated in the figures.

Figure 1:
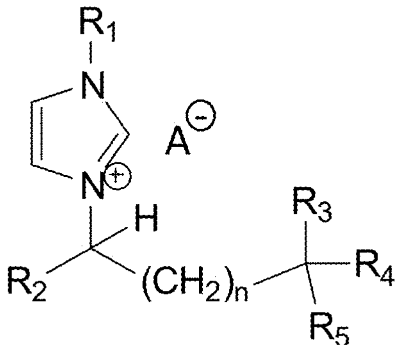
FIG. 1. Chemical structure of an imidazolium-based cationic lipid.

Co-transfections in HEK293 cells of Cas9 mRNA and HPRT-1 guide RNA (A, B) were performed using 0.3 μL (A) and 0.4 μL (B) of 2.5 mM cationic liposomal formulation W21.7/DPyPE (1:1.5).

Co-transfections in HEK293 cells of Cas9 mRNA and Negative Control guide RNA (C, D) were performed using 0.3 μL (C) and 0.4 μL (D) of cationic liposomal formulation W21.7/DPyPE (1:1.5).

Transfection in HEK293 cells of Cas9 mRNA without guide RNA (E, F) were performed using 0.3 μL (E) and 0.4 μL (F) of cationic liposomal formulation W21.7/DPyPE (1:1.5).

Two days after the transfection, the genomic DNA was extracted and the targeted HPRT-1 focus was amplified by PCR. After digestion by the T7 endonuclease I, the PCR products were run on a 2% agarose gel and stained with ethidium bromide. The genome editing efficiency was determined (INDEL %).

DESCRIPTION OF THE PREFERRED EMBODIMENTS

The INDEL % was 43.5% and 30.0% for the conditions A and B, respectively, where the INDEL % for the other conditions was less than 3%.

EXAMPLES

Experimental Section

Reagents and Chemicals

All reagents for chemistry and starting material were purchased from Sigma-Aldrich (France) and were used without prior purification. Solvents were ordered from SDS-Carlo Erba (France). Diethylether was dried and distilled over sodium benzophenone. Magnesium turnings special for Grignard reagent were purchased from Fisher Scientific (France). 1,2-Dioleoyl-sn-glycero-3-phosphoethanolamine (DOPE) is from Fluka (Sigma-Aldrich). 1,2-diphenytanoyl-sn-glycero-3-phosphoethanolamine (DPyPE) was from Corden Pharma, palmitoyl linoleoyl phosphatidylethanolamine (PaLiPE) and dilinoleoyl phosphatidylethanolamine (DiLiPE) from Avanti Polar Lipids.

Preparation of Liposomal Formulation

Liposomes were formed by dissolving the cationic lipid (1 mM) and the co-lipid (2 mM) in 2 mL of ethanol. Then, the mixture was injected in 18 mL water and this solution was sonicated with an ultrasonic processor Vitracell 500 W (Fischer Scientific) with 2 second pulses of 14 W during 5 minutes. The liposomal formulation in 10% ethanol was filtered through 0.45 μm and the stored at 4° C.

Particle Size and Zeta Potential Measurements

Figure 2:
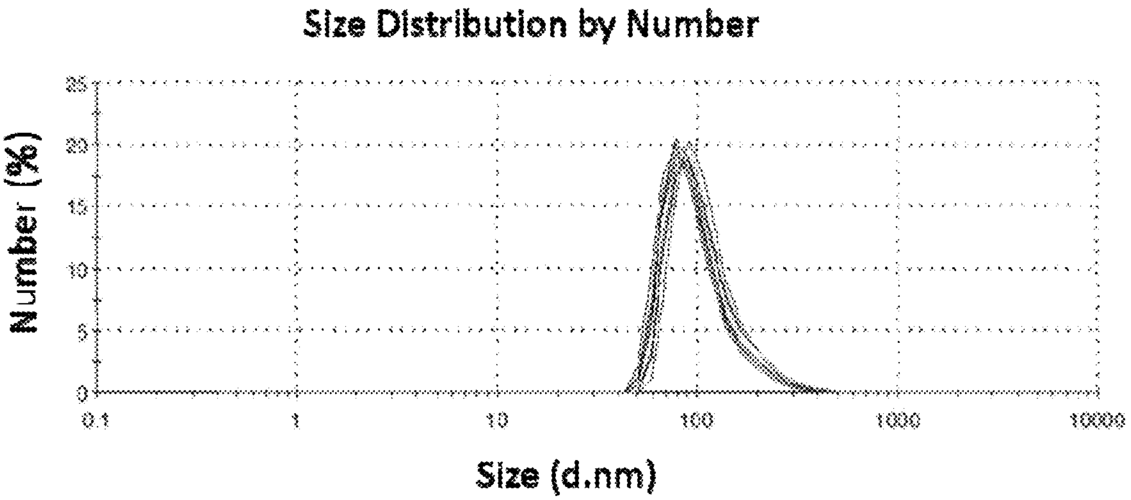
FIG. 2. Graph showing the particle size and zeta potential measurements by dynamic light scattering (DLS) of the cationic liposomal formulation W21.7/DPyPE. 1 mL of the cationic liposomal formulation containing 1 mM of compound W21.7 and 1.5 mM of DPyPE co-lipid was formulated with 10% ethanol in water was used to determine the DLS. The mean size was 93.4±11.7 nm. The zeta potential of this formulation was +52.8±1.95 mV.

Liposomal preparations at 1 mM of amphiphile with 1.5 mM of DPyPE were prepared with 10% ethanol in water, as described above. The particle size of these liposomal preparations was determined by light scattering using a Zetamaster (Malvern Instrument, Orsay, France) with the following specifications: sampling time, 30 seconds; 3 measurements per sample; medium viscosity, 1.0 cP; refractive index (RI) medium, 1.335; RI particle, 1.47; temperature: 25° C., at 633 nm laser wavelength. Particles size determination presented in FIG. 2 was obtained from the liposomal preparation at 1 mM W21.7 and 1.5 mM DOPE in water (stability of liposomes after 1 month of storage at 5° C.). Measurements were made in triplicates.

Cell Culture

Jurkat Clone E6-1 (ATCC® TIB-152™) human T lymphoblast cells were grown in RPMI-1640 (LONZA) with 10% of FBS (EUROBIO) and supplemented with 2 mM Glutamine (LONZA), 100 U/mL of penicillin and 100 μg/mL of streptomycin (LONZA) at 37° C. in a 5% $CO_2$ in air atmosphere.

Caco-2 (ATCC® HTB-37™) human colon epithelial cells were grown in DMEM 4.5 g/L glucose with 20% FBS supplemented with 1% non-essential amino acids, 1 mM sodium pyruvate, 2 mM glutamine and 100 U/mL of penicillin and 100 μg/mL of streptomycin at 37° C. in a 5% $CO_2$ in air atmosphere.

THP-1 (ATCC® TIB-202™) human peripheral blood monocyte cells were grown in RPMI-1640 with 10% FBS and supplemented with 10 mM HEPES buffer, 1 mM sodium pyruvate, 0.05 mM 2-mercaptoethanol, 2 mM glutamine, 100 U/mL of penicillin and 100 μg/mL of streptomycin at 37° C. in a 5% $CO_2$ in air atmosphere.

BJ (ATCC® CRL-2522™) human skin fibroblast cells were grown in Eagle's Minimum Essential Medium with 10% FBS and supplemented with 1% non-essential amino acids, 1 mM sodium pyruvate, 2 mM glutamine and 100 U/mL of penicillin and 100 μg/mL of streptomycin at 37° C. in a 5% $CO_2$ in air atmosphere.

mRNA EGFP transfection mRNA eGFP (996 nt, reference L-6101) from TriLink Technologies was used for the in vitro transfection experiments and expressed enhanced green fluorescent protein which is a common reporter gene (eGFP). This mRNA was capped with a Cap 0, polyadenylated and modified with 5-methylcytidine and pseudo-uridine.

One day before transfection, Caco-2, THP-1 or BJ Cells were seeded at 10 000, 25 000, or 5 000 cells per well (96-well plate format), respectively, in 125 μL of their respective complete medium and incubated at 37° C. in a 5% $CO_2$ in air atmosphere. For Jurkat cells, 25 000 cells were seeded per well prior transfection. On the day of transfection 150 ng of mRNA was added in 11.5 μL of 5% glucose solution, mixed with a vortex and incubated for 5 minutes at rt. Then, 1 μL of 1 mM cationic liposomal formulation was added onto the diluted mRNA, mixed with a vortex and incubated for 15 minutes at rt. The formulated mRNA solution (12.5 μL) was added into the well and the plate was incubated for 24 hours at 37° C. in a 5% $CO_2$ in air atmosphere.

For the GFP expression analysis, the cell culture medium was removed for the adherent cells and 50 μL of trypsin- EDTA (1×, Lonza) was added and the plate was incubated for 5 minutes at 37° C. 150 μL of complete medium were added to neutralize the trypsin, and the GFP expression was analysed (2000 events) by flow cytometry (Exc 488 nm, Em 520 nm) using a Guava easyCyte 6HT cytometer (Millipore).

CRISPR Cas9 mRNA Transfection

HEK293 (ECACC 85120602) human embryonic epithelial kidney cells were grown in Eagle MEM medium with 10% FBS supplemented with 2 mM Glutamine, 0.1 mM NEAA, 200 U/mL of penicillin and 200 μg/mL of streptomycin. One day before transfection, 12 500 cells were added per well (96-well plate format) in 125 μL of complete medium and the plate was incubated for 24 hours at 37° C. in a 5% $CO_2$ in air atmosphere.

The CleanCap™ Cas9 mRNA (4 521 nt, U-modified, Ref L-7206, TriLink Technologies) used for the transfection experiment expressed a version of the *Streptococcus pyogenes* SF370 Cas9 protein (CRISPR Associated Protein 9) with an N and C terminal nuclear localization signal (NLS). This mRNA was capped with the Cap 1 structure, polyadenylated, and substituted with a modified uridine and optimized for mammalian systems.

The Cas9 mRNA was co-transfected with CRISPR guide RNA consisting of the Alt-R™ CRISPR crRNA (36 nt) and tracrRNA (89 nt transactivating CRISPR RNA) from Integrated DNA Technologies (IDT). The Alt-R™ CRISPR Controls and PCR Assay used and contained a HPRT-1 Positive Control crRNA targeting the HPRT (hypoxanthine phosphoribosyltransferase) human gene, a CRISPR Negative Control crRNA, a CRISPR tracrRNA for complexing with the crRNA controls, and validated PCR primers for amplifying the targeted HPRT region.

On the day of transfection, 100 ng of CleanCap™ Cas9 mRNA was added in 11.5 μL of OPTIMEM with 50 ng of HPRT1 crRNA:tracr RNA, or 50 ng of Negative Control crRNA:tracrRNA, or without crRNA:tracrRNA and then the solution was mixed with a vortex and incubated for 5 minutes at rt. Then, 0.3-0.4 μL of 2.5 mM cationic liposomal formulation W21.7/DPyPE (1:1.5). was added onto the diluted mRNA, mixed with a vortex and incubated for 15 minutes at rt. The formulated mRNA solution (12.5 μL) was added into the well and the plate was incubated for 24 hours at 37° C. in a 5% $CO_2$ in air atmosphere.

Two days post-transfection, the medium was removed and cells were washed with PBS. Genomic DNA was isolated with the addition of 50 μL of QuickExtract™ DNA Extraction Solution 1.0 (Epicentre) per well followed by an incubation at 65° C. for 6 minutes, then at 98° C. for 2 minutes and storage at 4° C. The HPRT-1 targeted genomic DNA (250 ng) was amplified by PCR using the Primer HPRT1 mix (IDT) and the Q5® Hot Start High-Fidelity 2× Master Mix (New England Biolabs®). The following PCR conditions were used in a iCycler™ Thermal Cycler (Biorad): 1) incubation at 95° C. for 5 minutes, 2) 35 cycles (98° C. for 20 seconds, 68° C. for 15 seconds, 72° C. for 30 seconds), 3) incubation at 72° C. for 2 minutes and then stored at 4° C. 15 μL of amplified PCR DNA (250 ng) were combined with 1.5 μL of 10×NEBuffer 2 (NEB) and 1.5 μL of nuclease free water (total volume of 18 μL) and denatured then re-annealed with thermocycling at 95° C. for 10 minutes, 95 to 85° C. at −2° C./second; 85 to 25° C. at −0.3° C./second. The re-annealed DNA was incubated with 1 μl of T7 Endonuclease I (10 U/μl, NEB) at 37° C. for 15 minutes. 19 μL of T7 Endonuclease reaction was combined with 2 μL of loading buffer and analyzed on a 2% TAE agarose gel electrophoresed for 45 minutes at 100 V in the presence of Quick Load 100 pb DNA ladder (New England Biolabs®). The gel was stained with ethidium bromide for 30 min. Cas9-induced cleavage bands (827 and 256 bp) and the uncleaved band (1083 bp) were visualized on a G:Box transilluminator (Syngene) and quantified using GeneTools software. The INDEL % was calculated using the following formula: INDEL %=100*[1-(1-((intensities of cleaved bands)/(intensities of cleaved bands and uncleaved band)))].

In Vivo mRNA Delivery

CleanCap™ Firefly Luciferase mRNA (5-methoxyuridine), Luc mRNA (1921 nt, reference L-7202, TriLink Technologies) was used for in vivo experiments. This mRNA expressed the firefly luciferase protein (Photinus pyralis) and was capped with cap 1 structure, polyadenylated, and modified with 5-methoxyuridine.

For in vivo delivery mRNA/cationic liposome complexes were prepared as follows: for 1 mouse, the required amount of mRNA (5, 10 or 20 μg) was diluted in 200 μl of 5% glucose solution (final concentration). The cationic liposomal solution was added to the mRNA solution (at ratio of 2 μL per μg of mRNA), mixed and left for at least 15 minutes at room temperature. At this stage complexes are stable for more than 1 hour at room temperature.

All animal studies were done at the Mice Clinical Institute (CERBM GIE, Illkirch, France) and conducted in accordance to the French Animal Care guidelines and the protocols were approved by the Direction des Services Veterinaires. Six-weeks old SWISS OF1 female mice were obtained from Elevage Janvier. mRNA/cationic liposome complexes were intravenously injected through the retro-orbital sinus within 2 seconds. 24 hours after injection, mice were anesthetized by intra-peritoneal injection of pentobarbital (40 mg/kg, Ceva). The organs of interest were dissected, rinsed in PBS (1×) and mixed with an Ultra-Thurax homogenizer in 1 ml for spleen, kidney and heart and in 2 ml for lung and liver of lysis buffer 1× (Promega). Each organ mix was frozen at −80° C., thawed and an aliquot of 0.5 ml was taken for luciferase analysis. The aliquot was centrifuged for 5 minutes at 14,000 g. Luciferase enzyme activity was assessed on 5 μl of organ lysate supernatant using 100 μl of luciferin solution (Promega). The luminescence (expressed as Relative Light Unit, RLU) was integrated over 10 seconds by using a luminometer (Centro LB960, Berthold) and expressed as RLU per organ (6 mice per group).

Example 1. Synthesis of W21.7: 1-butyl-3-(2,6-dimethyl-14-octadecyldotriacontan-9-yl)-1H-imidazol-3-ium chloride

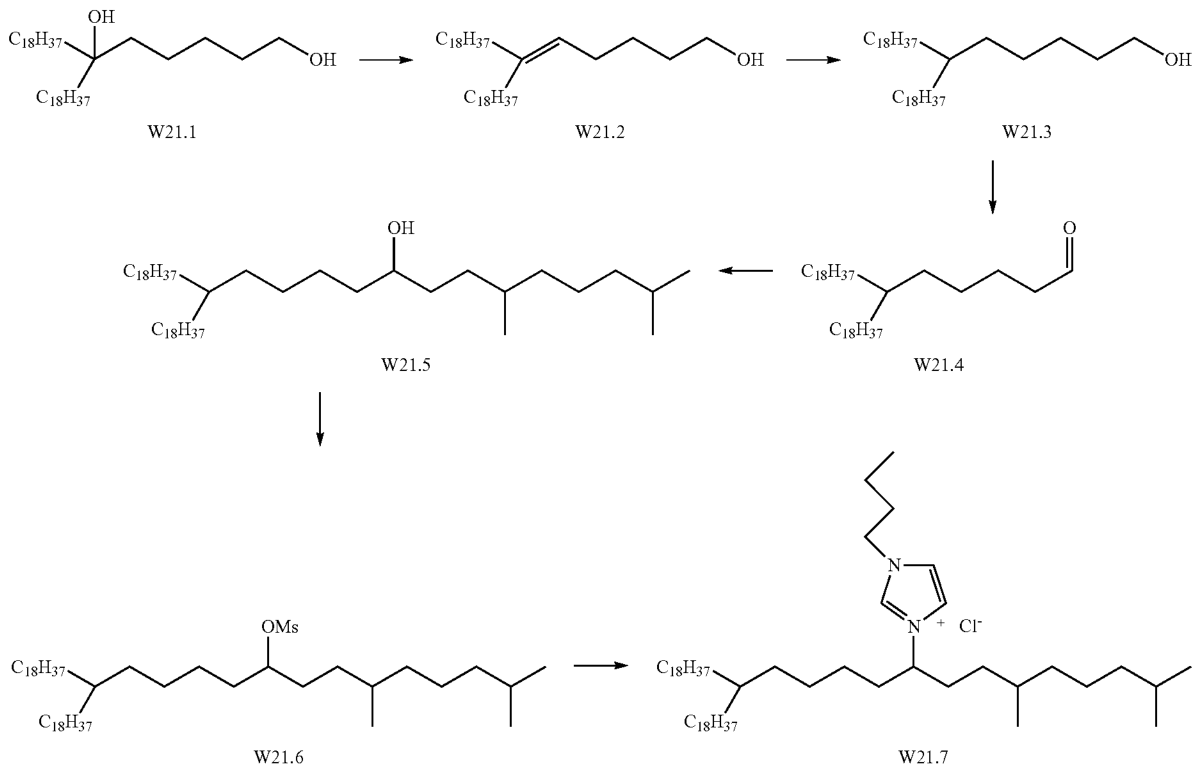

W21.1 W21.2 W21.3 W21.4 W21.5 W21.6 W21.7 a) Synthesis of Diol W21.1

To a solution of 100 mL of octadecylmagnesium chloride at 0.5 M in THE (50 mmoles) was added drop-wise 2.51 mL of ε-Caprolactone (2.58 g; 22.65 mmoles; MW=114.14) dissolved in 20 mL diethyl ether. The obtained reaction mixture was stirred under an argon atmosphere at room temperature for 24 hours. Then, the reaction mixture was poured onto 600 mL split ice, acidified with concentrated hydrochloric acid for 1 hour. The solid residue in suspension was filtered off and washed with water. The solid thus obtained was recrystallized from acetone and dried to afford 12.2 g of pure diol W21.1 (19.58 mmoles; MW=623.13, 86% yield).

Analysis of Diol W21.1:

TLC: Rf=0.25; solvent: ethyl acetate-heptane 3:7 (V:V); detection with vanillin/sulfuric acid (Merck TLC plates silica gel 60 $F_{254}$).

$^1$H-NMR (400 MHz, $CDCl_3$): δ=3.63 (t, J=6.6 Hz, 2H), 1.57 (quint, J=6.7 Hz, 2H), 1.45-1.05 (m, 74H), 0.86 (t, J=6.9 Hz, 6H).

b) Synthesis of Alcenol W21.2

Diol W21.1 (12.2 g; 19.58 mmoles; MW=623.13) and p-toluenesulfonic acid monohydrate (750 mg; 3.9 mmoles; MW=190.22) were dissolved in 300 mL toluene. The mixture was refluxed for 3 hours, water was removed with a Dean-Stark trap. The solvents were removed under reduced pressure to give a crude that was chromatographed on silica gel ($CH_2Cl_2$-Heptane 1:1) to afford 10.80 g of pure alcenol W21.2 (mixture of isomers) (17.85 mmoles; MW=605.12, 91% yield).

Analysis of Alcenol W21.2:

TLC: Rf=0.35; solvent: $CH_2Cl_2$-Heptane 7:3; detection with vanillin/sulfuric acid (Merck TLC plates silica gel 60 $F_{254}$).

$^1$H-NMR (400 MHz, $CDCl_3$): δ=5.11-5.03 (m, 1H), 3.62 (td, J=6.6 Hz, 1.9 Hz, 2H), 2.03-1.89 (m, 6H), 1.60-1.51 (m, 2H), 1.49-0.99 (m, 66H), 0.86 (t, J=6.8 Hz, 6H).

c) Synthesis of Alcohol W21.3

Mixture of alcenol isomers W21.2 (10.80 g, 17.85 mmoles, MW=605.12) was dissolved in 300 mL ethyl acetate and catalytic hydrogenation with Palladium on charcoal (Pd/C 10%, 2 g) for 24 hours at 1 atmosphere pressure of hydrogen was applied. After replacement of hydrogen by argon, the mixture was filtered through Celite® 545. The filter cake was washed with 2×250 mL of hot $CH_2Cl_2$. Combined solvents were removed under reduced pressure to afford 10.10 g of pure alcohol W21.3 (16.63 mmoles, MW=607.13, 93% yield).

Analysis of Alcohol W21.3:

TLC: Rf=0.35; solvent: $CH_2Cl_2$-Heptane 7:3; detection with vanillin/sulfuric acid (Merck TLC plates silica gel 60 $F_{254}$).

$^1$H-NMR (400 MHz, $CDCl_3$): δ=3.62 (t, J=6.7 Hz, 2H), 1.55 (quint, J=6.9 Hz, 2H), 1.44-1.00 (m, 75H), 0.86 (t, J=6.7 Hz, 6H).

d) Formation of Aldehyde W21.4

Alcohol W21.3 (10.10 g, 16.63 mmoles, MW=607.13) was dissolved in 300 mL $CH_2Cl_2$, Pyridinium chlorochromate (7 g, 32.47 mmoles, MW=215.56) was added and the reaction stirred at room temperature for 3 hours under an argon atmosphere. The mixture was filtered through Celite® 545 and the filter cake was washed with $CH_2Cl_2$. Combined solvents were removed under reduced pressure and the obtained crude was chromatographed on silica gel ($CH_2Cl_2$-Heptane 1:4) to afford 8.08 g of pure aldehyde W21.4 (13.35 mmoles, MW=605.12, 80% yield).

Analysis of Aldehyde W21.4:

TLC: Rf=0.35; solvent: $CH_2Cl_2$-Heptane 3:7; detection with vanillin/sulfuric acid (Merck TLC plates silica gel 60 $F_{254}$).

$^1$H-NMR (400 MHz, $CDCl_3$): δ=9.74 (t, J=2.0 Hz, 1H), 2.40 (td, J=7.3 Hz, 2.0 Hz, 2H), 1.59 (quint, J=7.3 Hz, 2H), 1.36-1.12 (m, 73H), 0.86 (t, J=6.9 Hz, 6H).

e) Synthesis of W21.5

Aldehyde W21.4 (8.08 g, 13.35 mmoles, MW=605.12) was dissolved in 100 mL THE and then introduced drop-wise on 50 mL of a stirred solution of 3,7-Dimethyloctyl-magnesium bromide at 1 M in diethyl ether (50 mmoles). The obtained reaction mixture was stirred under an argon atmosphere at room temperature for 24 hours. Then, the reaction mixture was poured onto 600 mL split ice, acidified with concentrated chlorhydric acid for 1 hour. This solution was then extracted with 3×200 mL of $CH_2Cl_2$, dried over anhydrous sodium sulfate and solvents were removed under reduced pressure. The residue was then resuspended in 200 mL of Acetone and cooled in an ice-water bath for 1 hour. Desired product precipitated as a white solid that was recovered by filtration. After drying, 9.80 g of alcohol W21.5 were obtained (13.11 mmoles, MW=747.40, 98% yield).

Analysis of Alcohol W21.5:

TLC: Rf=0.40; solvent: $CH_2Cl_2$-Heptane 3:7; detection with vanillin/sulfuric acid (Merck TLC plates silica gel 60 $F_{254}$).

$^1$H-NMR (400 MHz, $CDCl_3$): δ=3.75-3.50 (m, 1H), 1.63-0.96 (m, 89H), 0.92-0.75 (m, 15H).

f) Synthesis of W21.6

Alcohol W21.5 (9.80 g; 13.11 mmoles; MW=747.40) was dissolved in 250 mL of dry $CH_2Cl_2$ and 18 mL of triethyl-amine (13.07 g; 129.16 mmoles; MW=101.19) were added followed by 8 mL of methanesulfonyl chloride (11.84 g; 103.36 mmoles; MW=114.55) introduced drop-wise. The mixture was stirred overnight at room temperature. After removal of the solvents under reduced pressure, the residue was dissolved in 200 mL of methanol and cooled in an ice-water bath for 1 hour. Desired product precipitated as a white solid collected by filtration on a filter paper. After solubilization in $CH_2Cl_2$ and evaporation, 9.60 g of compound W21.6 were obtained (11.63 mmoles, MW=825.49, 88% yield).

Analysis of Mesylate W21.6:

$^1$H-NMR (400 MHz, $CDCl_3$): δ=4.66 (quint, J=5.9 Hz, 1H), 2.97 (s, 3H), 1.76-1.59 (m, 4H), 1.57-0.98 (m, 85H), 0.91-0.78 (m, 15H).

g) Synthesis of W21.7

Mesylate W21.6 (9.60 g; 11.63 mmoles; MW=825.49) was resuspended in 40 mL of 1-butylimidazole and was stirred at 80° C. for 5 days under an argon atmosphere. The mixture was diluted with 400 mL of methanol and insoluble matter was removed by filtration. Filtrate was cooled in an ice-water bath, slowly acidified with 100 mL of hydrochloric acid 37% and evaporated to dryness. The residue was resuspended in 400 mL of ultra-pure water and cooled in an ice-water bath for 1 hour. Desired product, insoluble in water, was collected by filtration on a filter paper. The obtained residue was further chromatographed on silica gel ($CH_2Cl_2$-methanol 98:2) to afford 6.78 g of compound W21.7 as a white solid (7.62 mmoles, MW=890.03, 74% yield).

Analysis of Compound W21.7:

TLC: Rf=0.45; solvent: $CH_2Cl_2$-methanol 9:1; detection with iodine (Merck TLC plates silica gel 60 $F_{254}$).

$^1$H-NMR (400 MHz, $CDCl_3$): δ=11.30 (s, 1H), 7.23-7.20 (m, 1H), 7.13-7.07 (m, 1H), 4.54-4.45 (m, 1H), 4.41 (t, J=7.3 Hz, 2H), 1.98-1.64 (m, 8H), 1.54-0.98 (m, 88H), 0.88-0.77 (m, 15H).

Example 2. Synthesis of W20.7: 1-butyl-3-(24-tetradecyloctatriacont-9-en-19-yl)-1H-imidazol-3-ium chloride

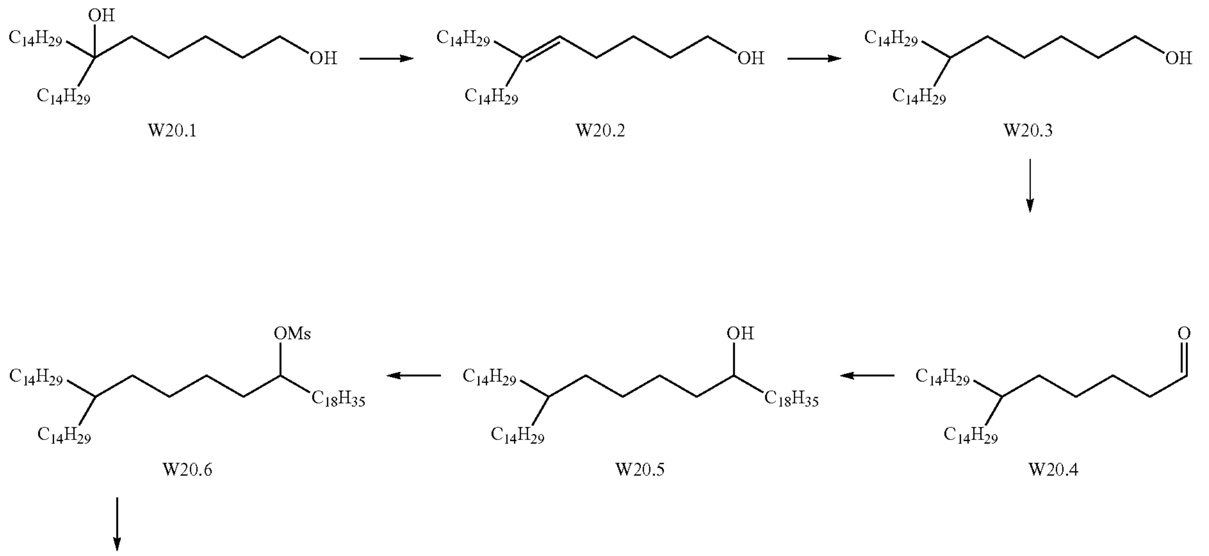
W20.1 W20.2 W20.3 W20.6 W20.5 W20.4

-continued

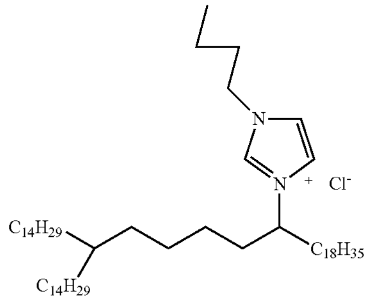

W20.7

Compounds W20.1 to W20.7 were obtained following procedures similar to the ones described above (W21.1 to W21.7).

Analysis of Compound W20.7:

TLC: Rf=0.5; solvent: $CH_2Cl_2$-methanol 9:1; detection with iodine (Merck TLC plates silica gel 60 $F_{254}$).

$^1$H-NMR (400 MHz, $CDCl_3$): δ=11.31 (s, 1H), 7.22-7.18 (m, 1H), 7.12-7.08 (m, 1H), 5.37-5.25 (m, 2H), 4.56-4.46 (m, 1H), 4.40 (t, J=7.3 Hz, 2H), 2.03-1.70 (m, 10H), 1.42-0.90 (m, 88H), 0.85 (t, J=6.8 Hz, 9H).

Example 3. Synthesis of W22.7: 1-butyl-3-(2,6-dimethyl-14-tetradecyloctacosan-9-yl)-1H-imidazol-3-ium chloride

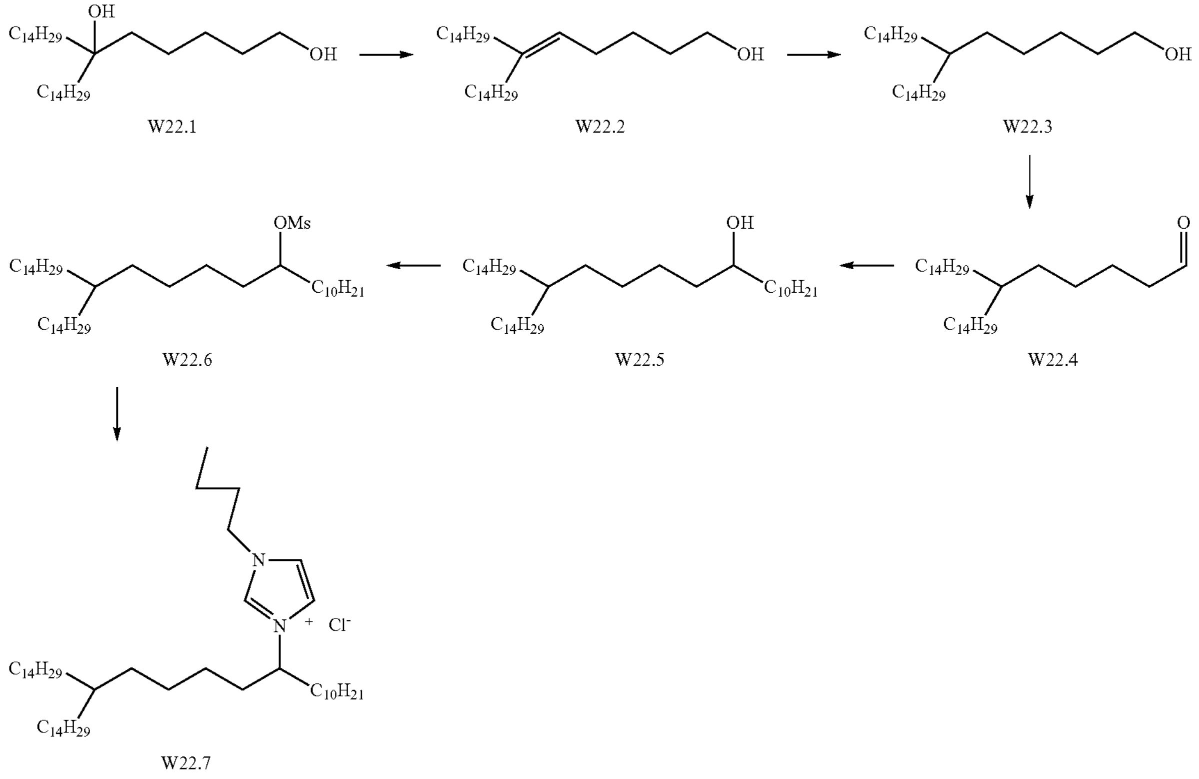

Compounds W22.1 to W22.7 were obtained following procedures similar to the ones described above (W21.1 to W21.7).

Analysis of Compound W22.7:

TLC: Rf=0.45; solvent: $CH_2Cl_2$-methanol 9:1; detection with iodine (Merck TLC plates silica gel 60 $F_{254}$).

$^1$H-NMR (400 MHz, $CDCl_3$): δ=11.30 (s, 1H), 7.25-7.22 (m, 1H), 7.13-7.09 (m, 1H), 4.55-4.45 (m, 1H), 4.42 (t, J=7.3 Hz, 2H), 1.96-1.67 (m, 6H), 1.55-0.99 (m, 71H), 0.95 (t, J=7.3 Hz, 3H), 0.89-0.77 (m, 15H).

Example 4. Synthesis of W23.7: 1-butyl-3-(14-(3,7-dimethyloctyl)-2,6,17,21-tetramethyldocosan-9-yl)-1H-imidazol-3-ium chloride

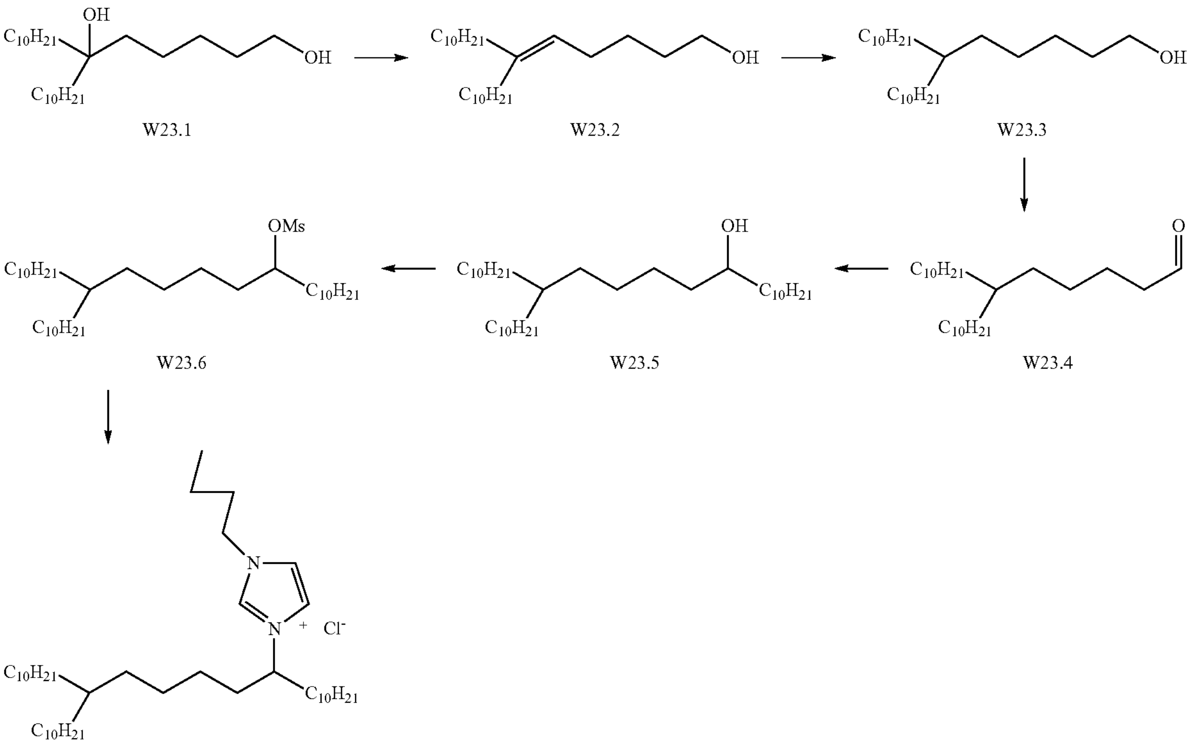

W23.1 W23.2 W23.3 W23.4 W23.5 W23.6 W23.7

Compounds W23.1 to W23.7 were obtained following procedures similar to the ones described above (W21.1 to W21.7).

Analysis of Compound W23.7:

TLC: Rf=0.60; solvent: $CH_2Cl_2$-methanol 9:1; detection with iodine (Merck TLC plates silica gel 60 $F_{254}$).

$^1$H-NMR (400 MHz, $CDCl_3$): δ=11.12 (s, 1H), 7.42-7.36 (m, 1H), 7.18-7.12 (m, 1H), 4.52-4.42 (m, 1H), 4.39 (t, J=7.5 Hz, 2H), 1.97-1.64 (m, 6H), 1.55-0.88 (m, 46H), 0.87-0.68 (m, 27H).

Example 5. Synthesis of W24.7: 3-(2,6-dimethyl-14-octadecyldotriacontan-9-yl)-1H-imidazole

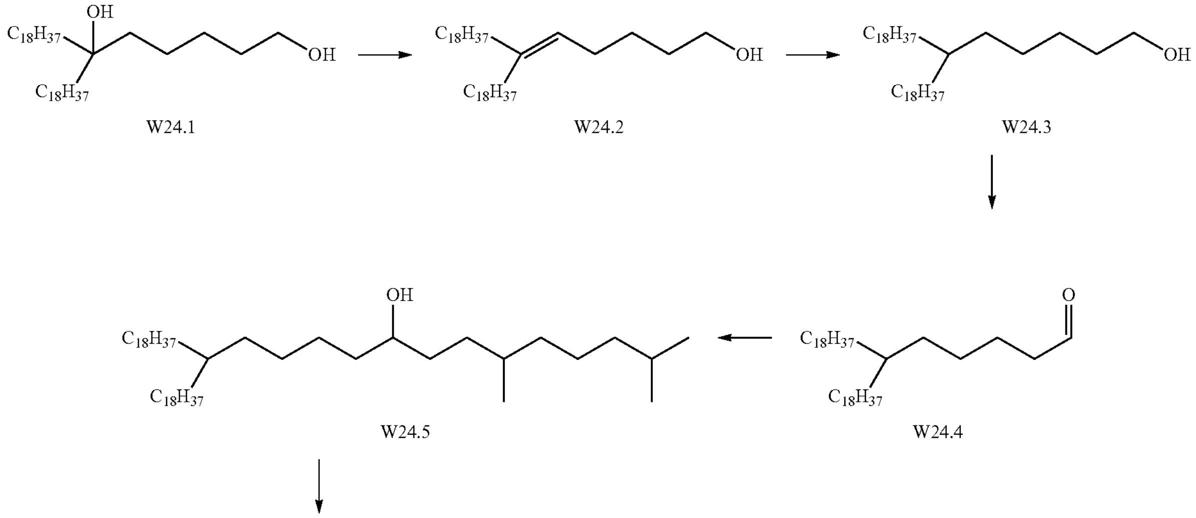

W24.1 W24.2 W24.3 W24.4 W24.5

-continued

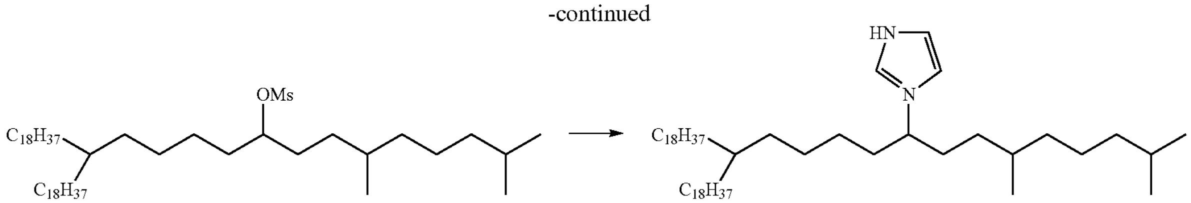

W24.6 W24.7

Compounds W24.1 to W24.6 were obtained following procedures similar to the ones described above (W21.1 to W21.6). Imidazole (0.165 g; 2.42 mmoles; MW=68.08) was treated with 0.11 g of sodium hydride 60% in mineral oil (2.75 mmoles; MW=24.00) in 20 mL of boiling tetrahydrofuran for 1 hour. 1.00 g of mesylate W24.6 dissolved in 20 mL of Tetrahydrofuran were then added, the mixture was refluxed for 24 hours. The reaction mixture was diluted with water and the solution was then extracted with 3×200 mL of $CH_2Cl_2$, dried over anhydrous sodium sulfate and solvents were removed under reduced pressure. The obtained residue was further chromatographed on silica gel ($CH_2Cl_2$-Methanol 99:1) to afford 0.14 g of compound W24.7 (0.17 mmoles, MW=797.46, 14% yield).

Analysis of Compound W24.7:

TLC: Rf=0.30; solvent: $CH_2Cl_2$-methanol 98:2; detection with iodine (Merck TLC plates silica gel 60 $F_{254}$).

$^1$H-NMR (400 MHz, $CDCl_3$): δ=7.58 (s, 1H), 7.14-7.08 (m, 1H), 6.94-6.86 (m, 1H), 3.91-3.81 (m, 1H), 1.83-1.72 (m, 4H), 1.54-1.42 (m, 1H), 1.41-0.94 (m, 84H), 0.91-0.76 (m, 15H).

Example 6. Synthesis of W9.7: 1-methyl-3-(20-tetradecyltetratriacontan-15-yl)-1H-imidazol-3-ium chloride

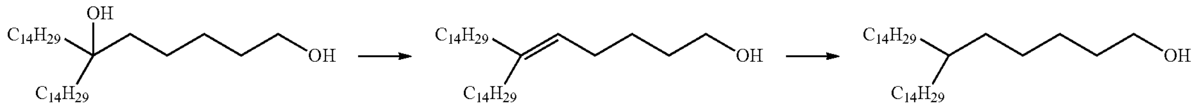

W9.1 W9.2 W9.3

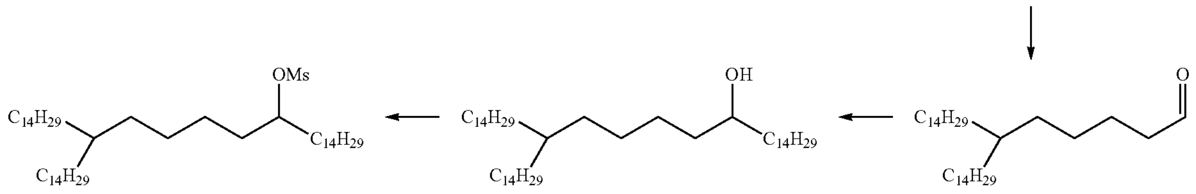

W9.6 W9.5 W9.4

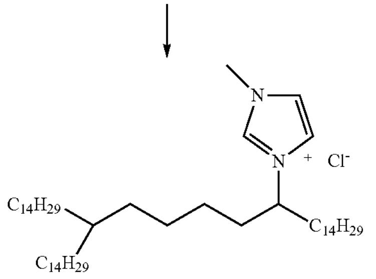

W9.7

Compounds W9.1 to W9.7 were obtained following procedures similar to the ones described above (W21.1 to W21.7).

Analysis of Compound W9.7:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=11.10 (s, 1H), 7.28-7.25 (m, 1H), 7.12-7.08 (m, 1H), 4.46-4.36 (m, 1H), 4.14 (s, 3H), 1.92-1.71 (m, 4H), 1.35-0.95 (m, 83H), 0.85 (t, J=6.8 Hz, 9H).

Example 7. Synthesis of W10.7: 1-methyl-3-(24-tetradecyloctatriacont-9-en-19-yl)-1H-imidazol-3-ium chloride

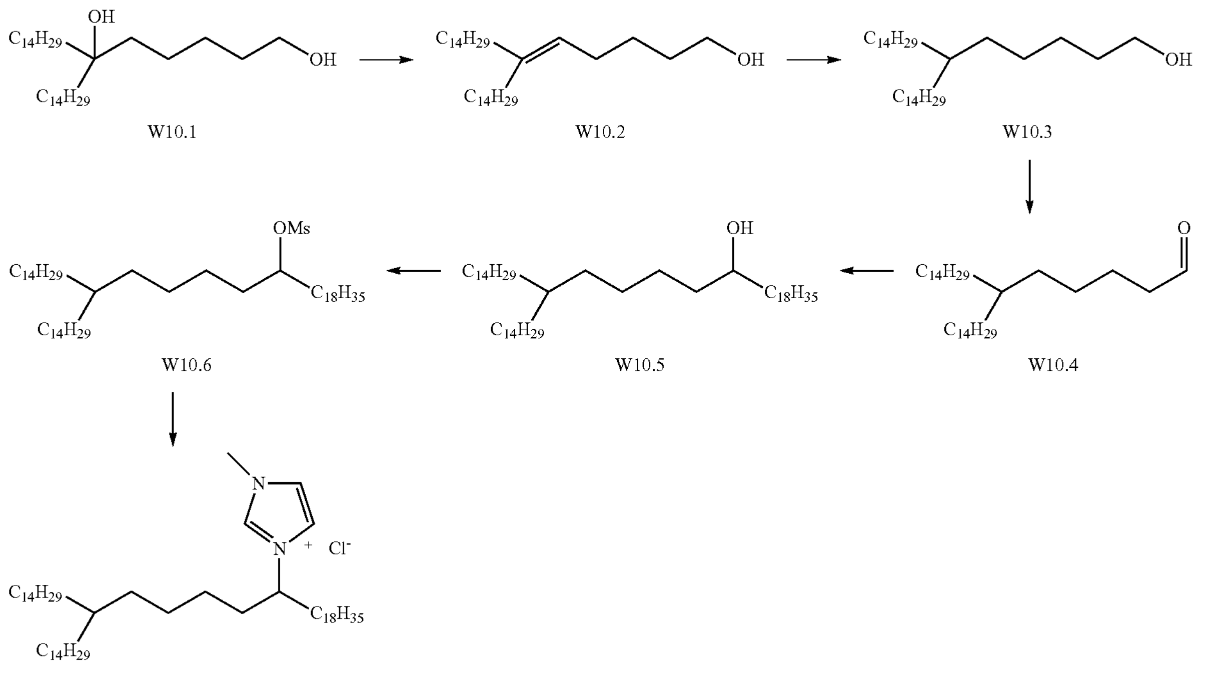

W10.1 W10.2 W10.3 W10.4 W10.5 W10.6 W10.7

Compounds W10.1 to W10.7 were obtained following procedures similar to the ones described above (W21.1 to W21.7).

Analysis of Compound W10.7:

TLC: Rf=0.40; solvent: $CH_2Cl_2$-methanol 9:1; detection with iodine (Merck TLC plates silica gel 60 $F_{254}$).

$^1$H-NMR (400 MHz, $CDCl_3$): δ=11.12 (s, 1H), 7.28-7.25 (m, 1H), 7.12-7.08 (m, 1H), 5.37-5.27 (m, 2H), 4.46-4.36 (m, 1H), 4.13 (s, 3H), 2.03-1.70 (m, 8H), 1.35-0.95 (m, 83H), 0.85 (t, J=6.9 Hz, 9H).

Example 8. Synthesis of W11.7: 1-methyl-3-(24-tetradecyloctatriacontan-19-yl)-1H-imidazol-3-ium chloride

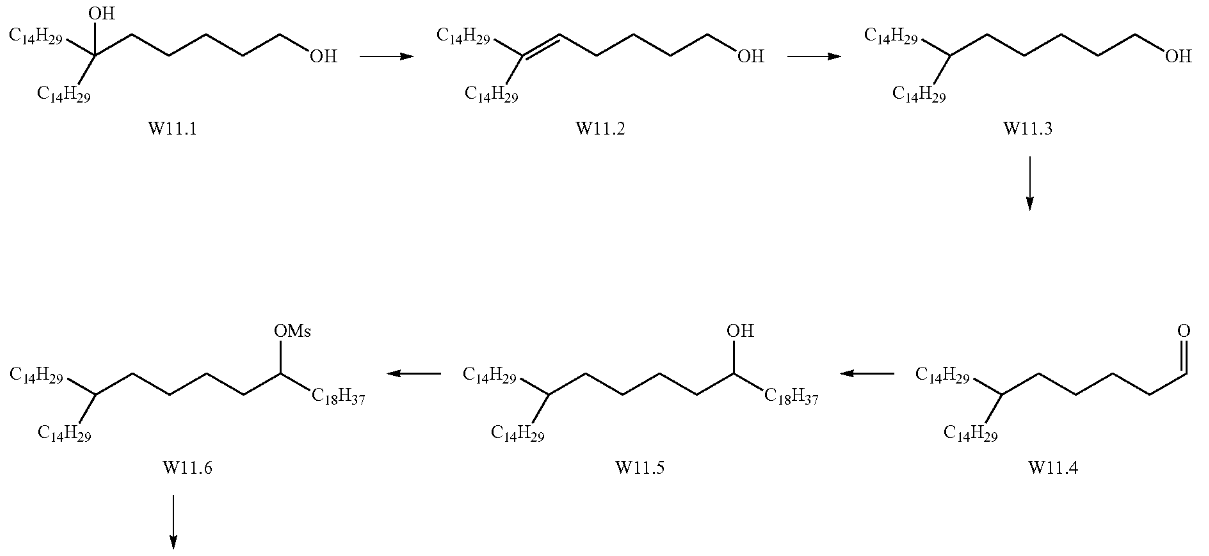

W11.1 W11.2 W11.3 W11.4 W11.5 W11.6

-continued

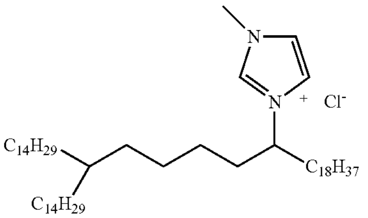

W11.7

Compounds W11.1 to W11.7 were obtained following procedures similar to the ones described above (W21.1 to W21.7).

Analysis of Compound W11.7:

TLC: Rf=0.50; solvent: $CH_2Cl_2$-methanol 9:1; detection with iodine (Merck TLC plates silica gel 60 $F_{254}$).

$^1$H-NMR (400 MHz, $CDCl_3$): δ=10.98 (s, 1H), 7.31-7.27 (m, 1H), 7.13-7.09 (m, 1H), 4.47-4.37 (m, 1H), 4.13 (s, 3H), 1.92-1.71 (m, 4H), 1.47-0.96 (m, 91H), 0.85 (t, J=6.8 Hz, 9H).

Example 9. Synthesis of W12.7: 1-methyl-3-(2,6-dimethyl-14-tetradecyloctacosan-9-yl)-1H-imidazol-3-ium chloride

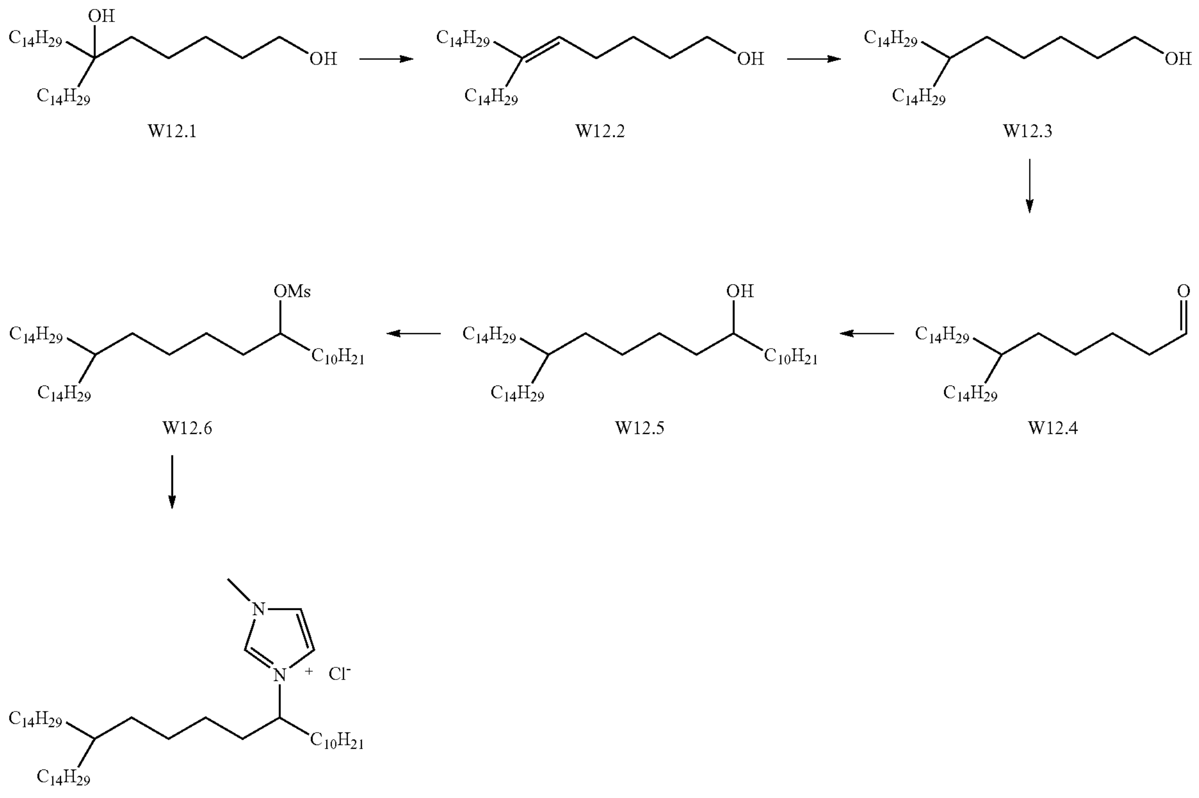

W12.1 W12.2 W12.3 W12.6 W12.5 W12.4 W12.7

Compounds W12.1 to W12.7 were obtained following procedures similar to the ones described above (W21.1 to W21.7).

Analysis of Compound W12.7:

TLC: Rf=0.40; solvent: $CH_2Cl_2$-methanol 9:1; detection with iodine (Merck TLC plates silica gel 60 $F_{254}$).

$^1$H-NMR (400 MHz, $CDCl_3$): δ=11.08 (s, 1H), 7.27 (t, J=1.7 Hz, 1H), 7.11 (t, J=1.7 Hz, 1H), 4.47-4.36 (m, 1H), 4.14 (s, 3H), 1.91-1.72 (m, 4H), 1.35-0.96 (m, 75H), 0.89-0.81 (m, 9H).

Example 10. Synthesis of W13.7: 1-methyl-3-(24-octadecyldotetracontan-19-yl)-1H-imidazol-3-ium chloride

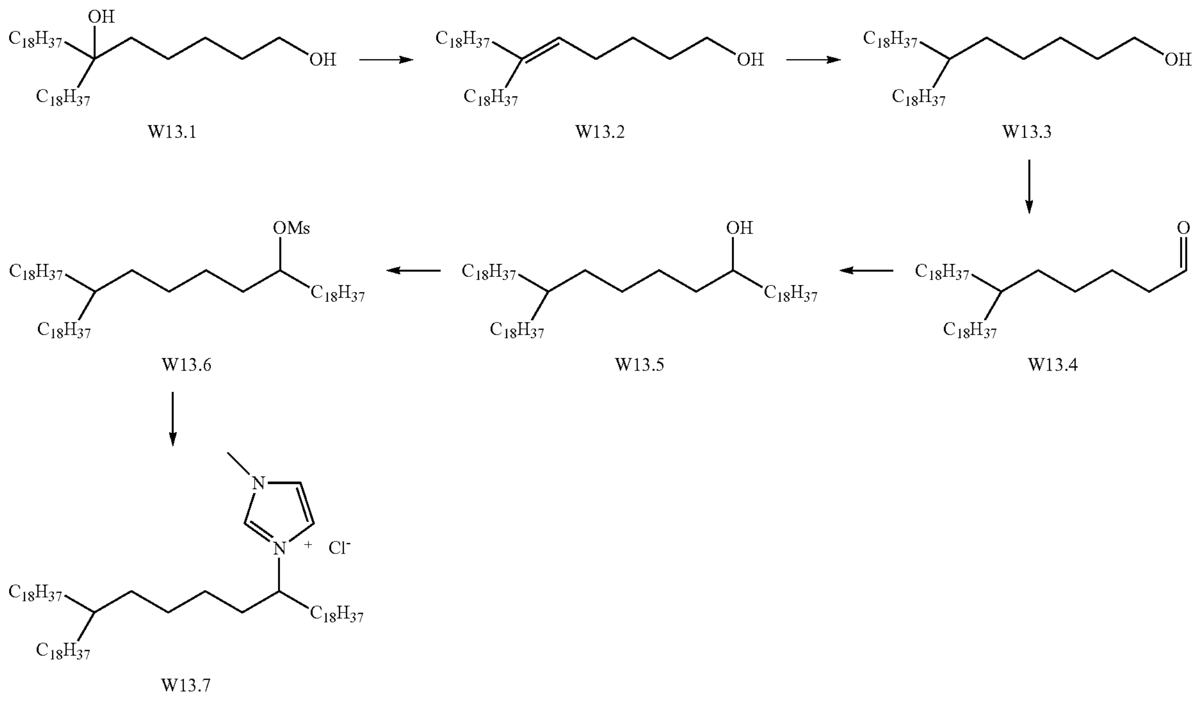

W13.1 W13.2 W13.3 W13.4 W13.5 W13.6 W13.7

Compounds W13.1 to W13.7 were obtained following procedures similar to the ones described above (W21.1 to W21.7).

Analysis of Compound W13.7:

TLC: Rf=0.35; solvent: $CH_2Cl_2$-methanol 9:1; detection with iodine (Merck TLC plates silica gel 60 $F_{254}$).

$^1$H-NMR (400 MHz, $CDCl_3$): δ=11.11 (s, 1H), 7.29-7.26 (m, 1H), 7.12-7.08 (m, 1H), 4.46-4.36 (m, 1H), 4.13 (s, 3H), 1.92-1.70 (m, 4H), 1.43-0.94 (m, 107H), 0.85 (t, J=6.8 Hz, 9H).

Example 11. Synthesis of W14.7: 1-methyl-3-(1-cyclohexyl-7-octadecylpentacosan-2-yl)-1H-imidazol-3-ium chloride

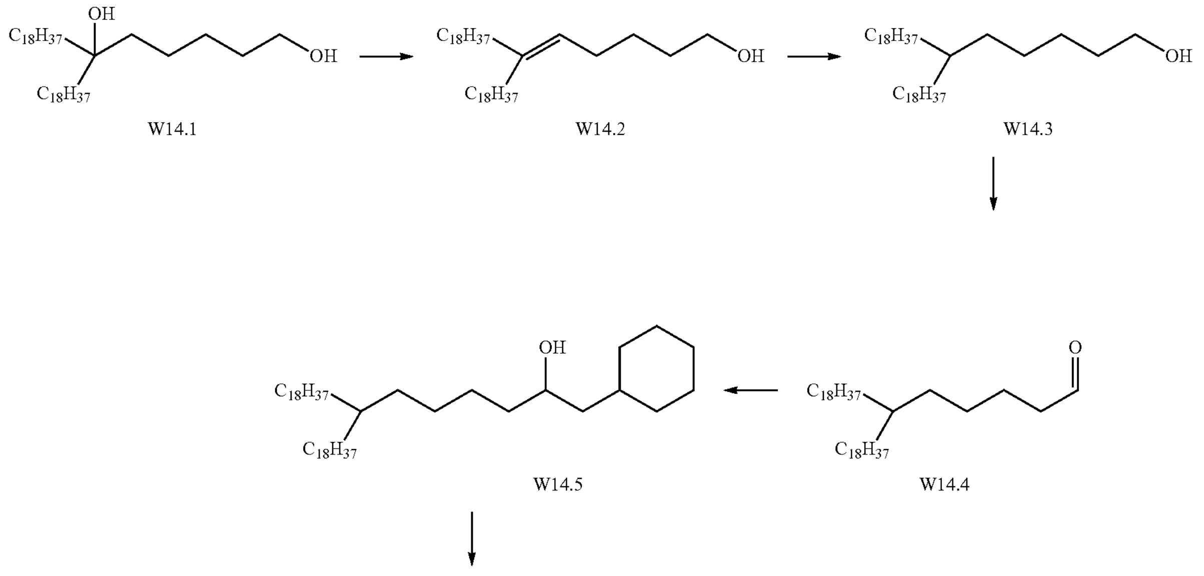

W14.1 W14.2 W14.3 W14.4 W14.5

-continued

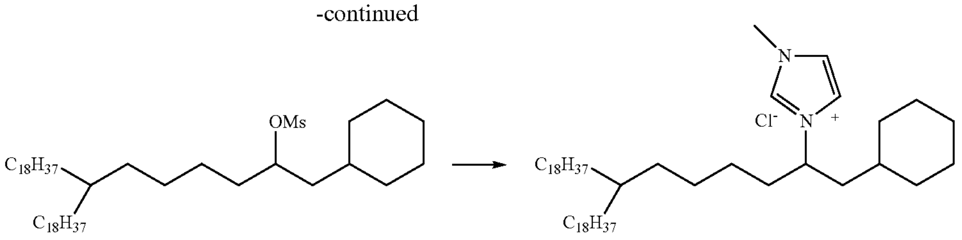

W14.6 W14.7

Compounds W14.1 to W14.7 were obtained following procedures similar to the ones described above (W21.1 to W21.7).

Analysis of Compound W14.7:

TLC: Rf=0.40; solvent: $CH_2Cl_2$-methanol 9:1; detection with iodine (Merck TLC plates silica gel 60 $F_{254}$).

$^1$H-NMR (400 MHz, $CDCl_3$): δ=11.04 (s, 1H), 7.27-7.23 (m, 1H), 7.12-7.07 (m, 1H), 4.52-4.42 (m, 1H), 4.15 (s, 3H), 1.89-1.52 (m, 8H), 1.35-0.89 (m, 82H), 0.85 (t, J=6.8 Hz, 6H).

Example 12. Synthesis of W15.7: 1-methyl-3-(7-octadecyl-1-phenylpentacosan-2-yl)-1H-imidazol-3-ium chloride

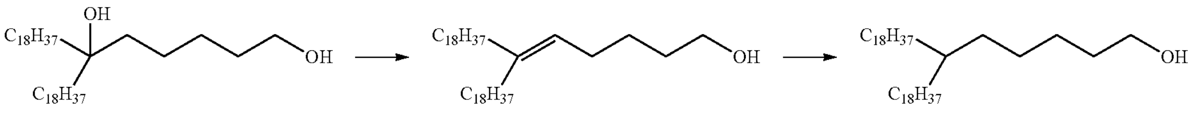

W15.1 W15.2 W15.3

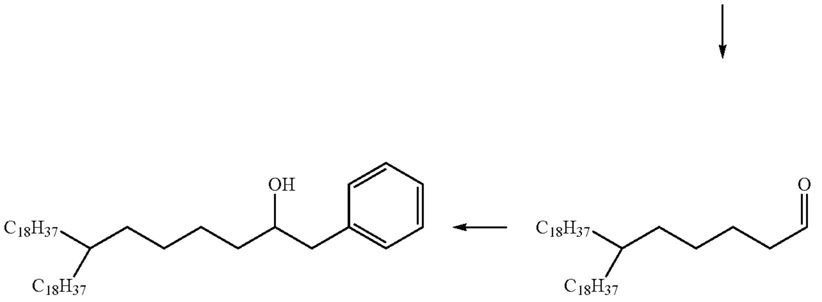

W15.5 W15.4

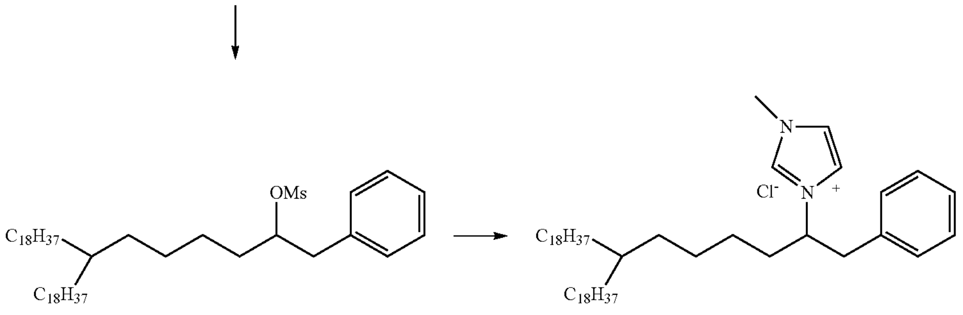

W15.6 W15.7

Compounds W15.1 to W15.7 were obtained following procedures similar to the ones described above (W21.1 to W21.7).

Analysis of Compound W15.7:

TLC: Rf=0.35; solvent: $CH_2Cl_2$-methanol 9:1; detection with iodine (Merck TLC plates silica gel 60 $F_{254}$).

$^1$H-NMR (400 MHz, $CDCl_3$): δ=10.94 (s, 1H), 7.24-7.17 (m, 3H), 7.17-7.13 (m, 1H), 7.13-7.07 (m, 2H), 6.92-6.88 (m, 1H), 4.72-4.62 (m, 1H), 4.05 (s, 3H), 3.26-3.11 (m, 2H), 2.01-1.91 (m, 2H), 1.42-0.97 (m, 75H), 0.85 (t, J=6.8 Hz, 6H).

Example 13. Synthesis of W16.7: 1-methyl-3-(2,6-dimethyl-14-octadecyldotriacontan-9-yl)-1H-imidazole-3-ium chloride

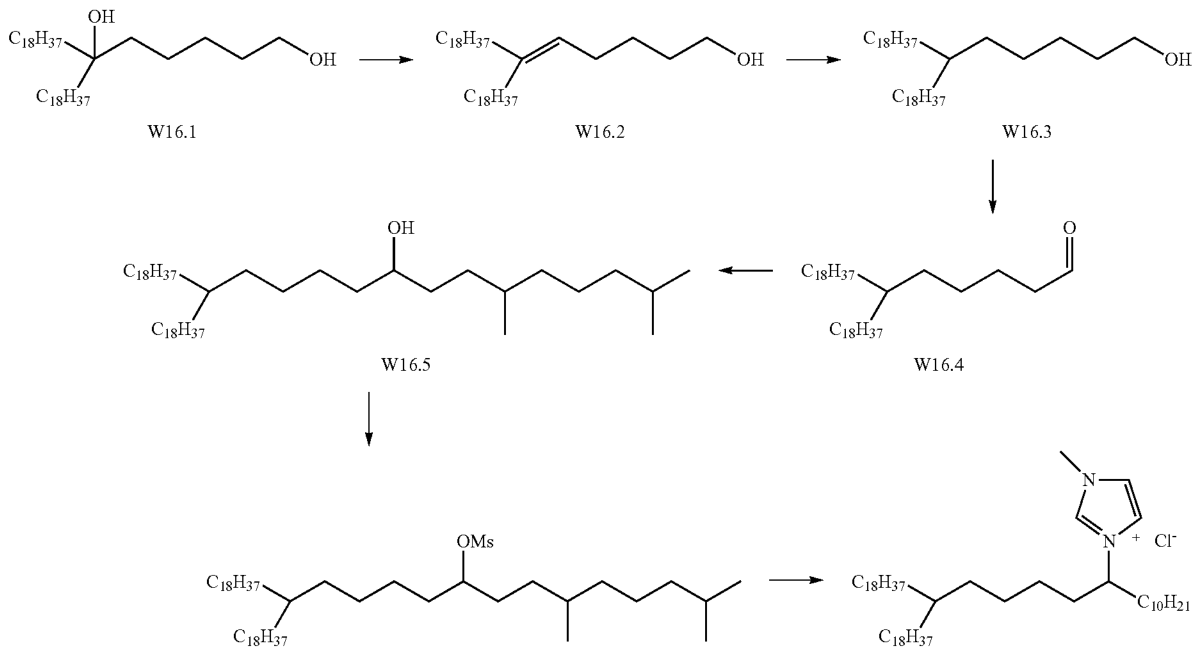

W16.1 W16.2 W16.3 W16.4 W16.5 W16.6 W16.7

Compounds W16.1 to W16.7 were obtained following procedures similar to the ones described above (W21.1 to W21.7).

Analysis of Compound W16.7:

TLC: Rf=0.35; solvent: $CH_2Cl_2$-methanol 9:1; detection with iodine (Merck TLC plates silica gel 60 $F_{254}$).

$^1$H-NMR (400 MHz, $CDCl_3$): δ=5=11.03 (s, 1H), 7.31-7.25 (m, 1H), 7.15-7.06 (m, 1H), 4.48-4.33 (m, 1H), 4.15 (s, 3H), 1.96-1.65 (m, 4H), 1.55-0.93 (m, 85H), 0.91-0.75 (m, 15H).

Example 14. Synthesis of W17.7: 1-methyl-3-(12-octadecyltriacontan-7-yl)-1H-imidazol-3-ium chloride

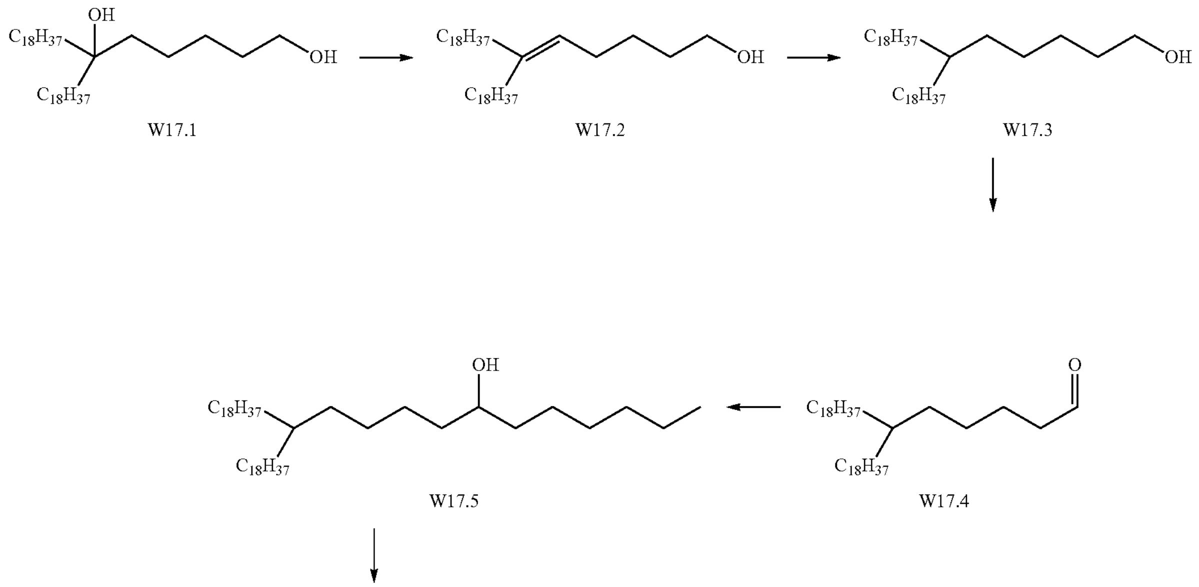

W17.1 W17.2 W17.3 W17.4 W17.5

-continued

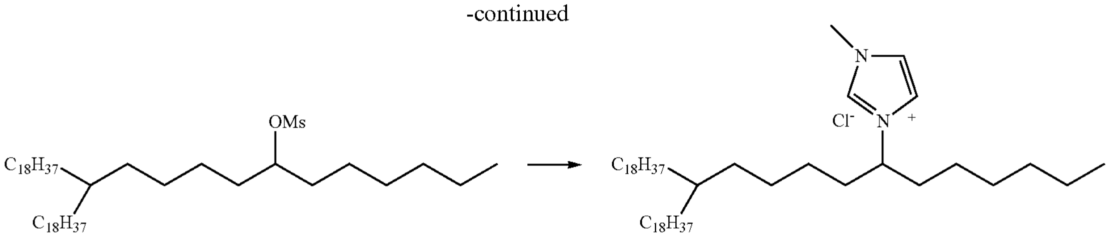

W17.6 W17.7

Compounds W17.1 to W17.7 were obtained following procedures similar to the ones described above (W21.1 to W21.7).

Analysis of Compound W17.7:

TLC: Rf=0.30; solvent: $CH_2Cl_2$-methanol 9:1; detection with iodine (Merck TLC plates silica gel 60 $F_{254}$).

$^1$H-NMR (400 MHz, $CDCl_3$): δ=11.05 (s, 1H), 7.27 (t, J=1.8 Hz, 1H), 7.11 (t, J=1.8 Hz, 1H), 4.47-4.37 (m, 1H), 4.13 (s, 3H), 1.93-1.70 (m, 4H), 1.48-0.95 (m, 83H), 0.91-0.77 (m, 9H).

Example 15. Synthesis of W18.9: 1-methyl-3-(15,25-ditetradecylnonatriacontan-20-yl)-1H-imidazol-3-ium chloride

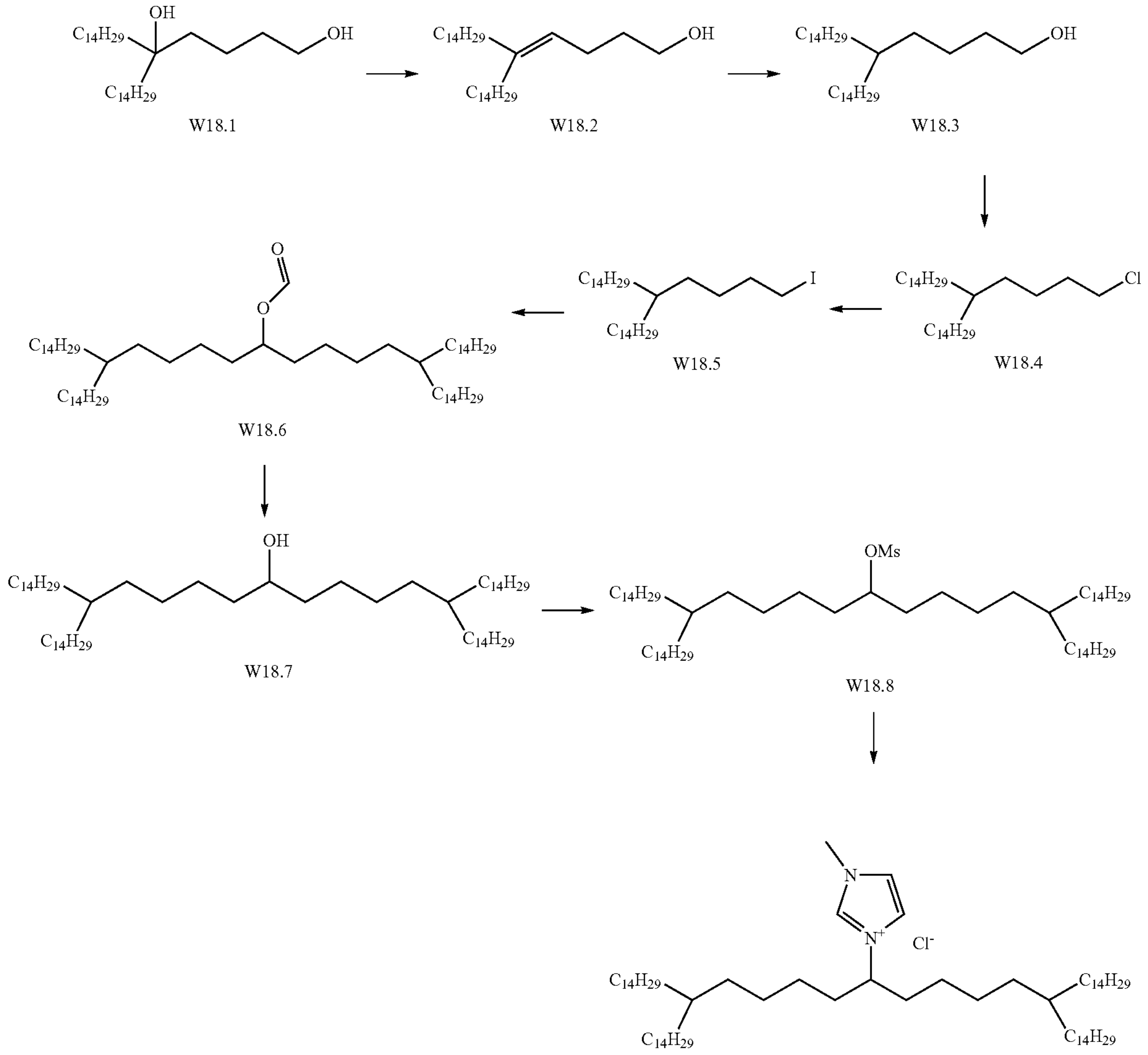

W18.1 W18.2 W18.3 W18.4 W18.5 W18.6 W18.7 W18.8 W18.9

Compounds W18.1 to W18.3, W18.8 and W18.9 were obtained following procedures similar to the ones described above (W21.1 to W21.3, W21.8 and W21.9).

a) Synthesis of W18.4

To 1.50 g of cyanuric chloride (8.13 mmoles; MW=184.41) in 20 mL of N,N-dimethylformamide was added alcohol W18.3 (2.00 g; 4.16 mmoles; MW=480.89) resuspended in 100 mL of $CH_2Cl_2$. The reaction mixture was stirred under an argon atmosphere at room temperature for 24 hours. Insoluble matter was removed by filtration, the organic layer was washed with acidified water, dried over anhydrous sodium sulfate and evaporated to dryness. The obtained residue was further chromatographed on silica gel (heptane) to afford 1.65 g of compound W18.4 (3.30 mmoles, MW=499.34, 79% yield).

Analysis of Compound W18.4:

TLC: Rf=0.90; solvent: heptane; detection with vanillin-sulfuric acid reagent (Merck TLC plates silica gel 60 $F_{254}$).

$^1$H-NMR (400 MHz, $CDCl_3$): δ=3.52 (t, J=6.7 Hz, 2H), 1.73 (quint, J=7.2 Hz, 2H), 1.45-1.05 (m, 57H), 0.86 (t, J=6.7 Hz, 6H).

b) Synthesis of W18.5

To 1.65 g of compound W18.4 (3.30 mmoles; MW=499.34) in 100 mL of acetone was added 1 g of sodium iodide (6.67 mmoles; MW=149.89). The mixture was refluxed under an argon atmosphere for 6 days. Solvent was removed under reduced pressure. The residue was dissolved in 100 mL of $CH_2Cl_2$, the solution was washed with acidified water, dried over anhydrous sodium sulfate and evaporated to dryness. The obtained residue was further chromatographed on silica gel (heptane) to afford 1.84 g of compound W18.5 (3.11 mmoles, MW=590.79, 94% yield).

Analysis of Compound W18.5:

TLC: Rf=0.90; solvent: heptane; detection with vanillin-sulfuric acid reagent and UV (Merck TLC plates silica gel 60 $F_{254}$).

$^1$H-NMR (400 MHz, $CDCl_3$): δ=3.17 (t, J=7.0 Hz, 2H), 1.78 (quint, J=7.1 Hz, 2H), 1.45-1.00 (m, 57H), 0.86 (t, J=6.7 Hz, 6H).

c) Synthesis of W18.6

A solution of 1.84 g of iodide W18.5 (3.11 mmoles; MW=590.79) in 10 mL of diethyl ether was added drop-wise to 0.15 g of magnesium turnings (6.17 mmoles; MW=24.31) in 5 mL of diethyl ether while heating. After 3 hours of reflux, the mixture was cooled to room temperature and 0.1 mL of ethyl formate (1.24 mmoles; MW=74.08) were added drop-wise. After 4 hours, the mixture was poured onto 100 mL of split ice, acidified with concentrated hydrochloric acid for 1 hour. The solid residue in suspension was filtered off and washed with water and was further chromatographed on silica gel ($CH_2Cl_2$-heptane 1:9) to afford 0.37 g of compound W18.6 (0.38 mmoles, MW=965.80, 30% yield).

d) Analysis of Compound W18.6

TLC: Rf=0.30; solvent: heptane; detection with vanillin-sulfuric acid reagent (Merck TLC plates silica gel 60 $F_{254}$).

$^1$H-NMR (400 MHz, $CDCl_3$): δ=8.07 (s, 1H), 4.96 (quint, J=6.1 Hz, 1H), 1.61-1.47 (m, 8H), 1.42-1.05 (m, 113H), 0.86 (t, J=6.9 Hz, 12H).

Analysis of Compound W18.9:

TLC: Rf=0.45; solvent: $CH_2Cl_2$-ethanol 9:1; detection with iodine (Merck TLC plates silica gel 60 $F_{254}$).

$^1$H-NMR (400 MHz, $CDCl_3$): δ=10.96 (s, 1H), 7.23-7.19 (m, 1H), 7.13-7.06 (m, 1H), 4.47-4.36 (m, 1H), 4.13 (s, 3H), 1.93-1.69 (m, 4H), 1.43-0.95 (m, 118H), 0.85 (t, J=6.7 Hz, 12H).

Example 16. Synthesis of W19.7: 1-methyl-3-(15-(octadecylammonio)pentacosan-11-yl)-1H-imidazol-3-ium chloride

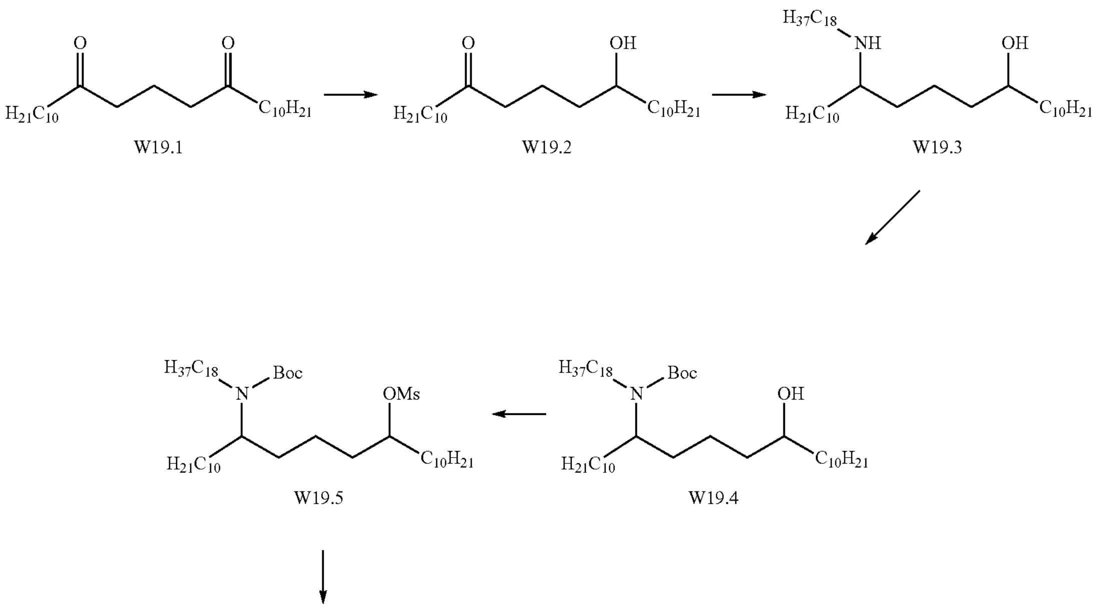

W19.1 W19.2 W19.3

W19.5 W19.4

-continued

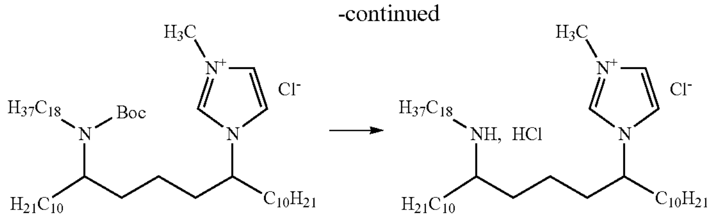

W19.6 W19.7 a) Synthesis of W19.1

To 5 mL of glutaryl chloride (39.17 mmoles; MW=169.01) in 100 mL of $CH_2Cl_2$ was added N,O-dimethylhydroxylamine hydrochloride (8.40 g; 86.11 mmoles; MW=97.54).

The mixture was cooled in an ice-water bath and 19 mL of pyridine (234.92 mmoles; MW=79.10) were added drop-wise. After 2 hours at room temperature, insoluble matter was removed by filtration and the filtrate was evaporated to dryness. The residue was resuspended in 100 mL of tetrahydrofuran, the mixture was cooled in an ice-water bath and 94 mL of decylmagnesium bromide solution 1 M in Diethyl ether (94.00 mmoles) were added drop-wise. After 2 hours, the mixture was poured onto 400 mL of split ice, acidified with concentrated hydrochloric acid for 1 hour. The solid residue in suspension was filtered off and washed with water and with ethyl acetate to afford 10.10 g of compound W19.1 (26.53 mmoles, MW=380.65, 68% yield).

Analysis of Compound W19.1:

TLC: Rf=0.45; solvent: $CH_2Cl_2$-heptane 1:1; detection with vanillin-sulfuric acid reagent (Merck TLC plates silica gel 60 $F_{254}$).

$^1$H-NMR (400 MHz, $CDCl_3$): δ=2.40 (t, J=7.2 Hz, 4H), 2.35 (t, J=7.5 Hz, 4H), 1.81 (quint, J=7.2 Hz, 2H), 1.56-1.46 (m, 4H), 1.34-1.14 (m, 28H), 0.85 (t, J=6.8 Hz, 6H).

b) Synthesis of W19.2

To 6.00 g of compound W19.1 (15.76 mmoles; MW=380.65) in 250 mL of tetrahydrofuran was added 2.40 g of sodium borohydride (63.42 mmoles; MW=37.83). After 3 hours at room temperature, solvent was removed under reduced pressure. The residue was resuspended in ethyl acetate and insoluble matter was removed by filtration. The organic layer was washed with water, dried over anhydrous sodium sulfate and evaporated to dryness. The obtained residue was further chromatographed on silica gel ($CH_2Cl_2$-methanol 98:2) to afford 0.88 g of compound W19.2 (2.30 mmoles, MW=382.66, 14% yield).

Analysis of Compound W19.2:

TLC: Rf=0.60; solvent: $CH_2Cl_2$-methanol 98:2; detection with vanillin-sulfuric acid reagent (Merck TLC plates silica gel 60 $F_{254}$).

$^1$H-NMR (400 MHz, $CDCl_3$): δ=3.58-3.48 (m, 1H), 2.45-2.32 (m, 4H), 1.48-1.15 (m, 38H), 0.86 (t, J=6.9 Hz, 6H).

c) Synthesis of W19.3

To 0.88 g of compound W19.2 (2.30 mmoles; MW=382.66) in 50 mL of tetrahydrofuran was added 0.68 g of octadecylamine (2.52 mmoles; MW=269.51) and 0.132 mL of acetic acid (2.30 mmoles, MW=60.05). After 1 hour at room temperature, 0.087 g of sodium borohydride (2.30 mmoles; MW=37.83) in 5 mL of water was added. The mixture was evaporated to dryness and the residue was further chromatographed on silica gel ($CH_2Cl_2$-methanol 9:1) to afford 0.48 g of compound W19.3 (0.75 mmole, MW=636.17, 32% yield).

Analysis of Compound W19.3:

TLC: Rf=0.50; solvent: $CH_2Cl_2$-methanol 9:1; detection with vanillin-sulfuric acid reagent or ninhydrin (Merck TLC plates silica gel 60 $F_{254}$).

$^1$H-NMR (400 MHz, $CDCl_3$): δ=3.62-3.52 (m, 1H), 3.03-2.88 (m, 1H), 2.88-2.72 (m, 2H), 1.76-1.10 (m, 74H), 0.86 (t, J=7.0 Hz, 9H).

d) Synthesis of W19.4

To 0.48 g of compound W19.3 (0.75 mmole; MW=636.17) in 30 mL of $CH_2Cl_2$ was added 1 mL of triethylamine (7.17 mmoles; MW=101.19) and 0.30 g of Di-tert-butyl dicarbonate (1.37 mmoles, MW=218.25). After 3 hours at room temperature, the organic layer was washed with water acidified with HCl, dried over anhydrous sodium sulfate and evaporated to dryness. 0.56 g of compound W19.4 were obtained without further purification (0.75 mmole, MW=736.29, quantitative yield).

Analysis of Compound W19.4:

TLC: Rf=0.25; solvent: $CH_2Cl_2$; detection with vanillin-sulfuric acid reagent (Merck TLC plates silica gel 60 $F_{254}$).

$^1$H-NMR (400 MHz, $CDCl_3$): δ=4.05-3.92 (m, 1H), 3.60-3.47 (m, 1H), 3.00-2.81 (m, 2H), 1.50-1.15 (m, 83H), 0.86 (t, J=6.8 Hz, 9H).

Compounds W19.5 and W19.6 were obtained following procedures similar to the ones described above (W21.6 and W21.7).

e) Synthesis of W19.7

0.10 g of compound W19.6 (0.12 mmole; MW=836.84) was treated with 1 mL of trifluoroacetic acid (13.06 mmoles; MW=114.02). After 1 hour at room temperature, the mixture was evaporated to dryness. The residue was dissolved in 2 mL of methanol and 0.5 mL of 37% hydrochloric acid and the mixture was evaporated to dryness. The residue was further chromatographed on silica gel ($CH_2Cl_2$-methanol 9:1) to afford 0.08 g of compound W19.7 (0.10 mmole, MW=773.18, 87% yield).

Analysis of Compound W19.7:

TLC: Rf=0.35; solvent: $CH_2Cl_2$-methanol 9:1; detection with vanillin-sulfuric acid reagent or ninhydrin (Merck TLC plates silica gel 60 $F_{254}$).

$^1$H-NMR (400 MHz, MeOD): δ=9.09 (s, 1H), 7.77-7.72 (m, 1H), 7.66-7.61 (m, 1H), 4.44-4.33 (m, 1H), 3.96 (s, 3H), 3.16-3.07 (m, 1H), 2.99-2.92 (m, 2H), 1.99-1.82 (m, 4H), 1.78-1.58 (m, 6H), 1.54-1.04 (m, 64H), 0.95-0.85 (m, 9H).

Example 17. Synthesis of W25.7: 1-(2-hydroxyethyl)-3-(24-tetradecyloctatriacontan-19-yl)-1H-imidazol-3-ium chloride

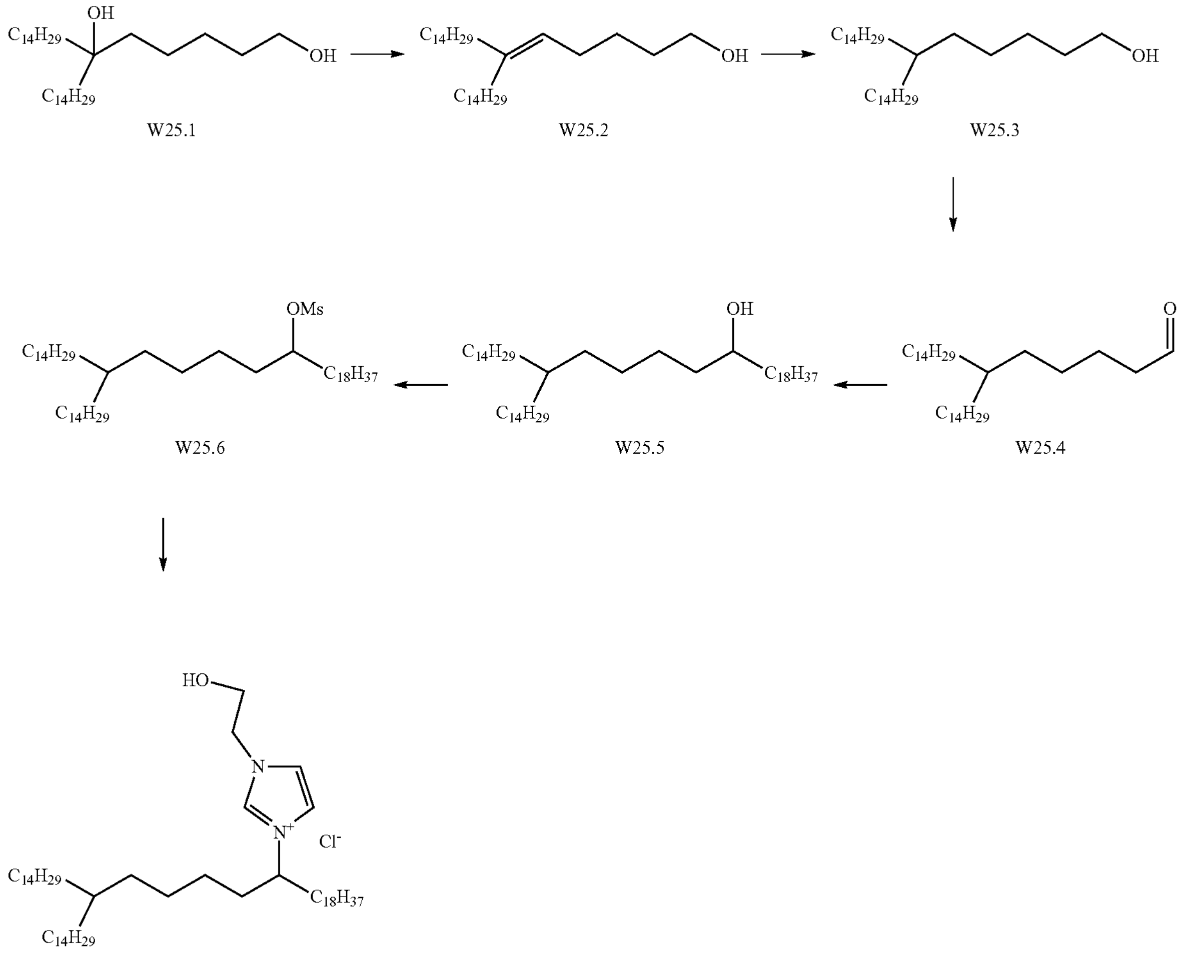

W25.1 W25.2 W25.3 W25.4 W25.5 W25.6 W25.7

Compounds W25.1 to W25.7 were obtained following procedures similar to the ones described above (W21.1 to W21.7).

Analysis of Compound W25.7:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=10.09 (s, 1H), 7.47 (t, J=1.8 Hz, 1H), 7.11 (t, J=1.8 Hz, 1H), 4.57 (t, J=4.4 Hz, 2H), 4.33-4.22 (m, 1H), 3.98 (t, J=4.4 Hz, 2H), 1.94-1.70 (m, 4H), 1.51-0.98 (m, 91H), 0.85 (t, J=6.8 Hz, 9H).

Example 18. Synthesis of W26.7: 1-(2-hydroxyethyl)-3-(20-tetradecyltetratriacontan-15-yl)-1H-imidazol-3-ium chloride

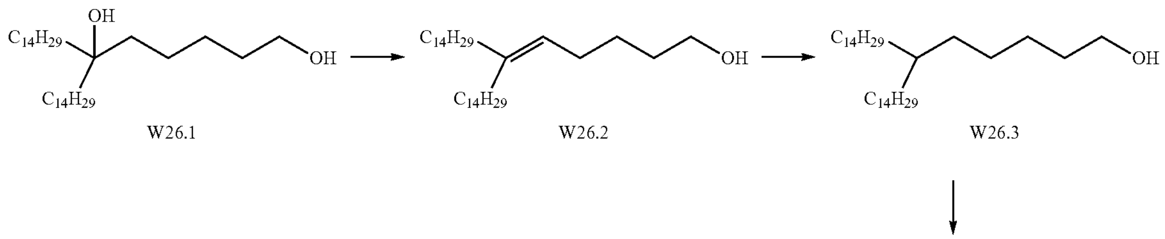

W26.1 W26.2 W26.3

-continued

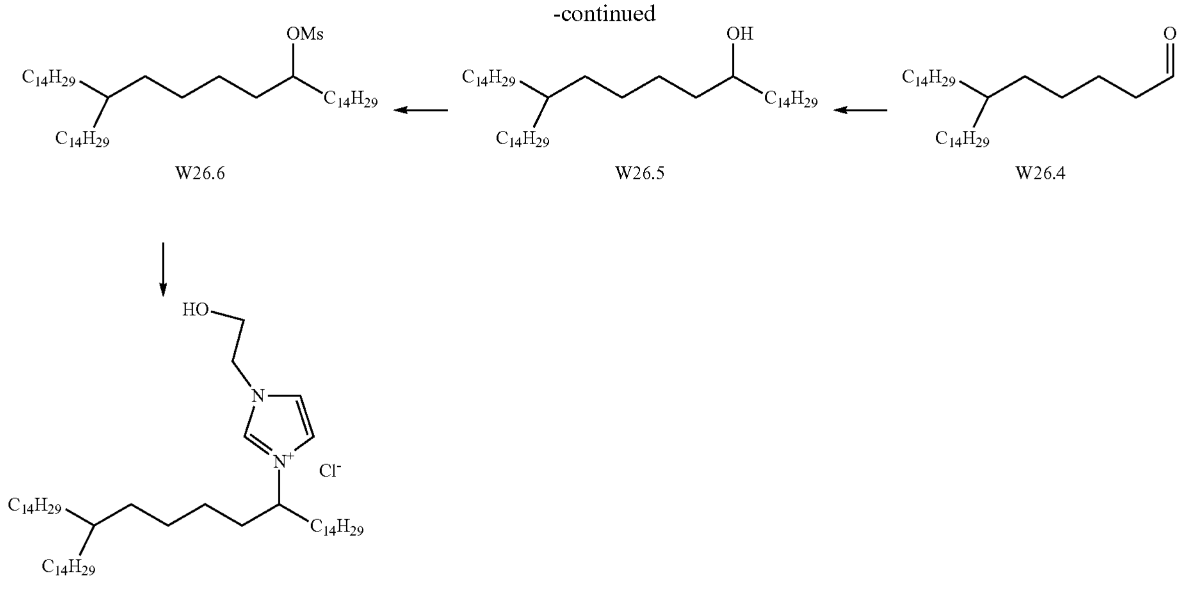

W26.6 W26.5 W26.4

W26.7

Compounds W26.1 to W26.7 were obtained following procedures similar to the ones described above (W21.1 to W21.7).

Analysis of Compound W26.7:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=11.05 (s, 1H), 7.27 (t, J=1.8 Hz, 1H), 7.11 (t, J=1.8 Hz, 1H), 4.47-4.37 (m, 1H), 4.13 (s, 3H), 1.93-1.70 (m, 4H), 1.48-0.95 (m, 83H), 0.91-0.77 (m, 9H).

Example 19. Synthesis of W27.7: 1-ethyl-3-(24-tetradecyloctatriacont-9-en-19-yl)-1H-imidazol-3-ium chloride

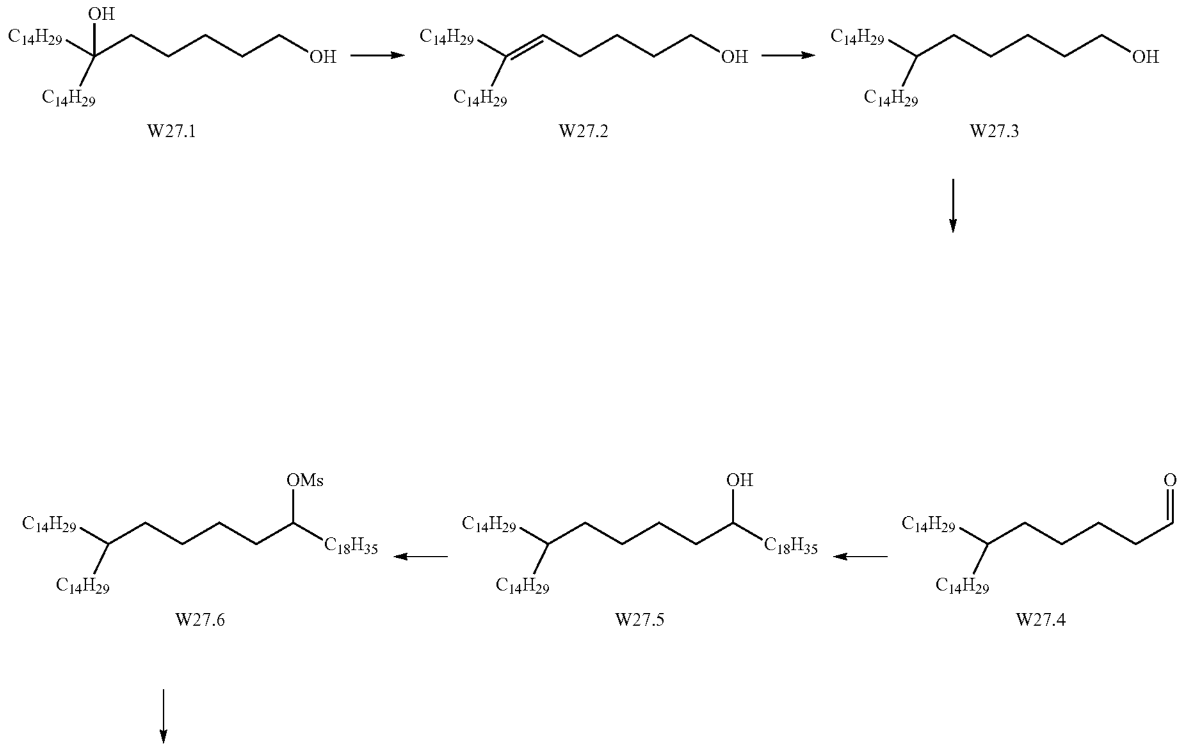

W27.1 W27.2 W27.3

W27.6 W27.5 W27.4

-continued

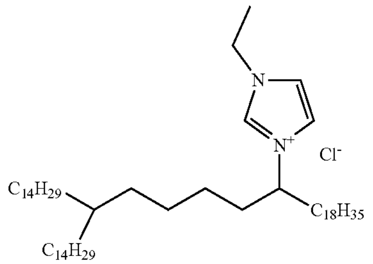

W27.7

Compounds W27.1 to W27.7 were obtained following procedures similar to the ones described above (W21.1 to W21.7).

Analysis of Compound W27.7:

TLC: Rf=0.4; solvent: $CH_2Cl_2$-methanol 9:1; detection with iodine (Merck TLC plates silica gel 60 $F_{254}$).

$^1$H-NMR (400 MHz, $CDCl_3$): δ=11.25 (s, 1H), 7.28 (t, J=1.6 Hz, 1H), 7.11 (t, J=1.6 Hz, 1H), 5.37-5.26 (m, 2H), 4.48 (q, J=7.3 Hz, 2H), 2.01-1.91 (m, 4H), 1.89-1.83 (m, 4H), 1.59 (t, J=7.3 Hz, 3H), 1.42-0.95 (m, 84H), 0.85 (t, J=6.8 Hz, 9H).

Example 20. Synthesis of W28.7: 1-methyl-3-(15-tetradecylheptatriacontan-19-yl)-1H-imidazol-3-ium chloride Compounds W28.1 to W28.7 were obtained following procedures similar to the ones described above (W21.1 to W21.7).

Analysis of Compound W28.7:

TLC: Rf=0.4; solvent: $CH_2Cl_2$-methanol 9:1; detection with iodine (Merck TLC plates silica gel 60 $F_{254}$).

$^1$H-NMR (400 MHz, $CDCl_3$): δ=11.15 (s, 1H), 7.24 (t, J=1.5 Hz, 1H), 7.10 (t, J=1.5 Hz, 1H), 4.45-4.36 (m, 1H), 4.14 (s, 3H), 1.91-1.79 (m, 4H), 1.43-0.99 (m, 89H), 0.85 (t, J=6.8 Hz, 9H).

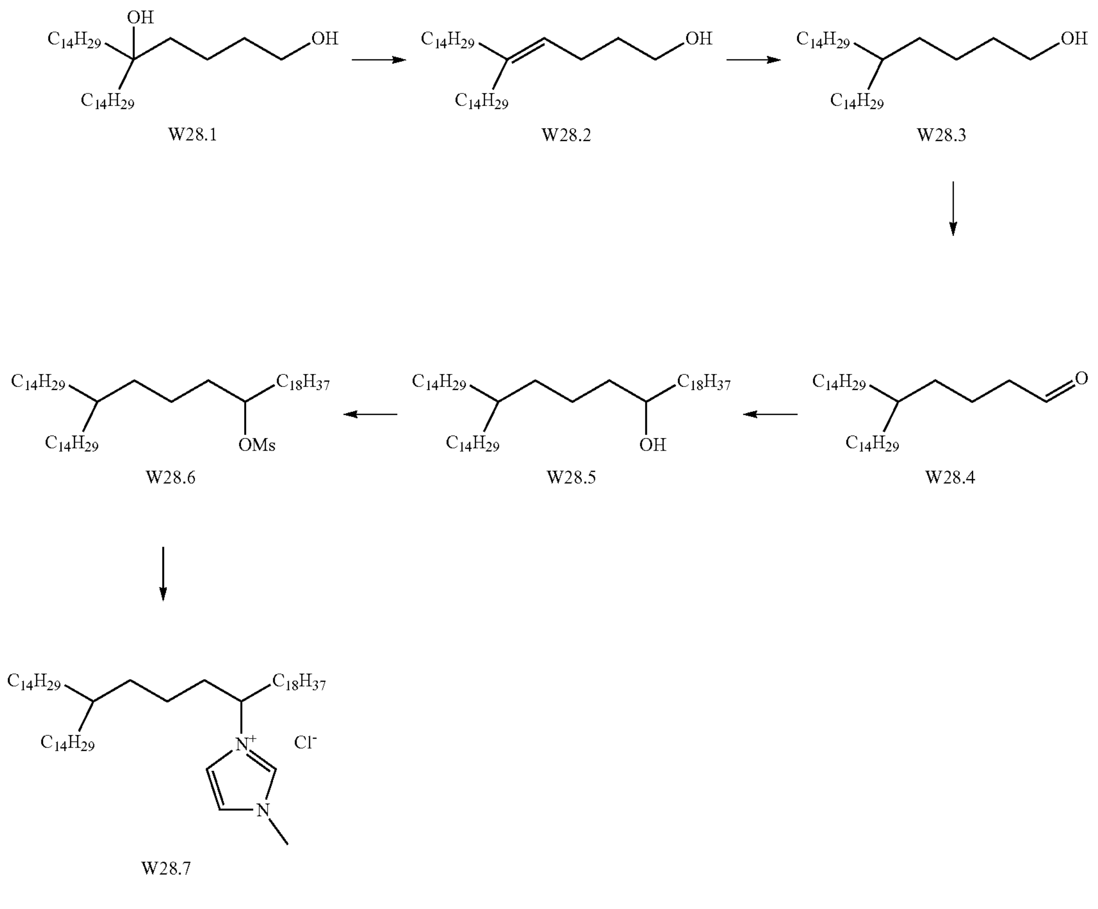

Example 21. Synthesis of W29.5: 1-methyl-3-(4-hexadecylicosyl)-1H-imidazol-3-ium chloride

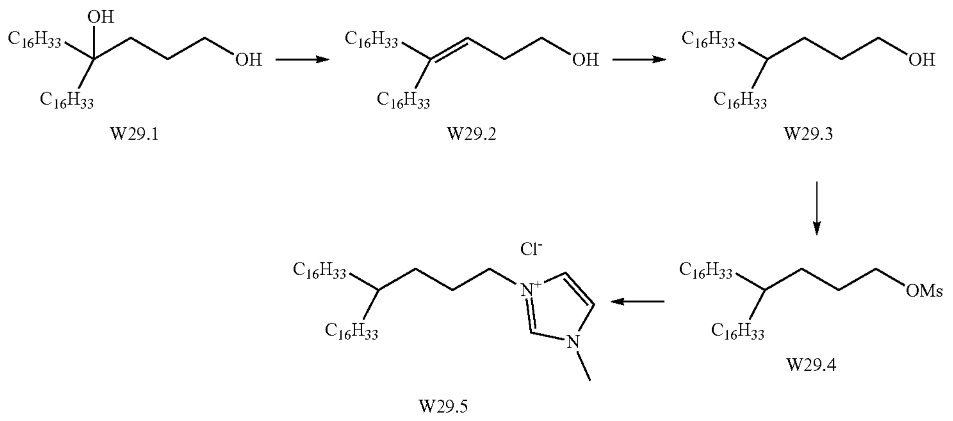

Compounds W29.1 to W29.5 were obtained following procedures similar to the ones described above (W21.1 to W21.3 and W21.5 to W21.7).

Analysis of Compound W29.5:

TLC: Rf=0.43; solvent: $CH_2Cl_2$-methanol 9:1; detection with vanillin-sulfuric acid reagent (Merck TLC plates silica gel 60 $F_{254}$).

$^1$H-NMR (400 MHz, $CDCl_3$): δ=10.65 (s, 1H), 7.49 (s, 1H), 7.28 (s, 1H), 4.27 (t, J=7.5 Hz, 2H), 4.12 (s, 3H), 1.85 (q, J=6.1 Hz, 2H), 1.24 (s, 1H), 1.19-1.24 (m, 66H).

Example 22. Synthesis of W8.7: 1-methyl-3-(hexatriaconta-8,27-dien-18-yl)-1H-imidazol-3-ium

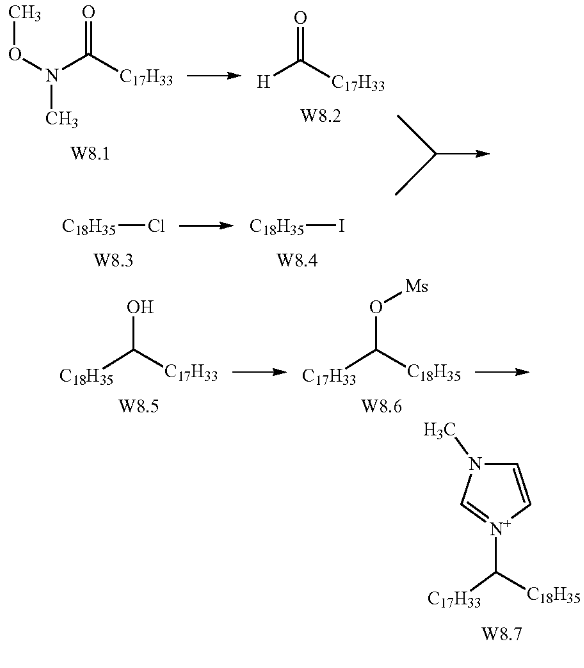

a) Synthesis of Amide W8.1

To a solution of 3 mL Pyridine (2.93 g; 37.09 mmoles; MW=79.10) and 1.80 g of N,O-dimethylhydroxylamine hydrochloride (19.48 mmoles; MW=97.54) in 50 mL of $CH_2Cl_2$ cooled in an ice-water bath was added drop-wise 5.5 mL of oleoyl chloride (5.00 g; 16.63 mmoles; MW=300.91). The mixture was allowed to stay at room temperature for 1 hour. The solvents were removed under reduced pressure to give a crude that was purified with liquid/liquid partition (ethyl acetate/water) to give 5.46 g of pure amide W8.1 (16.77 mmoles; MW=325.53; quantitative yield).

Analysis of Compound W8.1:

TLC: Rf=0.3; solvent: $CH_2Cl_2$; detection with iodine (Merck TLC plates silica gel 60 $F_{254}$).

$^1$H-NMR (400 MHz, $CDCl_3$): δ=5.35-5.29 (m, 2H), 3.66 (s, 3H), 3.15 (s, 3H), 2.38 (t, J=7.5 Hz, 2H), 1.98 (q, J=6.1 Hz, 4H), 1.60 (quint, J=7.5 Hz, 2H), 1.37-1.18 (m, 20H), 0.86 (t, J=6.9 Hz, 3H).

b) Synthesis of Aldehyde W8.2

To a solution of 1 g of amide W8.1 (3.07 mmoles; MW=325.53) in 20 mL of $CH_2Cl_2$ cooled in a dry ice bath was added drop-wise 6.7 mL of diisobutylaluminum hydride solution at 1M in cyclohexane (6.70 mmoles). 5 hours later, 10 mL of methanol were added and the mixture was allowed to stay at room temperature overnight. The solvents were removed under reduced pressure to give a crude that was purified with liquid/liquid partition (diethyl ether/water) followed by chromatography on silica gel ($CH_2Cl_2$-cyclohexane 2:8) to afford 0.25 g of aldehyde W8.2 (0.93 mmole; MW=266.46; 31% yield).

Analysis of Compound W8.2:

TLC: Rf=0.3; solvent: $CH_2Cl_2$-cyclohexane 3:7; detection with iodine (Merck TLC plates silica gel 60 $F_{254}$).

$^1$H-NMR (400 MHz, $CDCl_3$): δ=9.74 (t, J=1.9 Hz, 1H), 5.39-5.27 (m, 2H), 2.40 (td, J=7.4 Hz, 1.9 Hz, 2H), 1.99 (q, J=5.8 Hz, 4H), 1.61 (quint, J=7.4 Hz, 2H), 1.38-1.18 (m, 20H), 0.86 (t, J=6.8 Hz, 3H).

c) Synthesis of Chloride W8.3

To a solution of 3.78 g of cyanuric chloride (20.50 mmoles; MW=184.41) in 10 mL of dimethylformamide was added a solution of 5 g of oleyl alcohol (18.62 mmoles; MW=268.48) in 50 mL of $CH_2Cl_2$. The mixture was allowed to stay overnight at room temperature. The mixture was poured onto 100 mL of split ice. After liquid/liquid partition and removal of solvents, the crude was chromatographed on silica gel ($CH_2Cl_2$-cyclohexane 1:9) to afford 3.00 g of chloride W8.3 (10.46 mmoles; MW=286.92; 56% yield).

Analysis of Chloride W8.3:

$^1$H-NMR (400 MHz, $CDCl_3$): δ=5.40-5.26 (m, 2H), 3.51 (t, J=6.8 Hz, 2H), 2.08-1.90 (m, 4H), 1.75 (quint, J=7.2 Hz, 2H), 1.40 (quint, J=6.8 Hz, 2H), 1.40-1.18 (m, 20H), 0.86 (t, J=6.8 Hz, 3H).

d) Synthesis of Iodide W8.4

To a solution of 3.00 g of chloride W8.3 (10.46 mmoles; MW=286.92) in 100 mL of acetone was added 3.14 g of sodium iodide (20.95 mmoles; MW=149.89). The mixture was refluxed during 4 days. After removal of insoluble matter by filtration, solvents were removed and the crude was chromatographed on silica gel (cyclohexane) to afford 3.76 g of iodide W8.4 (9.94 mmoles; MW=378.37; 95% yield).

Analysis of Iodide W8.4:

$^1$H-NMR (400 MHz, $CDCl_3$): δ=5.42-5.26 (m, 2H), 3.17 (t, J=7.1 Hz, 2H), 2.06-1.90 (m, 4H), 1.80 (quint, J=7.1 Hz, 2H), 1.46-1.16 (m, 22H), 0.86 (t, J=6.8 Hz, 3H). Traces of chloride W8.3 (10%) are remaining.

e) Synthesis of Alcohol W8.5

A solution of 1.10 g of iodide W8.4 (2.91 mmoles; MW=378.37) in 5 mL of diethyl ether was added drop-wise to 0.10 g of magnesium turnings (4.11 mmoles; MW=24.31) in 5 mL of diethyl ether while heating. After 2 hours of reflux, the mixture was cooled to room temperature and 0.50 g of aldehyde W8.2 (1.88 mmoles; MW=266.46) in 10 mL of diethyl ether were added drop-wise. After 4 hours, the mixture was poured onto 100 mL split, ice acidified with concentrated hydrochloric acid for 1 hour. After extraction with ethyl acetate and removal of solvents, the crude was chromatographed on silica gel ($CH_2Cl_2$-cyclohexane 3:7) to afford 0.27 g of alcohol W8.5 (0.52 mmole; MW=518.94; 27% yield).

Analysis of Alcohol W8.5:

TLC: Rf=0.15; solvent: $CH_2Cl_2$-cyclohexane 3:7; detection with iodine (Merck TLC plates silica gel 60 $F_{254}$).

$^1$H-NMR (400 MHz, $CDCl_3$): δ=5.42-5.27 (m, 4H), 3.60-3.51 (m, 1H), 2.17-1.82 (m, 8H), 1.50-1.06 (m, 50H), 0.86 (t, J=6.8 Hz, 6H).

f) Synthesis of Mesylate W8.6

Alcohol W8.5 (0.27 g; 0.52 mmole; MW=518.94) was dissolved in 15 mL of dry $CH_2Cl_2$ and 0.75 mL of triethylamine (0.54 g; 5.38 mmoles; MW=101.19) were added, followed by 0.33 mL of methanesulfonyl chloride (0.49 g; 4.26 mmoles; MW=114.55) introduced drop-wise. The mixture was stirred overnight at room temperature. After removal of the solvents under reduced pressure, the residue was resuspended in 20 mL of methanol. After decantation of the solvents, 0.26 g of mesylate W8.6 were obtained (0.44 mmole, MW=597.03, 84% yield).

Analysis of Mesylate W8.6:

$^1$H-NMR (400 MHz, $CDCl_3$): δ=5.41-5.26 (m, 4H), 4.68 (quint, J=6.1 Hz, 1H), 2.97 (s, 3H), 2.09-1.90 (m, 8H), 1.75-1.58 (m, 4H), 1.47-1.07 (m, 46H), 0.86 (t, J=6.8 Hz, 6H).

g) Synthesis of Compound W8.7

Mesylate W8.6 (0.26 g; 0.44 mmole; MW=597.03) was dissolved in 10 mL of 1-methylimidazole and was stirred at 80° C. for 5 days under an argon atmosphere. The mixture was evaporated to dryness under high vacuum, the residue was then solubilized in 20 mL of methanol and 10 mL of a 3 M hydrochloric acid was added. After removal of solvents, the crude was chromatographed on silica gel ($CH_2Cl_2$-methanol 9:1) to afford 0.13 g of compound W8.7 (0.21 mmole, MW=619.49, 48% yield).

Analysis of Compound W8.7:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=10.96 (s, 1H), 7.29 (t, J=1.6 Hz, 1H), 7.11 (t, J=1.6 Hz, 1H), 5.40-5.24 (m, 4H), 4.46-4.35 (m, 1H), 4.12 (s, 3H), 2.03-1.89 (m, 8H), 1.88-1.71 (m, 4H), 1.36-0.96 (m, 46H), 0.85 (t, J=6.8 Hz, 6H).

Example 23. Synthesis of W2.5: 1-methyl-3-(heptatriaconta-9,28-dien-19-yl)-1H-imidazol-3-ium chloride

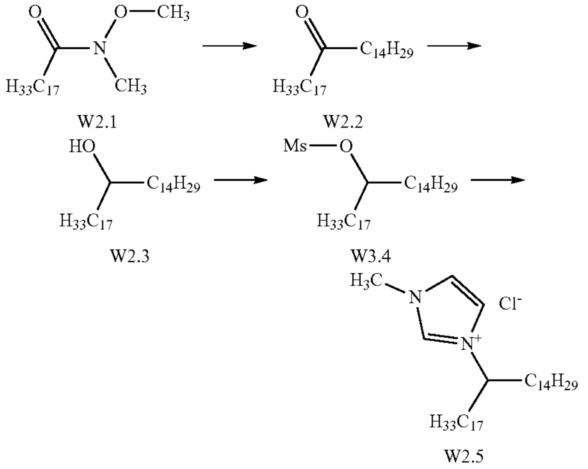

W2.1 W2.2 W2.3 W3.4 W2.5

Compounds W2.1 to W2.5 were obtained following procedures similar to the ones described above (W8.1, W8.5, W19.2, W21.6 and W21.7 respectively).

Analysis of Compound W2.5:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=11.02 (s, 1H), 7.38 (t, J=1.6 Hz, 1H), 7.13 (t, J=1.6 Hz, 1H), 5.36-5.24 (m, 2H), 4.45-4.35 (m, 1H), 4.12 (s, 3H), 2.05-1.89 (m, 4H), 1.89-1.70 (m, 4H), 1.35-0.95 (m, 48H), 0.84 (t, J=6.7 Hz, 6H).

Example 24. Synthesis of W3.5: 1-methyl-3-(hexatriacont-8-en-18-yl)-1H-imidazol-3-ium chloride

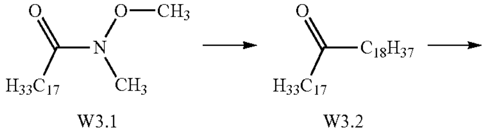

W3.1 W3.2

-continued

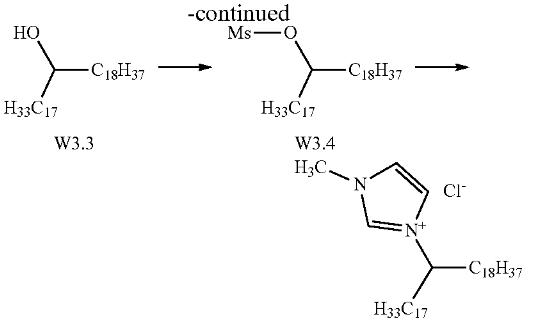

W3.3 W3.4 W3.5

Compounds W3.1 to W3.5 were obtained following procedures similar to the ones described above (W8.1, W8.5, W19.2, W21.6 and W21.7 respectively).

Analysis of Compound W3.5:

TLC: Rf=0.25; solvent: $CH_2Cl_2$-methanol 9:1; detection with iodine (Merck TLC plates silica gel 60 $F_{254}$).

$^1$H-NMR (400 MHz, $CDCl_3$): δ=11.12 (s, 1H), 7.29 (t, J=1.6 Hz, 1H), 7.11 (t, J=1.6 Hz, 1H), 5.36-5.24 (m, 2H), 4.46-4.36 (m, 1H), 4.13 (s, 3H), 2.05-1.90 (m, 4H), 1.90-1.70 (m, 4H), 1.40-0.95 (m, 56H), 0.85 (t, J=6.8 Hz, 6H).

Example 25. Synthesis of W4.3: 1-methyl-3-(nonacosan-15-yl)-1H-imidazol-3-ium chloride

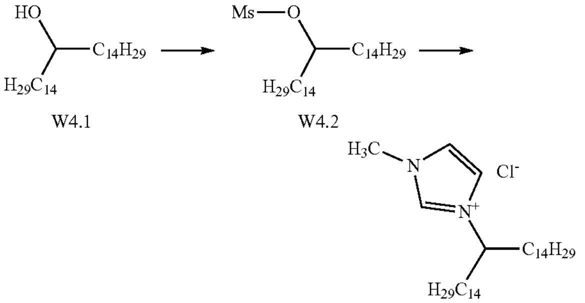

W4.1 W4.2 W4.3

Compounds W4.1 to W4.3 were obtained following procedures similar to the ones described above (W21.1, W21.6 and W21.7 respectively).

Analysis of Compound W4.3:

$^1$H-NMR (400 MHz, $CDCl_3$): δ=11.15 (s, 1H), 7.37 (t, J=1.6 Hz, 1H), 7.17 (t, J=1.6 Hz, 1H), 4.50-4.40 (m, 1H), 4.18 (s, 3H), 2.05-1.90 (m, 4H), 1.40-0.95 (m, 48H), 0.85 (t, J=6.8 Hz, 6H).

Example 26. Synthesis of W5.3: 1-methyl-3-(tritriacontan-17-yl)-1H-imidazol-3-ium chloride

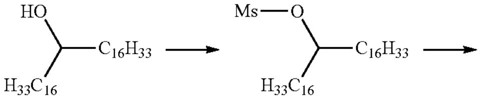

W5.1 W5.2

-continued

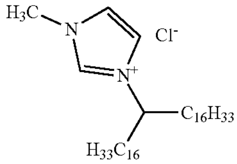

W5.3

Compounds W5.1 to W5.3 were obtained following procedures similar to the ones described above (W21.1, W21.6 and W21.7 respectively).

Analysis of Compound W5.3:

$^1$H-NMR (400 MHz, $CDCl_3$): δ=11.15 (s, 1H), 7.32 (t, J=1.6 Hz, 1H), 7.16 (t, J=1.6 Hz, 1H), 4.50-4.40 (m, 1H), 4.18 (s, 3H), 2.00-1.85 (m, 4H), 1.40-0.95 (m, 56H), 0.85 (t, J=6.8 Hz, 6H).

Example 27. Synthesis of W7.4: 1-methyl-3-(2-heptadecylicosyl)-1H-imidazol-3-ium chloride

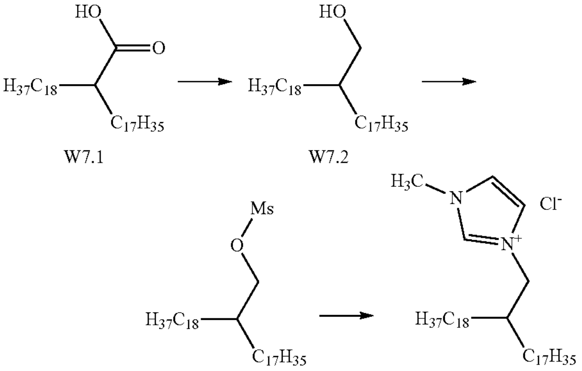

W7.1 W7.2 W7.3 W7.4 a) Synthesis of Compound W7.1

To a solution of lithium diisopropylamide (3.59 g; 33.51 mmoles; MW=107.12) in 100 mL of tetrahydrofuran cooled in an ice-water bath was added drop-wise a solution of 10 g of nonadecanoic acid (33.50 mmoles; MW=298.50) in 100 mL of tetrahydrofuran. 4.8 mL of 1,3-dimethyl-3,4,5,6-tetrahydro-2(1H)-pyrimidinone (39.70 mmoles; MW=128.17) were then added. The reaction mixture was allowed to stay 30 minutes at room temperature. The mixture was then cooled at −10° C. and 12.74 g of 1-Iodooctadecane (33.50 mmoles; MW=380.39) in 80 mL of tetrahydrofuran were added drop-wise. After 24 hours at room temperature, the mixture was poured onto 400 mL split ice acidified with 150 mL of concentrated hydrochloric acid for 1 hour. After extraction with ethyl acetate and removal of solvents, the crude was chromatographed on silica gel ($CH_2Cl_2$-heptane 1:1). The residue was further recrystallized from acetone to afford 4.66 g of compound W7.1 (8.46 mmoles, MW=550.98, 25% yield).

Analysis of Compound W7.1:

TLC: Rf=0.20; solvent: $CH_2Cl_2$-heptane 1:1; detection with vanillin-sulfuric acid reagent (Merck TLC plates silica gel 60 $F_{254}$).

$^1$H-NMR (400 MHz, $CDCl_3$): δ=2.42-2.32 (m, 1H), 1.70-1.52 (m, 2H), 1.52-1.38 (m, 2H), 1.35-1.00 (m, 62H), 0.85 (t, J=6.8 Hz, 6H).

b) Synthesis of Compound W7.2

To a solution of 4.50 g of compound W7.1 (8.17 mmoles; MW=550.98) in 100 mL of tetrahydrofuran cooled in an ice-water bath was added drop-wise 64 mL of a 1 M Borane tetrahydrofuran complex solution in Tetrahydrofuran (64 mmoles; MW=85.94). After 24 hours at room temperature, the mixture was poured onto 400 mL of methanol and the solvents were removed under reduced pressure. The residue was chromatographed on silica gel ($CH_2Cl_2$-heptane 3:7) to afford 3.58 g of compound W7.2 (6.67 mmoles, MW=537.00, 81% yield).

Analysis of Compound W7.2:

TLC: Rf=0.50; solvent: $CH_2Cl_2$-heptane 1:1; detection with vanillin-sulfuric acid reagent (Merck TLC plates silica gel 60 $F_{254}$).

$^1$H-NMR (400 MHz, $CDCl_3$): δ=3.56 (m, 2H), 1.40-1.00 (m, 67H), 0.85 (t, J=6.8 Hz, 6H).

c) Syntheses of Compounds W7.3 and W7.4

Compounds W7.3 and W7.4 were obtained following procedures similar to the ones described above (W21.6 and W21.7).

Analysis of Compound W7.4:

$^1$H-NMR (400 MHz, $CDCl_3$): δ=10.78 (s, 1H), 7.43 (t, J=1.6 Hz, 1H), 7.17 (t, J=1.6 Hz, 1H), 4.30-4.00 (m, 5H), 1.40-0.95 (m, 67H), 0.88 (t, J=6.8 Hz, 6H).

Example 28. Synthesis of W1.4: 1-methyl-3-(heptatriaconta-9,28-dien-19-yl)-1-methyl-1H-imidazol-3-ium chloride

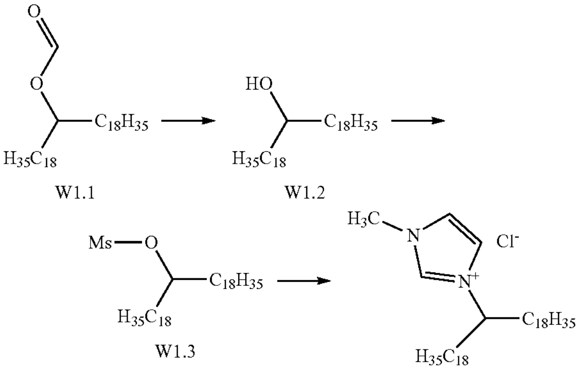

W1.1 W1.2 W1.3 W1.4

Compounds W1.1 to W1.4 were obtained following procedures similar to the ones described above (W18.6, W18.7, W21.6 and W21.7 respectively).

Analysis of Compound W1.4:

TLC: Rf=0.50; solvent: $CH_2Cl_2$-methanol 9:1; detection with iodine (Merck TLC plates silica gel 60 $F_{254}$).

$^1$H-NMR (400 MHz, $CDCl_3$): δ=10.90 (s, 1H), 7.30 (t, J=1.6 Hz, 1H), 7.17 (t, J=1.6 Hz, 1H), 5.40-5.20 (m, 4H), 4.40-4.20 (m, 1H), 4.10 (s, 3H), 2.00-1.60 (m, 12H), 1.40-0.95 (m, 48H), 0.85 (t, J=6.8 Hz, 6H).

Example 29. Synthesis of W6.3: 1-methyl-3-(nonacosan-11-yl)-1H-imidazol-3-ium chloride

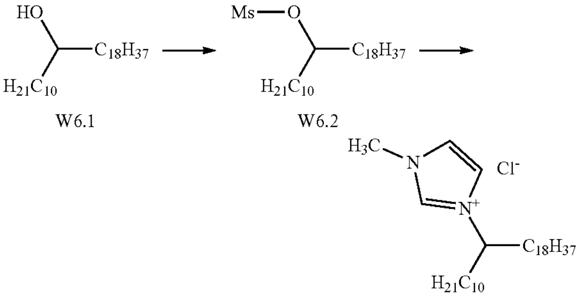

W6.1 W6.2 W6.3

Compounds W6.1 to W6.3 were obtained following procedures similar to the ones described above (W21.1, W21.6 and W21.7 respectively).

Analysis of Compound W6.3:

$^1$H-NMR (400 MHz, $CDCl_3$): δ=10.90 (s, 1H), 7.50 (t, J=1.6 Hz, 1H), 7.20 (t, J=1.6 Hz, 1H), 4.45-4.35 (m, 1H), 4.20 (s, 3H), 2.00-1.60 (m, 4H), 1.40-0.95 (m, 48H), 0.85 (t, J=6.8 Hz, 6H).

Example 30. mRNA EGFP Transfection

All these new liposomal formulations (Table 1) were assessed to deliver mRNA expressing an enhanced green fluorescent protein (eGFP) as reporter gene in order to determine the gene expression and the transfection efficiency (Table 2). mRNA eGFP capped with a Cap 0 in 5'-end, polyadenylated in 3'-end and modified with 5-methylcytidine and pseudo-uridine was used in the transfection assay. The transfection assay was performed as described in the Experimental section where 150 ng of mRNA eGFP was complexed with 1 μL of 1 mM cationic liposomal formulations in a 5% glucose solution before the addition on the cells. One day post-transfection, the eGFP expression was analyzed by flow cytometry to determine the percentage of transfection. Four different cell lines were used in this assay from easy to transfect cells to hard to transfect cells with plasmid DNA, including human BJ skin fibroblast cells, THP-1 human peripheral blood monocytes, Caco-2 human colon epithelial cells and Jurkat Clone E6-1 human T lymphoblast cells, respectively.

Methyl-imidazolium based lipids ($R_1$=$CH_3$) were synthesized with an absence of the alkyl linker $(CH_2)_n$, n=0, with $R_2$ and $R_4$ being saturated or unsaturated alkyl chains, $C_{14}$-$C_{18}$, and $C_9$-$C_{17}$, respectively (W1.4, W2.5, W3.5, W4.3, W5.3, W6.3, W7.4, W8.7). All these lipids contained two lipophilic chains and were formulated with DOPE (ratio 1:2). These formulations were able to transfect efficiently BJ cells (50-95% GFP positive cells) and THP-1 cells (30-90% GFP positive cells) and showed a moderate transfection activity in CaCo2 cells (5-40% GFP) whereas the transfection efficiency in Jurkat cells was relatively low (0-25% GFP). A trend of reduced transfection activity was also observed when the length of alkyl chains $R_2$ and $R_4$ was reduced (W4.3, W5.3).

Methyl-imidazolium based lipids ($R_1$=$CH_3$) were synthesized with the presence of the alkyl linker $(CH_2)_n$, with n=4, with $R_2$ being saturated or unsaturated linear or branched hydrocarbon chain, saturated or unsaturated $C_6$ cycle, and $R_3$ and $R_4$ being saturated or unsaturated alkyl chains (W9.7, W10.7, W11.7, W12.7, W13.7, W14.7, W15.7, W16.7, W17.7, W18.9). This group of lipids contained a ramified structure having three lipophilic chains. After formulation with the co-lipid DOPE, the transfection activity was evaluated. Surprisingly, the transfection efficiency was increased in the most difficult to transfect cells, Jurkat and CaCo2, and remained very active in the other cells. It appeared also that when $R_2$ was $C_{10}H_{21}$ branched alkyl chain, a high transfection activity was obtained.

Butyl-imidazolium based lipids ($R_1$=$CH_2$—$CH_2$—$CH_2$—$CH_3$) were synthesized with the presence of the alkyl linker $(CH_2)_n$, with n=4, with $R_2$ being saturated or unsaturated alkyl chains, and $R_3$ and $R_4$ being saturated or unsaturated alkyl chains (W20.7, W21.7, W22.7, W23.7). After formulation with a co-lipid DOPE or DPyPE, the transfection activity was evaluated and was found very active and consistently efficient. Particularly, the transfection activity in Jurkat cells was remarkable.

Other variations were introduced in the imidazolium lipid structure like $R_1$ being hydroxyethyl (W25.7, W26.7) or ethyl (W27.7), and like the linker $(CH_2)_n$ with n=3 (W29.5, W28.7) without really affecting the transfection activity at the end. However, when $R_1$ is H (W24.7), the resulting formulation was found not active in transfection whatever the co-lipid used, DOPE or DPyPE.

Figure 3:
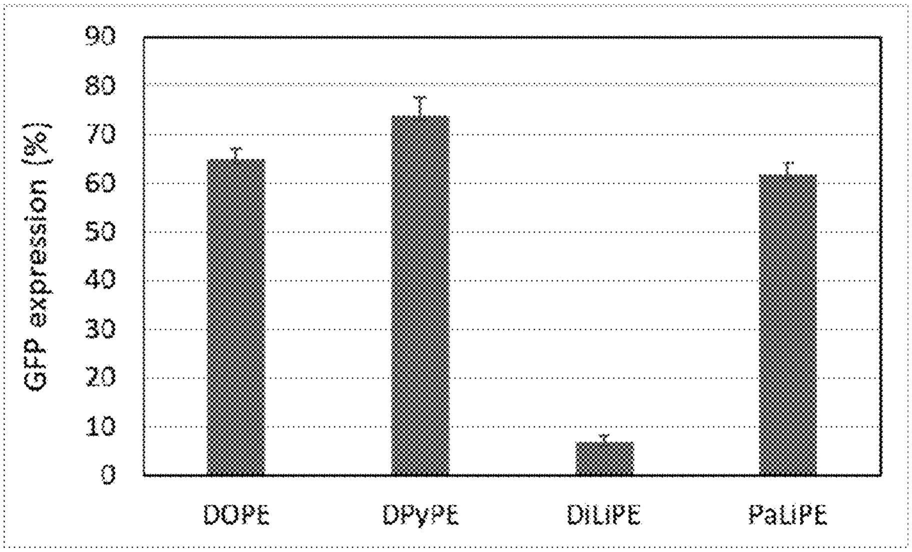
FIG. 3. Graph showing the transfection efficiency of $CaCO_2$ cells with eGFP mRNA with the compound W9.7 formulated with different co-lipids at a molar ratio of 1:2. The eGFP expression was determined 24 hours after transfection.

Many compounds were formulated with different co-lipids, mainly DOPE or DPyPE, without significant impact on the transfection activity. However, the choice of the co-lipid may interfere the transfection activity in a particular cell type. This is exemplified in the FIG. 3 with the compound W9 which was formulated with different co-lipids including DOPE, DPyPE, PaLIPE or DiLiPE. The CaCo2 cells were transfected with eGFP mRNA and the GFP expression one day post-transfection was found optimal with the DPyPE as co-lipid of W9. The formulation with DPyPE as co-lipid with most of the compounds tested was found optimal to transfect the four cell lines tested.

TABLE 1
Chemical structures of imidazole- and imidazolium-based compounds
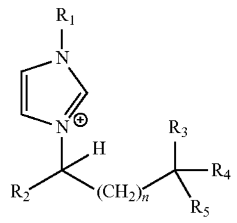
| Compound | $R_1$ | $(CH_2)_n$ n= | $R_2$ | $R_3$ | $R_4$ | $R_5$ | |
|---|---|---|---|---|---|---|---|
| W1.4 | $CH_3$ | 0 | $C_{18}H_{35}$ | H | $C_{17}H_{33}$ | H | 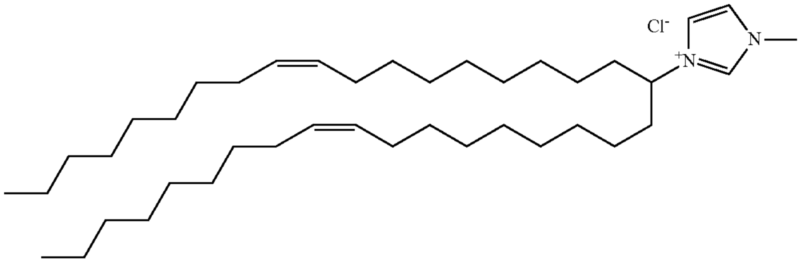 |
| W2.5 | $CH_3$ | 0 | $C_{14}H_{29}$ | H | $C_{16}H_{31}$ | H | 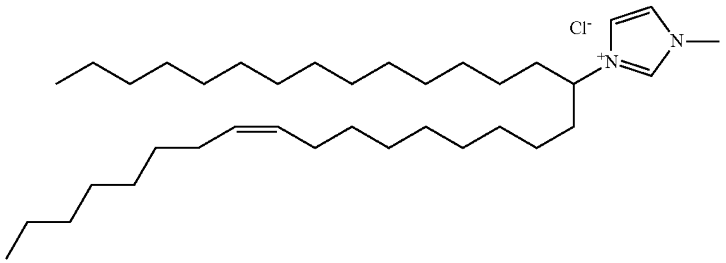 |

TABLE 1-continued
Chemical structures of imidazole- and imidazolium-based compounds
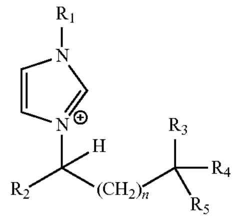
| Compound | $R_1$ | $(CH_2)_n$ n= | $R_2$ | $R_3$ | $R_4$ | $R_5$ | |
|---|---|---|---|---|---|---|---|
| W3.5 | $CH_3$ | 0 | $C_{18}H_{37}$ | H | $C_{16}H_{31}$ | H | 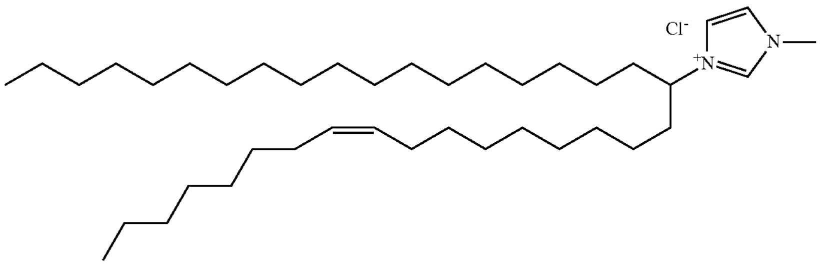 |
| W4.3 | $CH_3$ | 0 | $C_{14}H_{19}$ | H | $C_{13}H_{27}$ | H | 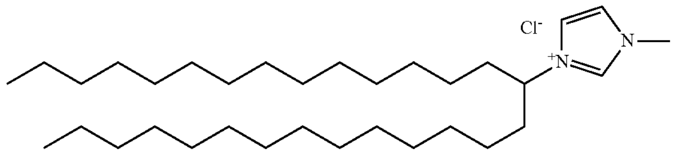 |
| W5.3 | $CH_3$ | 0 | $C_{16}H_{33}$ | H | $C_{15}H_{31}$ | H | 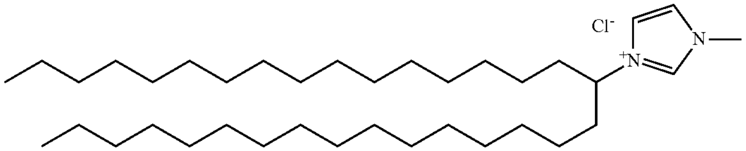 |
| W6.3 | $CH_3$ | 0 | $C_{18}H_{37}$ | H | $C_9H_{19}$ | H | 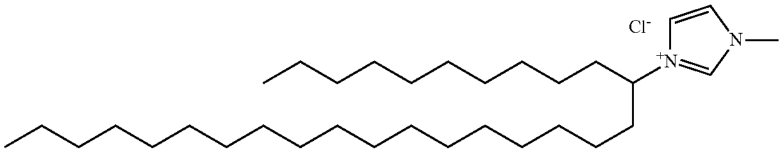 |

TABLE 1-continued
Chemical structures of imidazole- and imidazolium-based compounds
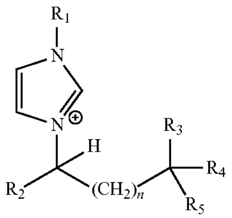
| Com-pound | $R_1$ | $(CH_2)_n$ n= | $R_2$ | $R_3$ | $R_4$ | $R_5$ | |
|---|---|---|---|---|---|---|---|
| W7.4 | $CH_3$ | 0 | H | $C_{17}H_{35}$ | $C_{17}H_{35}$ | H | 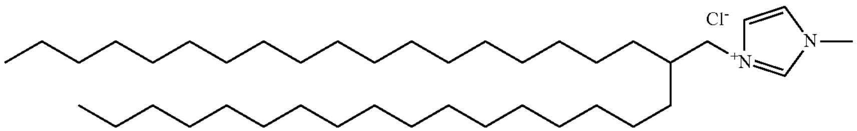 |
| W8.7 | $CH_3$ | 0 | $C_{17}H_{33}$ | H | $C_{17}H_{33}$ | H | 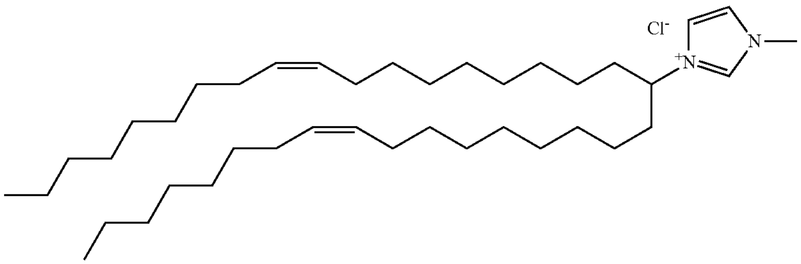 |
| W9.7 | $CH_3$ | 4 | $C_{14}H_{29}$ | $C_{14}H_{29}$ | $C_{14}H_{29}$ | H | 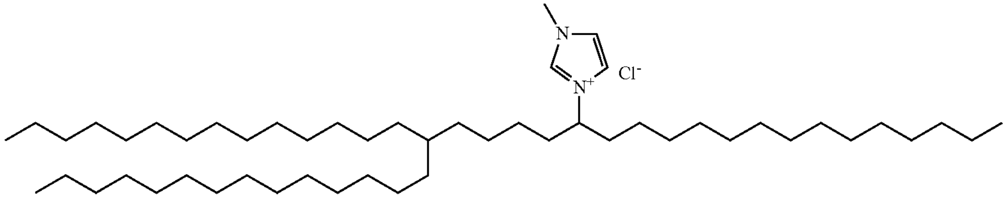 |
| W10.7 | $CH_3$ | 4 | $C_{18}H_{35}$ | $C_{14}H_{29}$ | $C_{14}H_{29}$ | H | 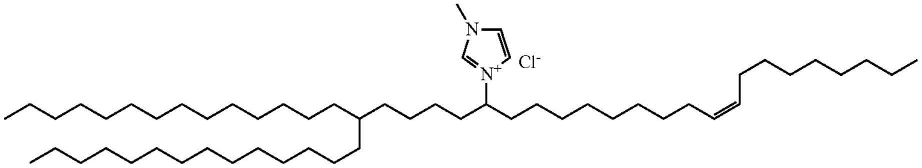 |

TABLE 1-continued
Chemical structures of imidazole- and imidazolium-based compounds
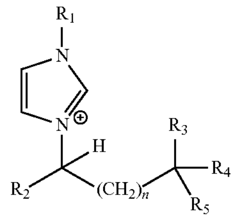
| Compound | $R_1$ | $(CH_2)_n$ n= | $R_2$ | $R_3$ | $R_4$ | $R_5$ | |
|---|---|---|---|---|---|---|---|
| W11.7 | $CH_3$ | 4 | $C_{18}H_{37}$ | $C_{14}H_{29}$ | $C_{14}H_{29}$ | H | 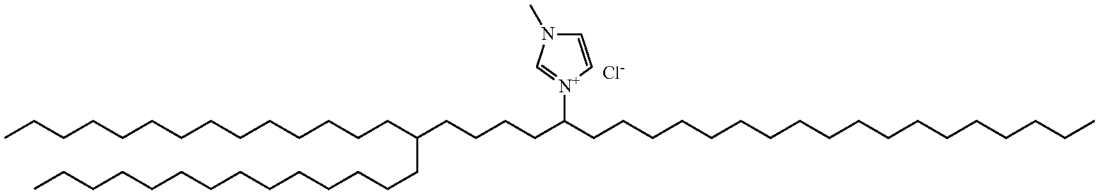 |
| W12.7 | $CH_3$ | 4 | $C_{10}H_{21}$ | $C_{14}H_{29}$ | $C_{14}H_{29}$ | H | 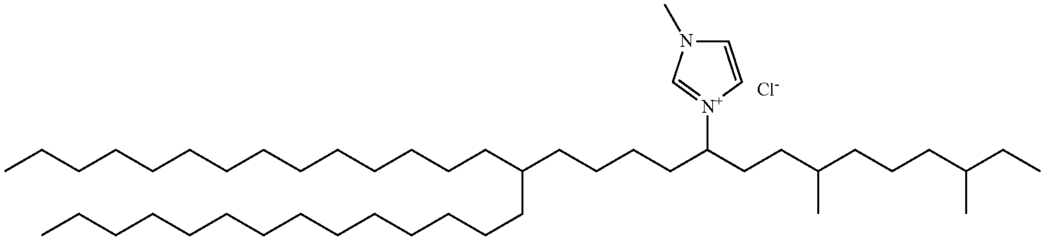 |
| W13.7 | $CH_3$ | 4 | $C_{18}H_{37}$ | $C_{18}H_{37}$ | $C_{18}H_{37}$ | H | 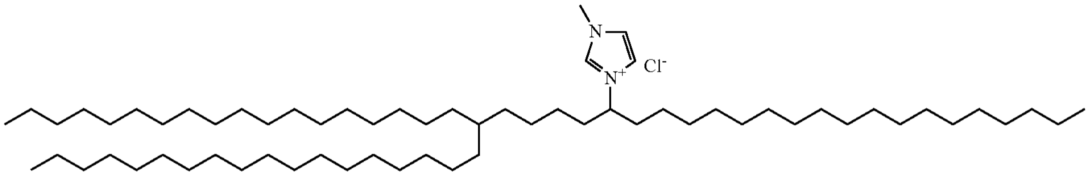 |

TABLE 1-continued
Chemical structures of imidazole- and imidazolium-based compounds
| Compound | $R_1$ | $(CH_2)_n$ n= | $R_2$ | $R_3$ | $R_4$ | $R_5$ | 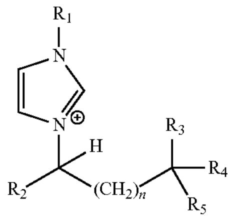 |
|---|---|---|---|---|---|---|---|
| W14.7 | $CH_3$ | 4 | $CH_2—C_6H_{12}$ | $C_{18}H_{37}$ | $C_{18}H_{37}$ | H | 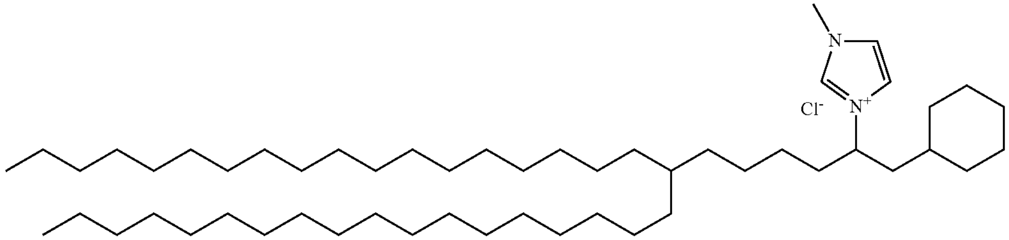 |
| W15.7 | $CH_3$ | 4 | $CH_2—C_6H_6$ | $C_{18}H_{37}$ | $C_{18}H_{37}$ | H | 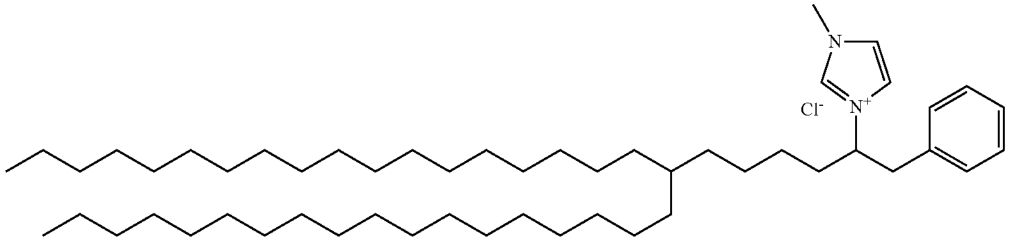 |
| W16.7 | $CH_3$ | 4 | $C_{10}H_{21}$ | $C_{18}H_{37}$ | $C_{18}H_{37}$ | H | 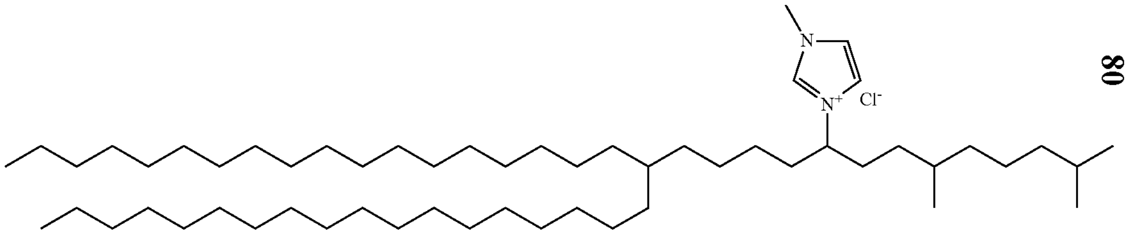 |

TABLE 1-continued
Chemical structures of imidazole- and imidazolium-based compounds
| Com-pound | $R_1$ | $(CH_2)_n$ n= | $R_2$ | $R_3$ | $R_4$ | $R_5$ | 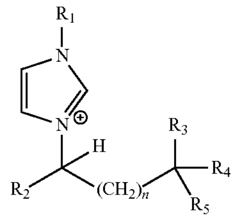 |
| --- | --- | --- | --- | --- | --- | --- | --- |
| W17.7 | $CH_3$ | 4 | $C_6H_{13}$ | $C_{18}H_{37}$ | $C_{18}H_{37}$ | H | 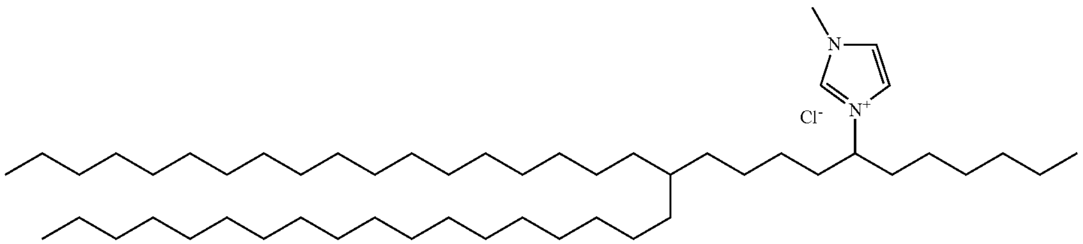 |
| W18.9 | $CH_3$ | 4 | $C_{33}H_{65}$ | $C_{14}H_{29}$ | $C_{14}H_{29}$ | H | 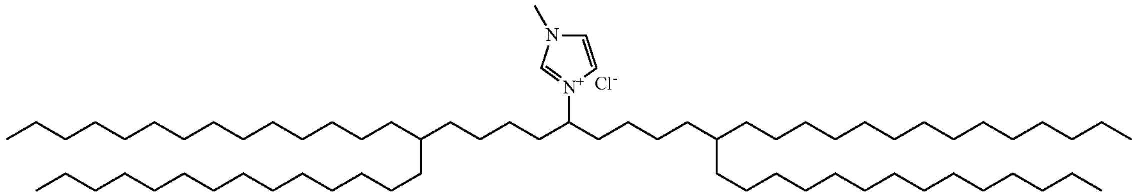 |
| W19.7 | CH3 | 3 | $C_{10}H_{21}$ | $C_{10}H_{21}$ | $NH_2—C_{18}H_{37}$ | H | 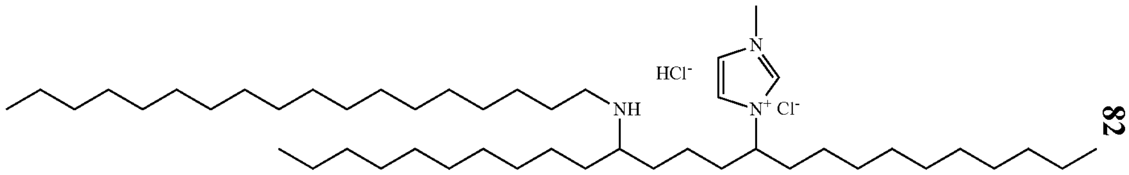 |

TABLE 1-continued
Chemical structures of imidazole- and imidazolium-based compounds
| Compound | $R_1$ | $(CH_2)_n$ n= | $R_2$ | $R_3$ | $R_4$ | $R_5$ | 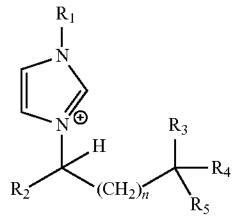 |
|---|---|---|---|---|---|---|---|
| W20.7 | $C_4H_9$ | 4 | $C_{18}H_{35}$ | $C_{14}H_{29}$ | $C_{14}H_{29}$ | H | 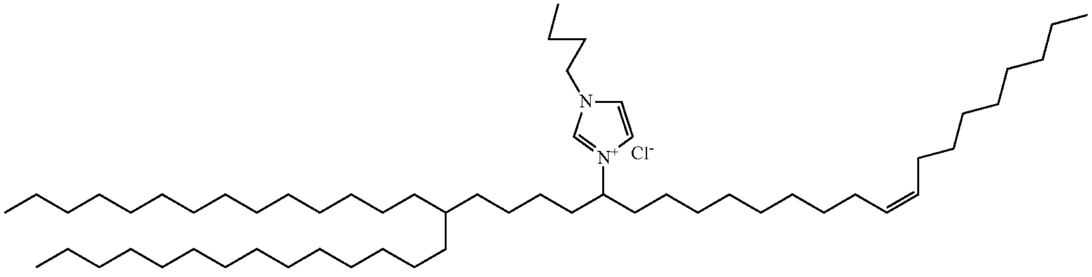 [SMILES: CCCCCCCC/C=C\CCCCCCCCC(CCCCC(CCCCCCCCCCCCCC)CCCCCCCCCCCCCC)[n+]1ccn(CCCC)c1 ; [Cl-]] |
| W21.7 | $C_4H_9$ | 4 | $C_{10}H_{21}$ | $C_{18}H_{37}$ | $C_{18}H_{37}$ | H | 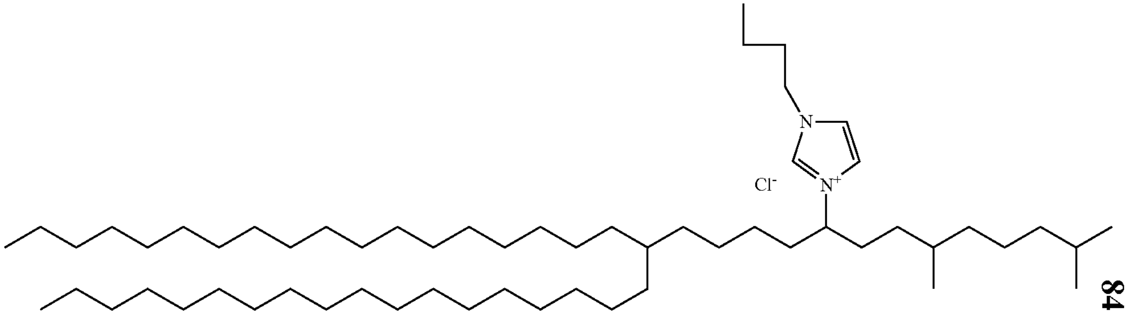 |

TABLE 1-continued
Chemical structures of imidazole- and imidazolium-based compounds
| Compound | $R_1$ | $(CH_2)_n$ n= | $R_2$ | $R_3$ | $R_4$ | $R_5$ | 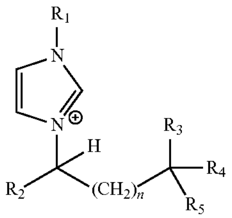 |
|---|---|---|---|---|---|---|---|
| W22.7 | $C_4H_9$ | 4 | $C_{10}H_{21}$ | $C_{14}H_{29}$ | $C_{14}H_{29}$ | H | 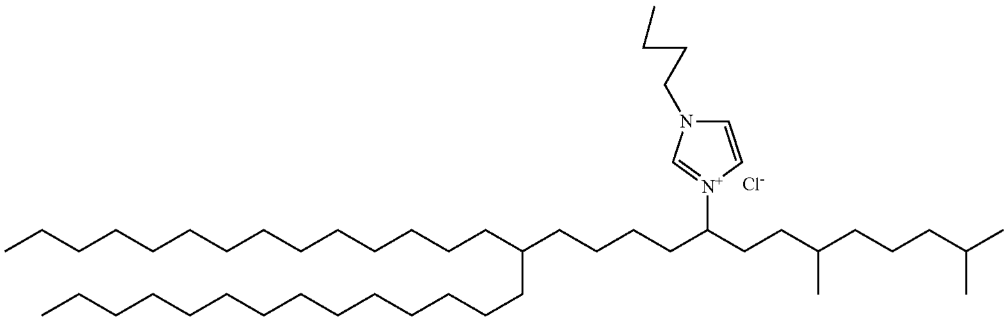 [SMILES: CCCCCCCCCCCCCCC(CCCCCCCCCCCCCC)CCCCC(CCC(C)CCCC(C)C)[n+]1ccn(CCCC)c1 ; [Cl-]] |
| W23.7 | $C_4H_9$ | 4 | $C_{10}H_{21}$ | $C_{10}H_{21}$ | $C_{10}H_{21}$ | H | 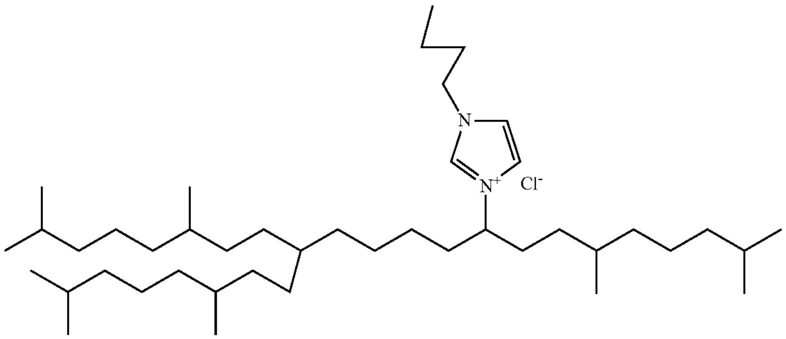 [SMILES: CCCCn1cc[n+](C(CCCCC(CCC(C)CCCC(C)C)CCC(C)CCCC(C)C)CCC(C)CCCC(C)C)c1 ; [Cl-]] |

TABLE 1-continued
Chemical structures of imidazole- and imidazolium-based compounds
| Compound | $R_1$ | $(CH_2)_n$ n= | $R_2$ | $R_3$ | $R_4$ | $R_5$ | 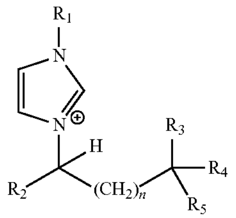 |
|---|---|---|---|---|---|---|---|
| W24.7 | H | 4 | $C_{10}H_{21}$ | $C_{18}H_{37}$ | $C_{18}H_{37}$ | H | 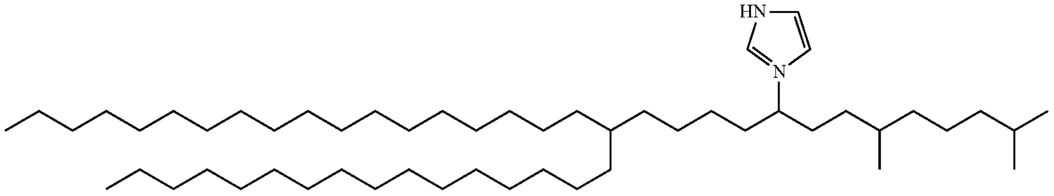 |
| W25.7 | $C_2H_4$—OH | 4 | $C_{18}H_{37}$ | $C_{14}H_{29}$ | $C_{14}H_{29}$ | H | 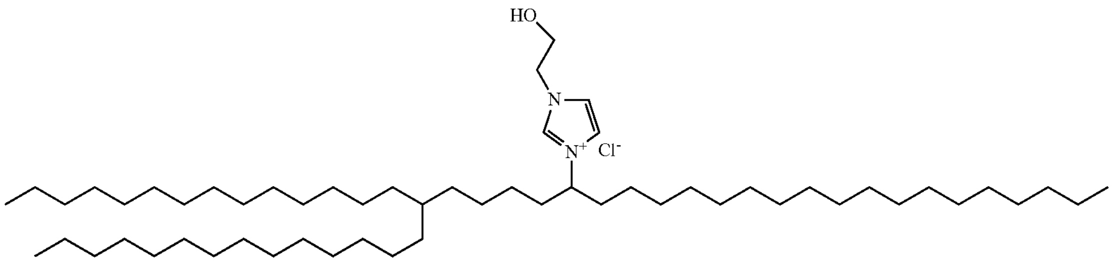 [SMILES: CCCCCCCCCCCCCCCCCCC(CCCCC(CCCCCCCCCCCCCC)CCCCCCCCCCCCCC)[n+]1ccn(CCO)c1 ; [Cl-]] |
| W26.7 | $C_2H_4$—OH | 4 | $C_{14}H_{29}$ | $C_{14}H_{29}$ | $C_{14}H_{29}$ | H | 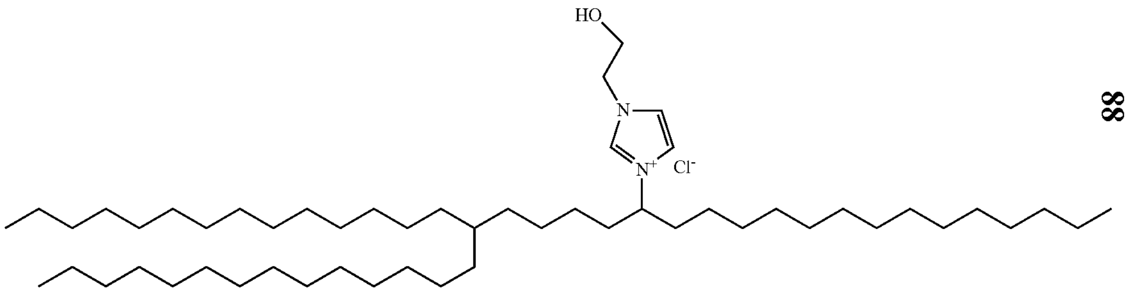 |

TABLE 1-continued
Chemical structures of imidazole- and imidazolium-based compounds
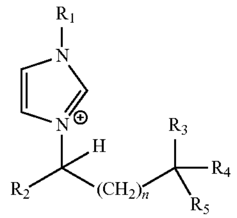
| Compound | $R_1$ | $(CH_2)_n$ n= | $R_2$ | $R_3$ | $R_4$ | $R_5$ | |
|---|---|---|---|---|---|---|---|
| W27.7 | $C_2H_5$ | 4 | $C_{18}H_{35}$ | $C_{14}H_{29}$ | $C_{14}H_{29}$ | H | 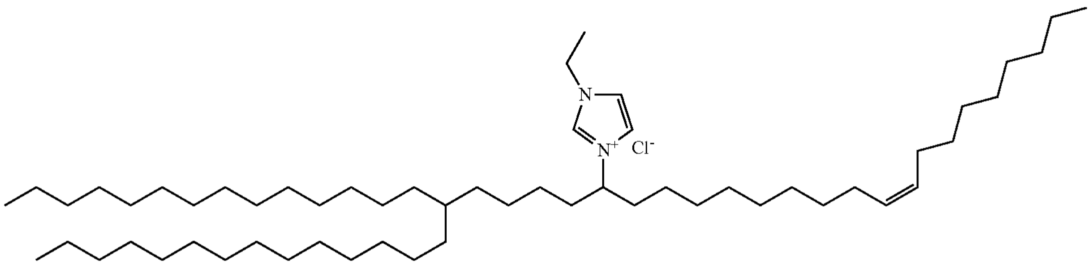 |
| W28.7 | $CH_3$ | 3 | $C_{18}H_{37}$ | $C_{14}H_{29}$ | $C_{14}H_{29}$ | H | 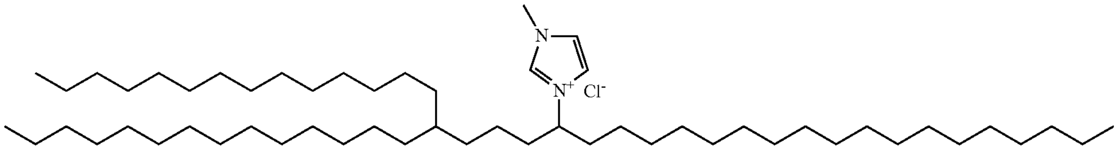 |
| W29.5 | $CH_3$ | 3 | H | $C_{16}H_{33}$ | $C_{16}H_{33}$ | H | 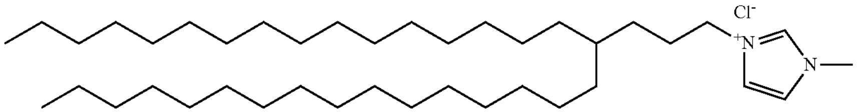 |

TABLE 2

| Transfection efficiency of eGFP mRNA in various cell lines mediated by cationic liposomal formulations. | | | | | | |
|---|---|---|---|---|---|---|
| Formulation | | | | | | |
| | | ratio compound/ | Transfection efficiency (eGFP %) | | | |
| Compound | Co-lipid | co-lipid | Jurkat | CaCO2 | THP-1 | BJ |
| W1.4 | DOPE | 1/2 | 10-15 | 15-25 | 80-85 | 80-95 |
| W2.5 | DOPE | 1/2 | 1-5 | 5-10 | 70-75 | 70-85 |
| W3.5 | DOPE | 1/2 | 10-15 | 35-40 | 35-45 | 80-95 |
| W4.3 | DOPE | 1/2 | 0-1 | 5-10 | 30-40 | 50-60 |
| W5.3 | DOPE | 1/2 | 0-2 | 5-10 | 50-60 | 60-70 |
| W6.3 | DOPE | 1/2 | 20-25 | 5-10 | 30-40 | 80-85 |
| W7.4 | DOPE | 1/2 | 5-15 | 5-15 | 40-50 | 65-75 |
| W8.7 | DOPE | 1/2 | 10-15 | nd | 70-80 | 80-85 |
| W9.7 | DOPE | 1/2 | 10-15 | 40-50 | 70-80 | 90-95 |
| W10.7 | DOPE | 1/2 | 25-30 | 65-75 | 70-80 | 90-95 |
| W11.7 | DOPE | 1/2 | 15-25 | 35-45 | 80-90 | 90-95 |
| W12.7 | DOPE | 1/2 | 35-40 | 65-80 | 80-85 | 90-95 |
| W12.7 | DPyPE | 1/2 | 40-50 | 85-90 | 80-90 | 75-80 |
| W13.7 | DOPE | 1/2 | 10-20 | 75-80 | 80-85 | 65-75 |
| W14.7 | DOPE | 1/2 | 25-35 | nd | 55-65 | nd |
| W15.7 | DOPE | 1/2 | 25-30 | nd | 55-70 | nd |
| W16.7 | DOPE | 1/2 | 35-40 | 15-20 | 75-80 | nd |
| W17.7 | DOPE | 1/2 | 30-35 | nd | 70-75 | nd |
| W18.9 | DOPE | 1/2 | 25-30 | nd | 80-85 | nd |
| W19.7 | DOPE | 1/2 | 40-50 | nd | 40-50 | nd |
| W20.7 | DOPE | 1/2 | 60-70 | 80-85 | 80-90 | 90-95 |
| W20.7 | DPyPE | 1/2 | 50-60 | nd | 65-80 | nd |
| W21.7 | DOPE | 1/2 | 40-50 | 50-60 | 70-80 | nd |
| W21.7 | DPyPE | 1/2 | 55-65 | 60-70 | 70-80 | nd |
| W22.7 | DOPE | 1/2 | 50-60 | nd | 70-80 | nd |
| W22.7 | DPyPE | 1/2 | 40-55 | nd | 80-85 | nd |
| W23.7 | DPyPE | 1/1.5 | 25-30 | nd | nd | nd |
| W24.7 | DOPE | 1/2 | 0 | nd | nd | nd |
| W24.7 | DPyPE | 1/1.5 | 0 | nd | nd | nd |
| W25.7 | DOPE | 1/2 | 25-35 | 45-55 | 80-85 | 90-95 |
| W26.7 | DOPE | 1/2 | 10-15 | 50-55 | 70-80 | 90-95 |
| W27.7 | DOPE | 1/2 | 5-10 | 65-75 | 40-50 | 90-95 |
| W28.7 | DOPE | 1/2 | 15-25 | 40-45 | 80-85 | 90-95 |
| W29.5 | DOPE | 1/2 | 10-15 | nd | 30-40 | nd |

Using the same conditions as the ones used in Table 2, the inventors also tested the transfection efficiency of eGFP mRNA mediated by a formulation comprising the compound MONI (1-Methyl-3-(1-Octadecyl-Nonadecyl)-3H-Imidazol-1-ium chloride) disclosed in the U.S. Pat. No. 8,399,422 and the neutral lipid DOPE (ratio 1/2).

This formulation was able to transfect efficiently BJ cells (50-60% GFP positive cells) and THP-1 cells (30-40% GFP positive cells) and showed a low transfection activity in Jurkat and CaCo2 cells (5-10%).

Example 31. mRNA Versus DNA Transfection

Comparative tests were undertaken using the plasmid pCMV-GFP. This plasmid has a CMV promoter and a green fluorescence protein sequence that can measure the percentage of cells that were transfected. The transfection was performed using either LipoFectamine® 3000 to transfect the plasmid or the formulation of 1-(3,7-dimethyloctyl)-6-(octadecyltetracosane)-3-butyl-1H-imidazol-1-ium chloride (W21.7) and the neutral phospholipid DPyPE (1,2-diphenytanoyl-sn-glycero-3-phosphoethanolamine) to transfect mRNA-GFP. The transfections were performed using 500 ng of plasmid and 0.75 of Lipofectamine®3000 and using 500 ng mRNA GFP or 0.8 to 1.2 µl of the formulation W21.7/DPyPE. The transfection complexes were prepared in OptiMEM® for the Liopofetamine®3000 or by adding a solution of 5% glucose containing 15 mM NaCl for the formulation W21.7/DPyPE, and were then added to the cells after incubation of 15 minutes at ambient temperature. Typically, 50 000 adherent cells or 100 000 suspension cells were seeded per well in 0.5 mL of cell growth medium containing serum or recommended supplements 24 h prior to transfection. The transfections took place in the cell cultures in the presence of serum in 24-well plates and the expression of the GFP was monitored after 24 hours of transfection by flow cytometry. The results are presented in the Table 3 below.

TABLE 3

| mRNA versus DNA transfection | | |
|---|---|---|
| Cells | Tranfection of plasmid pCMV-GFP with Lipofectamine ® 3000 % GFP | Transfection of mRNA GFP with the formulation W21.7/DPyPE % GFP |
| MDCK | 20-35% | 50-60% |
| MEF | 15% | 80% |
| IMR-90 | 10-25% | 90% |
| Hep-G2 | 30% | 90% |
| Caco-2 | 20-35% | 70-90% |
| K562 | <5% | 45-55% |
| Jurkat | <5% | 40-60% |
| HeLa | 50% | 90-100% |
| Murine Mesenchymal Stem Cells | <5% | 70-90% |
| MCF-10A | 20% | 80-90% |
| THP-1 | <10% | 70-90% |
| Human Mesenchymal Stem Cells | <10% | 90% |
| Human Dermal Fibroblasts | 30-45% | 70-80% |

CONCLUSION

The results demonstrated that the use of the formulation of the cationic lipid 1-butyl-3-(2,6-dimethyl-14-octadecyl-dotriacontan-9-yl)-1H-imidazol-3-ium chloride W21.7 and the neutral phospholipid DPyPE for transfecting mRNA was more efficient than the use of the known transfection agent Lipofectamine® for transfecting DNA.

Example 32. Particle Size and Zeta Potential Measurements by Dynamic Light Scattering (DLS)

Cationic imidazolium-based liposomes were formulated in 10% ethanol in water with neutral co-lipids at a ratio 1:1.5-2 (mM cationic lipid:mM co-lipid). The formed liposomes had an average size determined by DLS close to 100 nm as exemplified by the formulation of compound W21.7/DPyPE (ratio 1:1.5) having a mean size of 93.4+/−11.7 nm as disclosed in FIG. 2. These formulations were also positively charged as the zeta potentials were close to +50 mV as exemplified by the formulation of compound W21.7/DPyPE (ratio 1:1.5). These size and charge make suitable the formulation for in vitro use as well as for direct administration.

Example 33. Gene Editing

Gene Editing Experiment

The CRISPR-Cas9 technology was used to introduce a deletion in a targeted gene. The Cas9 protein was introduced by the transfection of mRNA encoding the Cas9 protein. The commercially available Alt-R™ CRISPR-Cas9 System from Integrated DNA Technologies (IDT) for directing Cas9 endonuclease to genomic targets was used in this experiment. This kit contained CRISPR guide RNA consisting of the Alt-R™ CRISPR crRNA (36 nt, CRISPR RNA) targeting the human HPRT-1 gene or a Negative Control crRNA and tracrRNA (89 nt transactivating CRISPR RNA) necessary for the nuclease activity of Cas9. The CleanCap™ Cas9 mRNA (4 521 nt, U-modified, Ref L-7206, TriLink Technologies) used for the transfection experiment expressed a version of the *Streptococcus pyogenes* SF370 Cas9 protein with an N and C terminal nuclear localization signal (NLS). This mRNA was capped with the Cap 1 structure, polyadenylated, and substituted with a modified uridine and optimized for mammalian systems.

Figure 4:
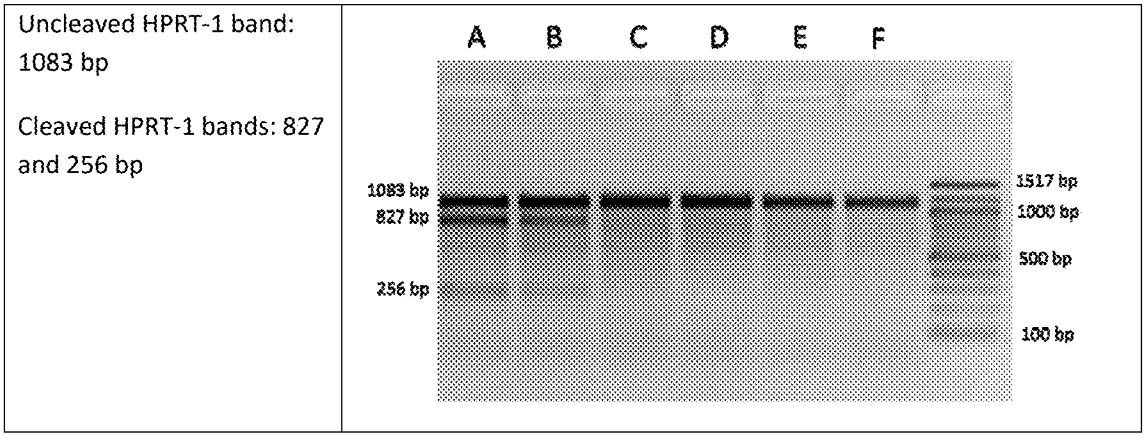
FIG. 4. Gel electrophoresis showing genome editing in HEK293 cells after co-transfection of Cas9 mRNA and guide RNA targeting the HRPT-1 gene with a cationic liposomal formulation (Compound W21.7 formulated with DPyPE at a ratio of 1:1.5).

The CRISPR guide RNA was associated by complexing HPRT-1 or Negative Control crRNA and tracrRNA and the Cas9 mRNA was added. Then, the compound W21.7 formulated with co-lipid DPyPE (ratio 1:2) was used to co-transfect the guide RNA and cas9 mRNA in HEK293 human embryonic epithelial kidney cells. 48 hours later, the genomic DNA was extracted and submitted to PCR using HPRT-1 specific primers. The genome editing event was analysed by the T7 Endonuclease assay and visualized on agarose gel and quantified using Ethidium Bromide staining to determine the % INDEL (percentage of insertion/deletion CRISPR event). The co-transfection of Cas9 mRNA (FIG. 4, conditions A & B) and HPRT-1 guide RNA showed the presence of the two expected bands on the gel at 256 bp and 827 bp. The % INDEL was 43.5% and 30.0% for the conditions A and B, respectively. The specificity of the co-transfection was shown as specific signals of cleaved band were observed after transfection of the Cas9 mRNA and Negative Control guide RNA (conditions B and C), or after transfection of the Cas9 mRNA alone (conditions E and F). The experiment demonstrated that the formulation used for the transfection was efficient to induce a CRISRP Cas9 genome modification without generating off-targets events.

Example 34. In Vivo mRNA Delivery

The mRNA-based gene transfer is becoming a promising therapeutic approach using many approaches such as the immunotherapy, genetic vaccination, correction of genetic disorders or genome editing.

mRNA encoding the firefly luciferase gene was used as reporter gene. This Luc mRNA (CleanCap™ FLuc mRNA, 1921 nt, reference L-7202, TriLink Technologies) was capped with cap 1 structure, polyadenylated, and modified with 5-methoxyuridine to minimize immune response. The compound W21.7 formulated with co-lipid DPyPE (ratio 1:1.5) was used to complex the Luc mRNA previously diluted in a 5% glucose solution. 200 μL of complexed mRNA (containing 5, 10 or 20 μg of mRNA) were administrated per mouse through retro-orbital injection. One day post-administration, the mice were sacrificed, many organs were collected and proteins were extracted. A luciferase assay (Promega) was performed to determine the luciferase activity per organ (Table 4).

TABLE 4

In vivo mRNA delivery mediated by the cationic liposomal formulation W21.7/DPyPE, ratio 1/1.5, through systemic injection into mice.

| | | RLU/organ | |
|---|---|---|---|
| mRNA amount | Organ | Mean | SD |
| 20 μg/injection | lung | 5.47E+06 | 1.48E+06 |
| | liver | 2.65E+06 | 1.14E+06 |
| | spleen | 5.12E+07 | 4.72E+07 |
| | kidney | 1.29E+05 | 4.30E+04 |
| | heart | 1.27E+05 | 3.60E+04 |
| | pancreas | 6.44E+04 | 2.72E+04 |
| 10 μg/injection | lung | 5.42E+06 | 4.13E+04 |
| | liver | 3.20E+06 | 9.19E+05 |
| | spleen | 7.57E+07 | 4.57E+07 |
| | kidney | 1.46E+05 | 6.33E+04 |
| | heart | 8.22E+04 | 2.91E+04 |
| | pancreas | 1.23E+05 | 1.31E+05 |
| 5 μg/injection | lung | 6.22E+05 | 4.01E+05 |
| | liver | 3.29E+05 | 2.34E+05 |
| | spleen | 1.54E+07 | 5.20E+06 |
| | kidney | 8.27E+04 | 2.49E+04 |
| | heart | 5.96E+04 | 1.37E+04 |
| | pancreas | 3.72E+04 | 1.47E+04 |

Luc mRNA/cationic liposome complexes were intravenously injected through the retro-orbital sinus with various mRNA amount (5, 10 or 20 μg per injection). The level of luciferase expression in many extracted organs was determined one day after the injection. 6 mice were injected per conditions.

A high luciferase expression was found in the spleen, following by an expression lung and liver and a very low level in the other tested organs (pancreas, kidney, heart). The injected amount of mRNA of 10 and 20 μg provided similar profile and level of expression. The luciferase activity decreased after injection of 5 μg mRNA but was still significant in the spleen.

Another experiment (Table 5) was done by varying the ratio of cationic lipid and co-helper DPyPE lipid from 1:1 to 1:2. 20 μg of mRNA was formulated with these liposomal formulations and injected per mice. The optimal luciferase expression was found with the ratio of 1:1.5 with a similar profile expression observed in the previous in vivo experiment. The cationic lipid was also formulated with the co-lipid DOPE at the ratio 1:1.5 and this formulation showed similar levels and profile of luciferase expression (spleen, liver and lung) than the formulation with DPyPE at the same ratio 1:1.5.

TABLE 5

Effect of the ratio of cationic lipid to co-helper lipid on in vivo mRNA delivery after systemic injection into mice.

| Cationic liposomal formulation | Organ | RLU/organ Mean | SD |
|---|---|---|---|
| 4 mM W21.7/4 mM DPyPE | lung | 1.50E+06 | 1.39E+06 |
| | liver | 3.47E+05 | 2.33E+05 |
| | spleen | 1.96E+07 | 1.11E+07 |
| | kidney | 1.50E+05 | 3.81E+04 |
| | heart | 1.94E+05 | 4.80E+04 |
| | pancreas | 1.18E+05 | 2.54E+04 |
| 4 mM W21.7/6 mM DPyPE | lung | 1.16E+07 | 9.42E+06 |
| | liver | 1.17E+07 | 6.89E+06 |
| | spleen | 1.49E+08 | 1.22E+08 |
| | kidney | 3.61E+05 | 1.14E+05 |

TABLE 5-continued

Effect of the ratio of cationic lipid to co-helper lipid on in vivo mRNA delivery after systemic injection into mice.

| Cationic liposomal | | RLU/organ | |
|---|---|---|---|
| formulation | Organ | Mean | SD |
| | heart | 1.21E+06 | 7.42E+05 |
| | pancreas | 1.26E+05 | 8.05E+04 |
| 4 mM W21.7/8 mM DPyPE | lung | 8.71E+05 | 4.47E+05 |
| | liver | 7.30E+05 | 3.23E+05 |
| | spleen | 2.26E+07 | 2.27E+07 |
| | kidney | 9.36E+04 | 2.18E+04 |
| | heart | 1.05E+05 | 1.75E+04 |
| | pancreas | 7.51E+04 | 1.15E+04 |
| 4 mM W21.7/6 mM DOPE | lung | 1.58E+07 | 1.47E+07 |
| | liver | 3.18E+06 | 2.83E+06 |
| | spleen | 5.95E+07 | 4.45E+07 |
| | kidney | 3.98E+05 | 2.83E+05 |
| | heart | 6.90E+05 | 5.20E+05 |
| | pancreas | 7.71E+04 | 2.93E+04 |

While the invention has been described in terms of various preferred embodiments, the skilled person will appreciate that various modifications, substitutions, omissions and changes may be made without departing from the scope thereof. Accordingly, it is intended that the scope of the present invention be limited by the scope of the following claims, including equivalents thereof.

REFERENCES

Chiper M, Tounsi N, Kole R, Kichler A, Zuber G. Self-aggregating 1.8 kDa polyethylenimines with dissolution switch at endosomal acidic pH are delivery carriers for plasmid DNA, mRNA, siRNA and exon-skipping oligonucleotides. Journal of controlled release: official journal of the Controlled Release Society 2017; 246:60-70.

De Haes W, Rejman J, Pollard C, Merlin C, Vekemans M, Florence E, et al. Lipoplexes carrying mRNA encoding Gag protein modulate dendritic cells to stimulate HIV-specific immune responses. Nanomedicine (Lond) 2013; 8:77-87.

Doudna J A, Charpentier E. Genome editing. The new frontier of genome engineering with CRISPR-Cas9. Science 2014; 346:1258096.

Drews K, Tavernier G, Demeester J, Lehrach H, De Smedt S C, Rejman J, et al. The cytotoxic and immunogenic hurdles associated with non-viral mRNA-mediated reprogramming of human fibroblasts. Biomaterials 2012; 33:4059-68.

Goncalves C, Akhter S, Pichon C, Midoux P. Intracellular Availability of pDNA and mRNA after Transfection: A Comparative Study among Polyplexes, Lipoplexes, and Lipopolyplexes. Molecular pharmaceutics 2016; 13:3153-63.

Goncalves C, Berchel M, Gosselin M P, Malard V, Cheradame H, Jaffres P A, et al. Lipopolyplexes comprising imidazole/imidazolium lipophosphoramidate, histidinylated polyethyleneimine and siRNA as efficient formulation for siRNA transfection. International journal of pharmaceutics 2014; 460:264-72.

Heil F, Hemmi H, Hochrein H, Ampenberger F, Kirschning C, Akira S, et al. Species-specific recognition of single-stranded RNA via toll-like receptor 7 and 8. Science 2004; 303:1526-9.

Jarzebinska A, Pasewald T, Lambrecht J, Mykhaylyk O, Kummerling L, Beck P, et al. A Single Methylene Group in Oligoalkylamine-Based Cationic Polymers and Lipids Promotes Enhanced mRNA Delivery. Angew Chem Int Ed Engl 2016; 55:9591-5.

Kaczmarek J C, Kowalski P S, Anderson D G. Advances in the delivery of RNA therapeutics: from concept to clinical reality. Genome medicine 2017; 9:60.

Kariko K, Buckstein M, Ni H, Weissman D. Suppression of RNA recognition by Toll-like receptors: the impact of nucleoside modification and the evolutionary origin of RNA. Immunity 2005; 23:165-75.

Kariko K, Muramatsu H, Keller J M, Weissman D. Increased erythropoiesis in mice injected with submicrogram quantities of pseudouridine-containing mRNA encoding erythropoietin. Molecular therapy: the journal of the American Society of Gene Therapy 2012; 20:948-53.

Kariko K, Muramatsu H, Ludwig J, Weissman D. Generating the optimal mRNA for therapy: HPLC purification eliminates immune activation and improves translation of nucleoside-modified, protein-encoding mRNA. Nucleic acids research 2011; 39:e142.

Kariko K, Ni H, Capodici J, Lamphier M, Weissman D. mRNA is an endogenous ligand for Toll-like receptor 3. The Journal of biological chemistry 2004; 279:12542-50.

Kormann M S, Hasenpusch G, Aneja M K, Nica G, Flemmer A W, Herber-Jonat S, et al. Expression of therapeutic proteins after delivery of chemically modified mRNA in mice. Nature biotechnology 2011; 29:154-7.

Lv P, Zhou C, Zhao Y, Liao X, Yang B. Modified-epsilon-polylysine-grafted-PEI-beta-cyclodextrin supramolecular carrier for gene delivery. Carbohydrate polymers 2017; 168:103-11.

Malone R W, Felgner P L, Verma I M. Cationic liposome-mediated RNA transfection. Proceedings of the National Academy of Sciences of the United States of America 1989; 86:6077-81.

Ran F A, Hsu P D, Lin C Y, Gootenberg J S, Konermann S, Trevino A E, et al. Double nicking by RNA-guided CRISPR Cas9 for enhanced genome editing specificity. Cell 2013; 154:1380-9.

Ran F A, Hsu P D, Wright J, Agarwala V, Scott D A, Zhang F. Genome engineering using the CRISPR-Cas9 system. Nature protocols 2013; 8:2281-308.

Rejman J, Tavernier G, Bavarsad N, Demeester J, De Smedt S C. mRNA transfection of cervical carcinoma and mesenchymal stem cells mediated by cationic carriers. Journal of controlled release: official journal of the Controlled Release Society 2010; 147:385-91.

Tavernier G, Andries O, Demeester J, Sanders N N, De Smedt S C, Rejman J. mRNA as gene therapeutic: how to control protein expression. Journal of controlled release: official journal of the Controlled Release Society 2011; 150:238-47.

Warren L, Manos P D, Ahfeldt T, Loh Y H, Li H, Lau F, et al. Highly efficient reprogramming to pluripotency and directed differentiation of human cells with synthetic modified mRNA. Cell stem cell 2010; 7:618-30.

Yamamoto A, Kormann M, Rosenecker J, Rudolph C. Current prospects for mRNA gene delivery. European journal of pharmaceutics and biopharmaceutics: official journal of Arbeitsgemeinschaft fur Pharmazeutische Verfahrenstechnik eV 2009; 71:484-9.

Yoshioka N, Gros E, Li H R, Kumar S, Deacon D C, Maron C, et al. Efficient generation of human iPSCs by a synthetic self-replicative RNA. Cell stem cell 2013; 13:246-54.

Zhao M, Li M, Zhang Z, Gong T, Sun X. Induction of HIV-1 gag specific immune responses by cationic micelles mediated delivery of gag mRNA. Drug delivery 2016; 23:2596-607.

The invention claimed is:

1. A composition suitable for transfecting a messenger RNA (mRNA) into a cell comprising a mRNA, at least one neutral lipid and a cationic lipid of formula (I):

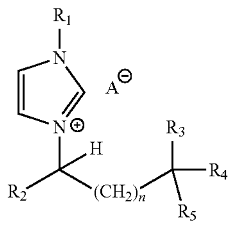

(I)

wherein $R_1$ represents $CH_3$; $R_2$ represents a $C_6$-$C_{33}$ saturated or unsaturated, linear or branched hydrocarbon chain; or a saturated or unsaturated $C_6$ cycle; $R_3$ and $R_4$ represent a $C_{14}$-$C_{18}$ saturated or unsaturated alkyl chain; or $R_1$ represents $CH_2$—$CH_2$—$CH_2$—$CH_3$; $R_2$, $R_3$ and $R_4$ represent a $C_{10}$-$C_{18}$ saturated or unsaturated alkyl chain; or $R_1$ represents hydroxyethyl or ethyl; $R_2$, $R_3$ and $R_4$ represent a $C_{14}$-$C_{18}$ saturated or unsaturated alkyl chain; or $R_1$ represents $C_2H_5$; $R_2$ represents a $C_{18}$ unsaturated alkyl chain; $R_3$ and $R_4$ represent a Cas saturated alkyl chain;

$R_5$ represents H;

$(CH_2)_n$ represents a hydrocarbon chain linker with n=4;

$A^-$ represents a biocompatible anion.

2. The composition according to claim 1, wherein the at least one neutral lipid is selected from the group consisting of phosphatidylserine (PS), phosphatidylcholine (PC), phosphatidylinositol (PI) derivatives, lipid-PolyEthyleneGlycol (PEG) conjugates, cholesterol derivatives and phosphatidylethanolamine derivatives.

3. The composition according to claim 1, wherein the cationic lipid of formula (I) is selected from the group consisting of the following compounds:

W9.7

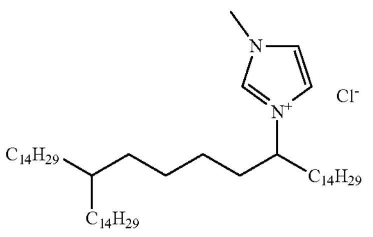

1-methyl-3-(20-tetradecyltetratriacontan-15-yl)-1H-imidazol-3-ium chloride

-continued

W10.7

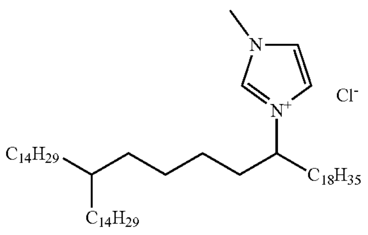

1-methyl-3-(24-tetradecyloctatriacont-9-en-19-yl)-1H-imidazol-3-ium chloride

W11.7

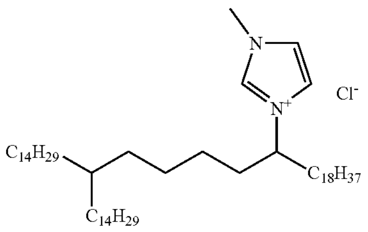

1-methyl-3-(24-tetradecyloctatriacontan-19-yl)-1H-imidazol-3-ium chloride

W12.7

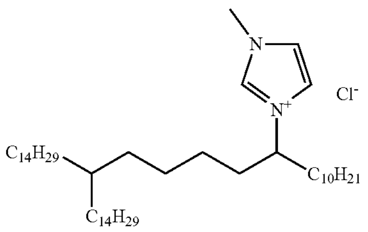

1-methyl-3-(2,6-dimethyl-14-tetradecyloctacosan-9-yl)-1H-imidazol-3-ium chloride

W13.7

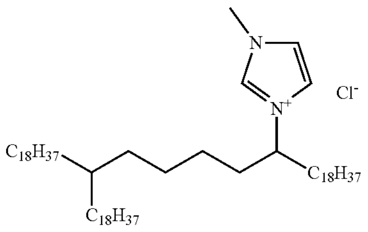

1-methyl-3-(24-octadecyldotetracontan-19-yl)-1H-imidazol-3-ium chloride

W14.7

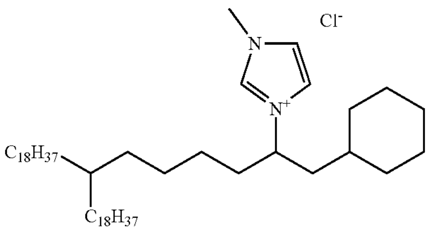

1-methyl-3-(1-cyclohexyl-7-octadecylpentacosan-2-yl)-1H-imidazol-3-ium chloride

W15.7

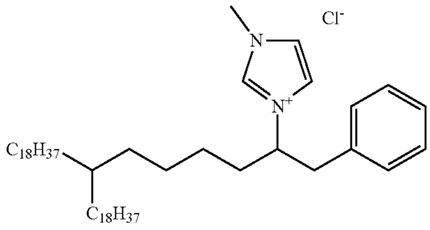

1-methyl-3-(7-octadecyl-1-phenylpentacosan-2-yl)-1H-imidazol-3-ium chloride

W16.7

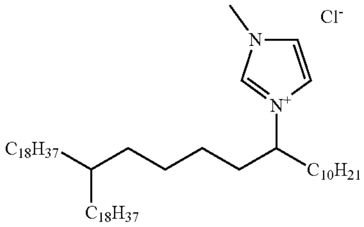

1-methyl-3-(2,6-dimethyl-14-octadecyldotriacontan-9-yl)-1H-imidazol-3-ium chloride

W17.7

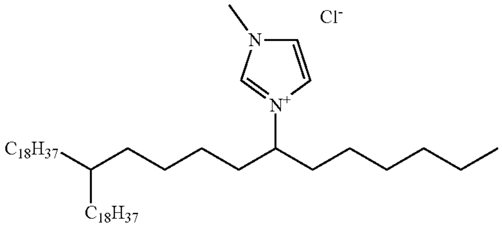

1-methyl-3-(12-octadecyltriacontan-7-yl)-1H-imdiazol-3-ium chloride

W18.9

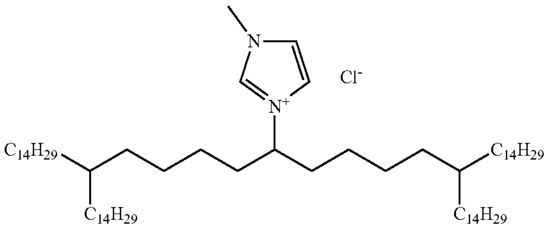

1-methyl-3-(15,25-ditetradecylnonatriacontan-20-yl)-1H-imdiazol-3-ium chloride

W20.7

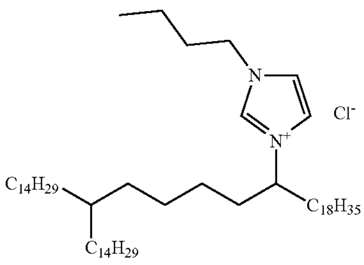

1-butyl-3-(24-tetradecyloctatriacont-9-en-19-yl)-1H-imidazol-3-ium chloride

W21.7

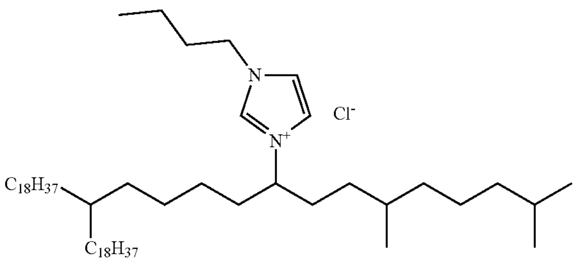

1-butyl-3-(2,6-dimethyl-14 octadecyldotriacontan-9-yl)-1H-imidazol-3-ium chloride

W22.7

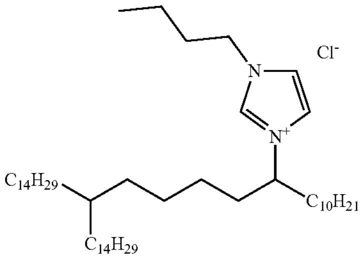

1-butyl-3-(2,6-dimethyl-14-tetradecyloctacosan-9-yl)-1H-imidazol-3-ium chloride

W23.7

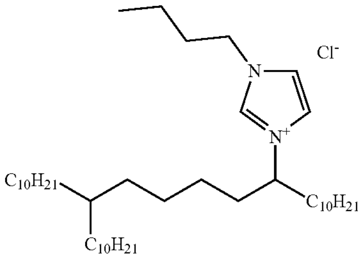

1-butyl-3-(14-(3,7-dimethyloctyl)-2,6,17,21-tetramethyldocosan-9-yl)-1H-imidazol-3-ium chloride

W25.7

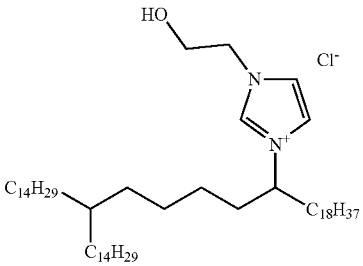

1-(2-hydroxyethyl)-3-(24-tetradecyloctatriacontan-19-yl)-1H-imidazol-3-ium chloride -continued

W26.7

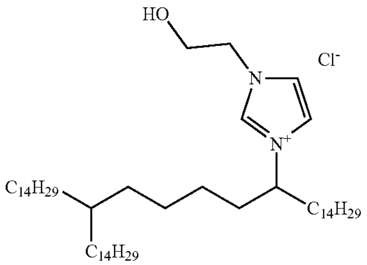

1-(2-hydroxyethyl)-3-(20-tetradecyltetratriacontan-15-yl)-1H-imidazol-3-ium chloride

W27.7

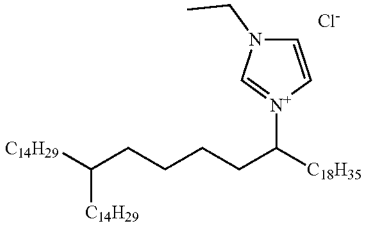

1-ethyl-3-(24-tetradecyloctatriacont-9-en-19-yl)-1H-imidazol-3-ium chloride

4. The composition according to claim 3, wherein the cationic lipid of formula (I) is selected from the group consisting of the following compounds:

W12.7

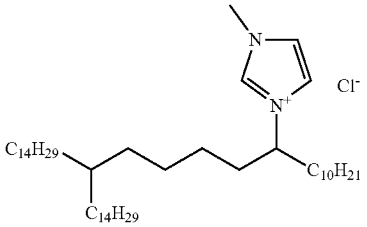

1-methyl-3-(2,6-dimethyl-14-tetradecyloctacosan-9-yl)-1H-imidazol-3-ium chloride

W20.7

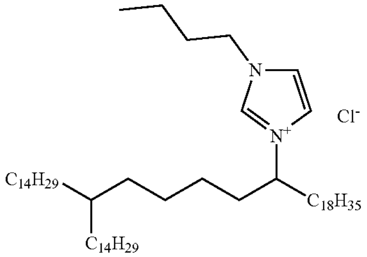

1-butyl-3-(24-tetradecyloctatriacont-9-en-19-yl)-1H-imidazol-3-ium chloride

-continued

W21.7

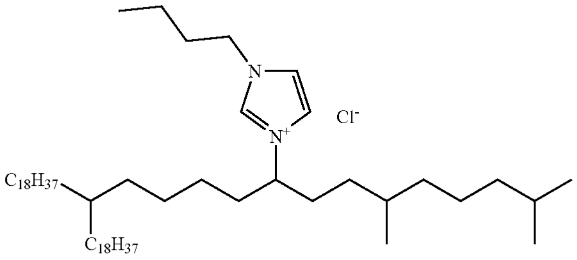

1-butyl-3-(2,6-dimethyl-14-octadecyldotriacontan-9-yl)-1H-imidazol-3-ium chloride

W22.7

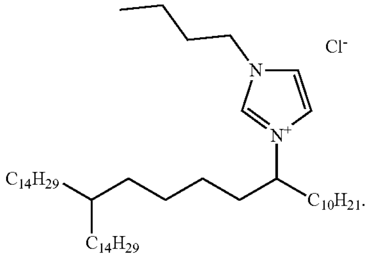

1-butyl-3-(2,6-dimethyl-14-tetradecyloctacosan-9-yl)-1H-imidazol-3-ium chloride

5. The composition according to claim 1, wherein A represents $Cl^-$ or $OH^-$.

6. The composition according to claim 1, wherein the molar ratio of the cationic lipid of formula (I) to the at least one neutral lipid ranges from 1:1 to 1:2.

7. The composition according to claim 1, wherein the 5'-end of the mRNA is capped.

8. The composition according to claim 1, wherein the mRNA is further 3'-end polyadenylated and/or contains modified nucleosides.

9. The composition according to claim 1, wherein the mRNA encodes a protein.

10. The composition according to claim 1, further comprising a compound selected from the group consisting of (i) a distinct mRNA for co-transfection, (ii) a short non-coding RNA.

11. A method for providing in vivo mRNA-based therapy, comprising administering an effective amount of the composition of claim 1 to a patient in need thereof.

12. A method for in vitro transfection of live cells comprising introducing in the cells the composition according to claim 1.

13. A method for transfecting a mRNA into a cell, comprising introducing into the cell the composition of claim 1.

14. The composition according to claim 1, wherein the at least one neutral lipid is 1,2-diphenytanoyl-sn-glycero-3-phosphoethanolamine (DPyPE).

15. The composition according to claim 1, wherein the at least one neutral lipid is 1,2-Dioleoyl-sn glycero-3-phosphoethanolamine (DOPE).

* * * * *